US006890748B2

(12) United States Patent
Garger et al.

(10) Patent No.: US 6,890,748 B2
(45) Date of Patent: May 10, 2005

(54) PRODUCTION OF LYSOSOMAL ENZYMES IN PLANTS BY TRANSIENT EXPRESSION

(75) Inventors: Stephen J. Garger, Vacaville, CA (US); Thomas H. Turpen, Vacaville, CA (US); Monto H. Kumagai, Davis, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 81 days.

(21) Appl. No.: 10/103,327

(22) Filed: Mar. 20, 2002

(65) Prior Publication Data

US 2003/0106095 A1 Jun. 5, 2003

Related U.S. Application Data

(63) Continuation of application No. 09/993,059, filed on Nov. 13, 2001, which is a continuation-in-part of application No. 09/626,127, filed on Jul. 26, 2000.

(51) Int. Cl.[7] .............................. C12N 9/40; C12Q 1/34; C12P 21/06; C07K 17/00; C07H 21/04
(52) U.S. Cl. ..................... 435/208; 435/18; 435/69.1; 435/320.1; 435/69.8; 530/350; 536/23.2
(58) Field of Search ................... 435/18, 69.1, 208, 435/320.1, 69.8; 536/23.2; 530/350

(56) References Cited

U.S. PATENT DOCUMENTS

| | | | |
|---|---|---|---|
| 5,179,023 A | 1/1993 | Calhoun et al. | 435/320.1 |
| 5,316,931 A | 5/1994 | Donson et al. | 435/172.3 |
| 5,356,804 A | * 10/1994 | Desnick et al. | 435/208 |
| 5,401,650 A | 3/1995 | Desnick et al. | 435/208 |
| 5,580,757 A | 12/1996 | Desnick et al. | 435/69.7 |
| 5,589,367 A | 12/1996 | Donson et al. | 435/172.3 |
| 5,618,699 A | 4/1997 | Hamamoto et al. | 435/69.7 |
| 5,929,304 A | 7/1999 | Radin et al. | 800/288 |
| 5,955,647 A | 9/1999 | Fitchen et al. | 800/205 |
| 5,977,438 A | 11/1999 | Turpen et al. | 800/288 |
| 6,033,895 A | 3/2000 | Garger et al. | 435/239 |
| 6,042,832 A | 3/2000 | Koprowski et al. | 424/192.1 |
| 6,210,666 B1 | 4/2001 | Miyamura | 424/94.61 |
| 6,232,099 B1 | 5/2001 | Chapman et al. | 435/69.3 |

FOREIGN PATENT DOCUMENTS

| | | |
|---|---|---|
| EP | 0 174 759 A1 | 3/1986 |
| EP | 0 197 809 A1 | 9/1986 |
| EP | 0 672 754 A1 | 9/1995 |
| EP | 72/6312 A | 8/1996 |
| WO | WO 92/18618 | 10/1992 |
| WO | WO 95/21248 A1 | 8/1995 |
| WO | WO 96/02649 A1 | 1/1996 |
| WO | WO 96/12027 | 4/1996 |
| WO | WO 96/12028 | 4/1996 |
| WO | WO 97/10353 | 3/1997 |
| WO | WO 97/39134 | 10/1997 |
| WO | WO 97/49425 | 12/1997 |
| WO | WO 99/46288 | 9/1999 |

OTHER PUBLICATIONS

Witkowski et al., Biochemistry 38:11643–11650, 1999.*
Broun et al., Science 282:1315–1317, 1998.*
Seffernick et al., J. Bacteriol. 183(8):2405–2410, 2001.*
Bork, Genome Research, 10:398–400, 2000.*
Broun et al., Science 282:1315–1317, 1998.*
Seffernick et al., J. Bacteriol. 183(8):2405–2410, 2001.*
Witkowski et al., Biochemistry 38:11643–11650, 1999.*
Kornreich et al., Swiss Prot accession No. AGAL_Human, Jan., 1988.*
Brady, "Fabry Disease", *Peripheral Neropathym*, 3rd ed., 1169–1178 (1993), W.B. Saunders.
Desnick, et al., "α –Galactosidase A Deficiency: Fabry Disease", *The Metabolic Bases of Inherited Disease*, Chapter 89, pp. 2741–2784 (1995), McGraw–Hill.
Baker, et al., "Polyethylenimine (PEI) is a Simple, Inexpensive and Effective Reagent for Condensing and Linking Plasmid DNA to Adenovirus for Gene Delivery," *Gene Therapy*, 4:773–782.
Chapman, et al., "Potato virus X as a vector for gene expression in plants," *The Plant Journal*, 2(4):549–557 (1992).
Cramer, *American Journal of Human Genetics*, 57(4), 1995.
Dawson, et al., "A Tobacco Mosaic Virus–Hybrid Expresses and Loses an Added Gene," *Virol.* 172:285–292 (1989).
Dawson, et al., "cDNA Cloning of the Complete Genome of Tobacco Mosaic Virus and Production of Infectious Transcripts," *Proc. Natl. Acad. Sci. USA* 83:1832–1836 (1986).
Dawson, et al., "Modifications of the Tobacco Mosaic Virus Coat Protein Gene Affecting Replication, Movement, and Symptomatology," *Mol. Plant Pathol*, 78(6):783–789 (1988).

(Continued)

*Primary Examiner*—Rebecca E. Prouty
*Assistant Examiner*—Delia M. Ramirez
(74) *Attorney, Agent, or Firm*—John C. Robbins; Thomas Gallegos; John E. Tarcza

(57) ABSTRACT

The invention relates to α-galactosidase truncated at the carboxy terminus and the production of enzymatically active recombinant human and animal lysosomal enzymes involving construction and expression of recombinant expression constructs comprising coding sequences of human or animal lysosomal enzymes in a plant expression system. The plant expression system provides for post-translational modification and processing to produce a recombinant gene product exhibiting enzymatic activity. The invention is demonstrated by working examples in which transgenic tobacco plants express recombinant expression constructs comprising human glucocerebrosidase nucleotide sequences. The invention is also demonstrated by working examples in which transfected tobacco plants express recombinant viral expression constructs comprising human α galactosidase nucleotide sequences. The recombinant lysosomal enzymes produced in accordance with the invention may be used for a variety of purposes, including but not limited to enzyme replacement therapy for the therapeutic treatment of human and animal lysosomal storage diseases.

3 Claims, 18 Drawing Sheets

OTHER PUBLICATIONS

Donson, et al., "Systemic Expression of Bacterial Gene by a Tobacco Mosaic Virus-based Vector," *Proc. Natl. Acad. Sci. USA*, 88:7204–7208 (1991).

Erickson, et al., "BioSynthesis of the Lysosomal Enzyme Glucocerebrosidase," *Journal of Biological Chemistry*, 260(26):14319–14324 (1985).

Ferrari, et al., "Cloning and expression of a soluble sialidase from Chinese hamster ovary cells: sequence alignment similarities to bacterial slalidases," *Clycobiology*, 4(3):367–373 (1994).

Furbish, et al., "Enzyme replacement therapy in Gaucher's disease: Large-scale purification of glucocerebrosidase suitable for human administration," *Proc. Natl. Acad. Sci. USA*, 71(8) 3560–3563 (1977).

Furbish, et al., "Uptake and Distribution of Placental Glucocerebrosidase in at Hepatic Cells and Effects of Sequential Deglycosylation," *Biochemica et Biophysica Acta*. 673:425–434 (1981).

Grabowski, et al., "Expression of Functional Human Acid β-Glucosidase in COS-1 and *Spordoptera frugiperda* Cells," *Enzyme* 41:131–142 (1989).

Grace, et al., "Analyses of Catalytic Activity and Inhibitor Binding of Human Acid β-Glucosidase by Site-directed Mutagenesis," *Journal Biological Chemistry*, pp. 6827–6835 (1989).

Grace, et al., "Analysis of Human Acid β-Glucosidase by Cite-Directed Mutagenesis and Heterologous Expression," *Journal of Biological Chemistry* 269(3):2283–2291 (1994).

Grace, et al., "Human Acid β-Glucosidase: Glycosylation is Required for Catalytic Activity," *Biochemical and Biophysical Research Communications* 168(2):771–777 (1990).

Hamamoto, et al., "A New Tobacco Mosaic Virus Vector and its Use for the Systemic Production of Anglotensin-I-Converting Enzyme Inhibitor in Transgenic Tobacco and Tomato," *Bio/Technol.*, 11:930–932 (1993).

Haynes, et al., "Development of Genetically-Engineered, Candidate Polio Vaccine Employing the Self-assembling Properties of the Tobacco Mosaic Virus Coat Protein," *Bio/Technol.*, 4:637–641 (1986).

Hopp, et al., "A Short Polypeptide Marker Sequence Useful for Recombinant Protein Identification and Purification," *Biotechnology* 6:1204–1210 (1988).

Iiaskins, et al., Alpha-L-Iduronidase Deficiency in a Cat: A Model of Mucopolysaccharidosis I, *Pediat. Res.* 13:1294–1297 (1979).

Jagadish, et al., "High Level Production of Hybrid Potyvirus-like Particles Carrying Repetitive Copies of Foreign Antigens in *Escherichia Coli*," *Bio/Technol.*, 11:1166–1170 (1993).

Jonsson, et al., "Biosynthesis and naturation of glucocerebrosidase in Gaucher fibroblasts," *J. Biochem.* 104:171–179 (1987).

Kaplan, et al., "Phosphohexosyl components of a lysosomal enzyme are recognized by pinocytosis receptors on human fibroblasts," *Proc. Natl. Acad. Sci. USA* 74(5):2026–2030 (1977).

Kornfeld, et al., "The Biognesis of Lysosomes," *Annu. Rev. Cell Biol.* 5:483–525 (1989).

Krebbers, et al., "Prospects and Progress In the Production of Foreign Proteins and Peptides in Plants," *Plant Protein Engineering*, Shewry, et al., Eds. Cambridge University Press, Cambridge, pp. 316–324 (1992).

Miyamura, et al., "A Carboxy-terminal Truncation of Human α-Galactosidase A in a Heterozygous Female with Fabry Disease and Modification of the Enzymatic Activity by the Carboxy-terminal Domain," *J. Clin. Invest.*, 98(8):1809–1817 (1996).

Murray, "Lectin-Specific Targeting of Lysosomal Enzymes to Reticuloendothelial Cells," *Methods in Enzymology*, 149:25, 39, 41, 42 (1987).

Park, et al., "Structure and nucleotide sequence of tomato HMG2 encoding 3-hydroxy-3-methyl-glutaryl coenzyme A reductase," *Plant Molecular Biology* 20:327–331 (1992).

Schatzle, et al., "Molecular Cloning and Characterization of the Structural Gene Coding for the Developmentally Regulated Lysosmal Enzyme, α-Mannosidase, In *Dictystelium discoideum*," *Journal of Biological Chemistry* 267(6):4000–4007 (1991).

Scott, et al., "Human α-L-iduronidase: cDNA isolation and expression," *Proc. Natl. Acad. Sci. USA*, 88:9695–9699 (1991).

Scott, et al., "Structure and Sequence of the Human α-L-Iduronidase Gene," *Genomics* 13:1311–1313 (1992).

Shull, et al., "Enzyme replacement in a canine model for Hurler syndrome," *Proc. Natl. Acad. Sci. USA*, 91:12917–12941 (1994).

Takamatsu, et al., "Expression of Bacterial Chloramphenicol Acetyltransferase Gene in Tobacco Plants Mediated by TMV-RNA," *EMBO J.*, 6(2):307–311 (1987).

Takamatsu, et al., "Production of Enkephalin in Tobacco Protoplasts Using Tobacco Mosaic Virus RNA vector," *FEBS Lett.*, 269(1):73–76 (1990).

Turpen, et al., "Malarial Epitopes Expressed on the Surface of a Recombinant Tobacco Mosaic Virus," *Bio/Technol.*, 13:53–57 (1995).

Usha, et al., "Expression of an Animal Virus Antigenic Site on the Surface of a Plant Virus Particle," *Virol.*, 197:366–374 (1993).

Yusibov, et al., "Antigens Produced in Plants by Infection with Chimeric Plant Viruses Immunize Against Rables Virus and HIV–1," *Pro. Natl. Acad. Sci. USA*, 94:5784–5788 (1997).

Coppola, et al., "Characterization of glycosylated and catalytically active recombinant human alpha-galactosidase A using a baculovirus vector", *Gene* 144(2): 197–203, 1994.

Murray, et al., "Production of recombinant human glucocerebrosidase in plants", *FASEB J.* 10(6): A1126, 1996.

* cited by examiner

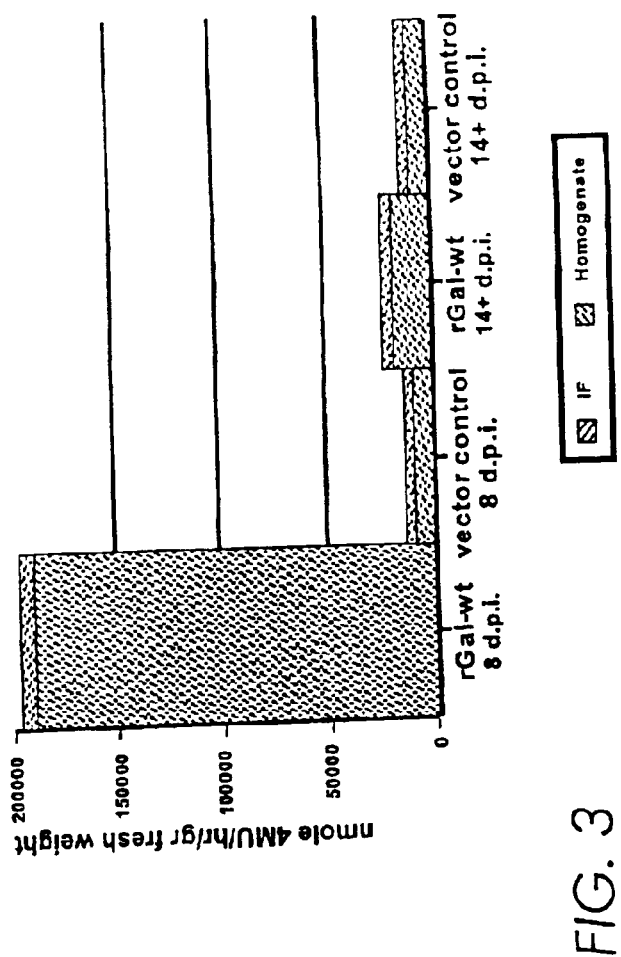
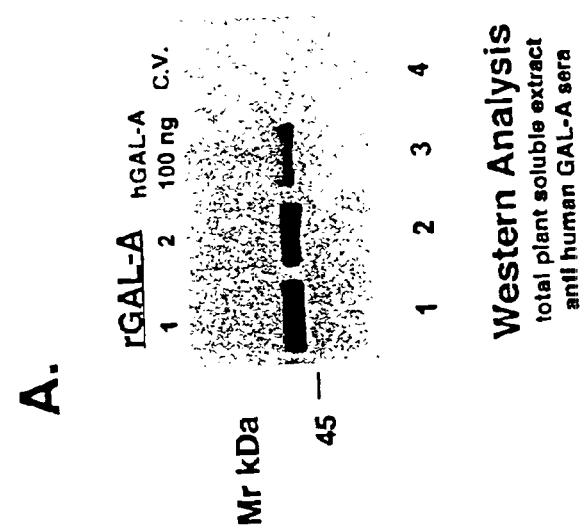
FIG. 3

Accumulation and Activity of WT and ER-Targeted rGal-A
A.
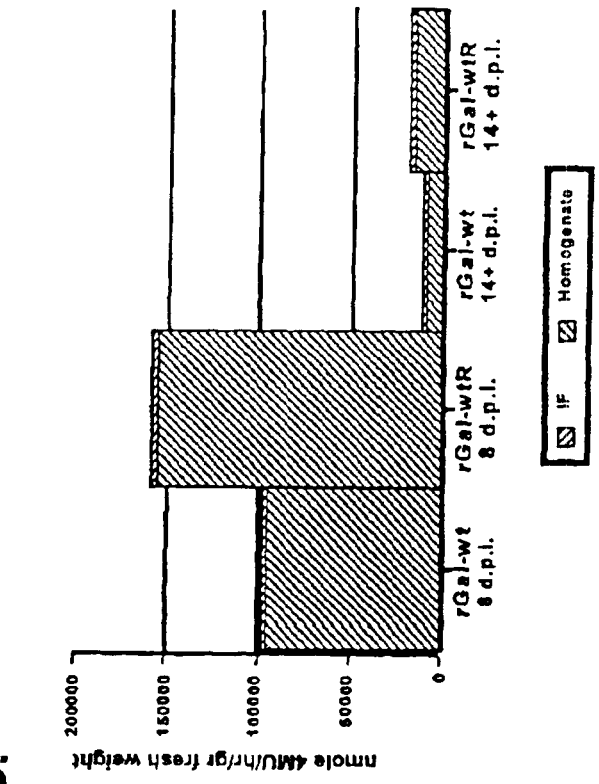
B.
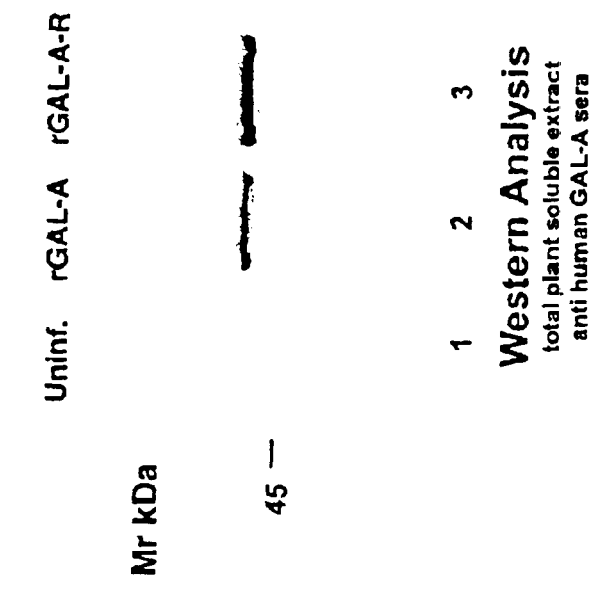
FIG. 4

FIG. 12-1

```
GTATTTTTACAACAATTACCAACAACAACAAACAACAAACAACATTACAATTACTATTTACAATTACAATGGCATACACA
CAGACAGCTACCACATCAGCTTTGCTGGACACTGTCCGAGGAAACAACTCCTTGGTCAATGATCTAGCAAAGCGTCGTCT
TTACGACACAGCGGTTGAAGAGTTTAACGCTCGTGACCGCAGGCCCAAGGTGAACTTTTCAAAAGTAATAAGCGAGGAGC
AGACGCTTATTGCTACCCGGGCGTATCCAGAATTCCAAATTACATTTTATAACACGCAAAATGCCGTGCATTCGCTTGCA
GGTGGATTGCGATCTTTAGAACTGGAATATCTGATGATGCAAATTCCCTACGGATCATTGACTTATGACATAGGCGGGAA
TTTTGCATCGCATCTGTTCAAGGGACGAGCATATGTACACTGCTGTATGCCCAACCTGGACGTTCGAGACATCATGCGGC
ACGAAGGCCAGAAACACAGTATTGAACTATACCTTTCTAGGCTAGAGAGAGGGGCGAAAACAGTCCCCAACTTCCAAAAG
GAAGCATTTGACAGATACGCAGAAATTCCTGAAGACGCTGTCTGTCACAATACTTTCCAGACAATGCGACATCAGCCGAT
GCAGCAATCAGGCAGAGTCTATGCCATTGCGCTACACAGCATATATGACATACCAGCCGATGAGTTCGGGCGGCACTCT
TGAGGAAAAATGTCCATACGTGCTATGCCGCTTTCCACTTCTCTGAGAACCTGCTTCTTGAAGATTCATACGTCAATTTG
GACGAAATCAACGCGTGTTTTTCGCGCGATGGAGACAAGTTGACCTTTTCTTTTGCATCAGAGAGTACTCTTAATTATTG
TCATAGTTATTCTAATATTCTTAAGTATGTGTGCAAAACTTACTTCCCGGCCTCTAATAGAGAGGTTTACATGAAGGAGT
TTTTAGTCACCAGAGTTAATACCTGGTTTTGTAAGTTTTCTAGAATAGATACTTTTCTTTTGTACAAAGGTGTGGCCCAT
AAAAGTGTAGATAGTGAGCAGTTTTATACTGCAATGGAAGACGCATGGCATTACAAAAAGACTCTTGCAATGTGCAACAG
CGAGAGAATCCTCCTTGAGGATTCATCATCAGTCAATTACTGGTTTCCCAAAATGAGGGATATGGTCATCGTACCATTAT
TCGACATTTCTTTGGAGACTAGTAAGAGGACGCGCAAGGAAGTCTTAGTGTCCAAGGATTTCGTGTTTACAGTGCTTAAC
CACATTCGAACATACCAGGCGAAAGCTCTTACATACGCAAATGTTTTGTCCTTTGTCGAATCGATTCGATCGAGGGTAAT
CATTAACGGTGTGACAGCGAGGTCCGAATGGGATGTGGACAAATCTTTGTTACAATCCTTGTCCATGACGTTTTACCTGC
ATACTAAGCTTGCCGTTCTAAAGGATGACTTACTGATTAGCAAGTTTAGTCTCGGTTCGAAAACGGTGTGCCAGCATGTG
TGGGATGAGATTTCGCTGGCGTTTGGGAACGCATTTCCCTCCGTGAAAGAGAGGCTCTTGAACAGGAAACTTATCAGAGT
GGCAGGCGACGCATTAGAGATCAGGGTGCCTGATCTATATGTGACCTTCCACGACAGATTAGTGACTGAGTACAAGGCCT
CTCTGTGGACATGCCTGCGCTTGACATTAGGAAGAAGATGGAAGAAACGGAAGTGATGTACAATGCACTTTCAGAGTTATCG
GTGTTAAGGGAGTCTGACAAATTCGATGTTGATGTTTTTCCCAGATGTGCCAATCTTTGGAAGTTGACCCAATGACGGC
AGCGAAGGTTATAGTCGCGGTCATGAGCAATGAGAGCGGTCTGACTCTCACATTTGAACGACCTACTGAGGCGAATGTTG
CGCTAGCTTTACAGGATCAAGAGAAGGCTTCAGAAGGTGCTTTGGTAGTTACCTCAAGAGAAGTTGAAGAACCGTCCATG
AAGGGTTCGATGGCCAGAGGAGAGTTACAATTAGCTGGTCTTGCTGGAGATCATCCGGAGTCGTCCTATTCTAAGAACGA
GGAGATAGAGTCTTTAGAGCAGTTTCATATGGCAACGGCAGATTCGTTAATTCGTAAGCAGATGAGCTCGATTGTGTACA
CGGGTCCGATTAAAGTTCAGCAAATGAAAAACTTTATCGATAGCCTGGTAGCATCACTATCTGCTGCGGTGTCGAATCTC
GTCAAGATCCTCAAAGATACAGCTGCTATTGACCTTGAAACCCGTCAAAAGTTTGGAGTCTTGGATGTTGCATCTAGGAA
GTGGTTAATCAAACCAACGGCCAAGAGTCATGCATGGGGTGTTGTTGAAACCCACGCGAGGAAGTATCATGTGGCGCTTT
TGGAATATGATGAGCAGGGTGTGGTCACATGCCGATGATTGGAGAAGAGTAGCTGTCAGCTCTGAGTCTGTTGTTTATTCC
GACATGGCGAAACTCAGAACTCTGCGCAGACTGCTTCGAAACGGAGAACCGCATGTCAGTAGCGCAAAGGTTGTTCTTGT
GGACGGAGTTCCGGCCTGTGGGAAAACCAAAGAAATTCTTTCCAGGGTTAATTTTGATGAAGATCTAATTTTAGTACCTG
GGAAGCAAGCCGCGGAAATGATCAGAAGACGTGCGAATTCCTCAGGGATTATTGTGGCCACGAAGGACAACGTTAAAACC
GTTGATTCTTTCATGATGAATTTTGGGAAAAGCACACGCTGTCAGTTCAAGAGGTTATTCATTGATGAAGGGTTGATGTT
GCATACTGGTTGTGTTAATTTTCTTGTGGCGATGTCATTGTGCGAAATTGCATATGTTTACGGAGACACACAGCAGATTC
CATACATCAATAGAGTTTCAGGATTCCCGTACCCCGCCCATTTTGCCAAATTGGAACTTGACGAGGTGGAGACACGCAGA
ACTACTCTCCGTTGTCCAGCCGATGTCACACATTATCTGAACAGGAGATATGAGGGCTTTGTCATGAGCACTTCTTCGGT
TAAAAAGTCTGTTTCGCAGGACATGGTCGCGGAGCCGCCGTGATCAATCCGATCTCAAAACCCTTGCATGGCAAGATCC
TGACTTTTACCCAATCGGATAAAGAAGCTCTGCTTTCAAGAGGGTATTCAGATGTTCACACTGTGCATGAAGTGCAAGGC
GAGACATACTCTGATGTTTCACTAGTTAGGTTAACCCCTACACCAGTCTCCATCATTGCAGGAGACAGCCCACATGTTTT
GGTCGCATTGTCAAGGCACACCTGTTCGCTCAAGTACTACACTGTTGTTATGGATCCTTTAGTTAGTATCATTAGAGATC
TAGAGAAACTTAGCTCGTACTTGTTAGATATGTATAAGGTCGATCGAGGAACACAATAGCAATTACAGATTGACTCGGTG
TTCAAAGGTTCCAATCTTTTTGTTGCAGCGCCAAAGACTGGTGATATTTCTGATATGCAGTTTTACTATGATAAGTGTCT
CCCAGGCAACAGCACCATGATGAATAATTTTGATGCTGTTACCATGAGGTTGACTGACATTTCATTGAATGTCAAAGATT
GCATATTGGATATGTCTAAGTCTGTTGCTGCGCCTAAGGATCAAATCAAACCACTAATACCTATGGTACGAACGGCGGCA
GAAATGCCACGCCAGACTGGACTATTGGAAAATTTAGTGGCGATGATTAAAAGGAACTTTAACGCACCCGAGTTGTCTGG
CATCATTGATATTGAAAATACTGCCATCTTTAGTTGTAGATAAGTTTTTTGATAGTTATTTGCTTAAAGAAAAAAGAAAAC
CAAATAAAAATGTTTCTTTGTTCAGTAGAGAGTCTCTCAATAGATGGTTAGAAAAGCAGGAACAGGTAACAATAGGCCAG
CTCGCAGATTTTGATTTTGTAGATTTGCCAGCAGTTGATCAGTACAGACACATGATTAAAGCACAACCCAAGCAAAAATT
GGACACTTCAATCCAAACGGAGTACCCGGCTTTGCAGACGATTGTGTACCATTCAAAAAAGATCAATGCAATATTTGCC
CCGTTGTTTAGTGAGCTTACTAGGCAATTACTGGACAGTGTTGATTCGAGCAGATTTTTGTTTTTCACAAGAAAGACACCA
GCGCAGATTGAGGATTTCTTCGGAGATCTCGACAGTCATGTGCCGATGGATGTCTTGGAGCTGGATATATCAAAATACGA
```

FIG. 12-2

```
CAAATCTCAGAATGAATTCCACTGTGCAGTAGAATACGAGATCTGGCGAAGATTGGGTTTTGAAGACTTCTTGGGAGAAG
TTTGGAAACAAGGGCATAGAAAGACCACCCTCAAGGATTATACCGCAGGTATAAAAACTTGCATCTGGTATCAAAGAAAG
AGCGGGGACGTCACGACGTTCATTGGAAACACTGTGATCATTGCTGCATGTTTGGCCTCGATGCTTCCGATGGAGAAAAT
AATCAAAGGAGCCTTTTGCGGTGACGATAGTCTGCTGTACTTTCCAAAGGGTTGTGAGTTTCCGGATGTGCAACACTCCG
CGAATCTTATGTGGAATTTTGAAGCAAAACTGTTTAAAAAAACAGTATGGATACTTTTGCGGAAGATATGTAATACATCAC
GACAGAGGATGCATTGTGTATTACGATCCCCTAAAGTTGATCTCGAAACTTGGTGCTAAACACATCAAGGATTGGGAACA
CTTGGAGGAGTTCAGAAGGTCTCTTTGTGATGTTGCTGTTTCGTTGAACAATTGTGCGTATTACACACAGTTGGACGACG
CTGTATGGGAGGTTCATAAGACCGCCCCTCCAGGTTCGTTTGTTTATAAAAGTCTGGTGAAGTATTTGTCTCGATAAAGTT
CTTTTTAGAAGTTTGTTTATAGATGGCTCTAGTTGTTAAAGGAAAAGTGAATATCAATGAGTTTATCGACCTGACAAAAA
TGGAGAAGATCTTACCGTCGATGTTTACCCCTGTAAAGAGTGTTATGTGTTCCAAAGTTGATAAAATAATGGTTCATGAG
AATGAGTCATTGTCAGAGGTGAACCTTCTTAAAGGAGTTAAGCTTATTGATAGTGGATACGTCTGTTTAGCCGGTTTGGT
CGTCACGGGCGAGTGGAACTTGCCTGACAATTGCAGAGGAGGTGTGAGCGTGTGTCTGGTGGACAAAAGGATGGAAAGAG
CCGACGAGGCCACTCTCGGATCTTACTACACAGCAGCTGCAAAGAAAAGATTTCAGTTCAAGGTCGTTCCCAATTATGCT
ATAACCACCCAGGACGCGATGAAAAACGTCTGGCAAGTTTTAGTTAATATTAGAAATGTGAAGATGTCAGCGGGTTTCTG
TCCGCTTTCTCTGGAGTTTGTGTCGGTGTGTATTGTTTATAGAAATAATATAAAATTAGGTTTGAGAGAGAAGATTACAA
ACGTGAGAGACGGAGGGCCCATGGAACTTACAGAAGAAGTCGTTGATCAGTTCATGGAAGATGTCCCTATGTCGATCAGG
CTTGCAAAGTTTCGATCTCGAACCGGAAAAAAGAGTGATGTCCGCAAAGGGAAAAATAGTAGTAATGATCGGTCAGTGCC
GAACAAGAACTATAGAAATGTTAAGGATTTTGGAGGAATGAGTTTTAAAAAGAATAATTTAATCGATGATGATTCGGAGG
CTACTGTCGCCGAATCGGATTCGTTTTAAATAGATCTTACAGTATCACTACTCCATCTCAGTTCGTGTTCTTGTCATTAA
TATGCAGGTGCTGAACACCATGGTGAACAAACACTTCTTGTCCCTTTCGGTCCTCATCGTCCTCCTTGGCCTCTCCTCCA
ACTTGACAGCCCGGCATGCTGGACAATGGATTGGCAAGGACGCCTACCATGGGCTGGCTGCACTGGGAGCGCTTCATGTGC
AACCTTGACTGCCAGGAAGAGCCAGATTCCTGCATCAGTGAGAAGCTCTTCATGGAGATGGCAGAGCTCATGGTCTCAGA
AGGCTGGAAGGATGCAGGTTATGAGTACCTCTGCATTGATGACTGTTGGATGGCTCCCCAAAGAGATTCAGAAGGCAGAC
TTCAGGCAGACCCTCAGCGCTTTCCTCATGGGATTCGCCAGCTAGCTAATTATGTTCACAGCAAAGGACTGAAGCTAGGG
ATTTATGCAGATGTTGGAAATAAAACCTGCGCAGGCTTCCCTGGGAGTTTTGGATACTACGACATTGATGCCCAGACCTT
TGCTGACTGGGGAGTAGATCTGCTAAAATTTGATGGTTGTTACTGTGACAGTTTGGAAAATTTGGCAGATGGTTATAAGC
ACATGTCCTTGGCCCTGAATAGGACTGGCAGAAGCATTGTGTACTCCTGTGAGTGGCCTCTTTATATGTGCCCCTTTCAA
AAGCCCAATTATACAGAAATCCGACAGTACTGCAATCACTGGCGAAATTTTGCTGACATTGATGATTCCTGGAAAAGTAT
AAAGAGTATCTTGGACTGGACATCTTTTAACCAGGAGAGAATTGTTGATGTTGCTGGACCAGGGGGTTGGAATGACCCAG
ATATGTTAGTGATTGGCAACTTTGGCCCTCAGCTGGAATCAGCAAGTAACTCAGATGGCCCTCTGGGCTATCATGGCTGCT
CCTTTATTCATGTCTAATGACCTCCGACACATCAGCCCTCAAGCCAAAGCTCTCCTTCAGGATAAGGACGTAATTGCCAT
CAATCAGGACCCCTTGGGCAAGCAAGGGTACCAGCTTAGACAGGGAGACAACTTTGAAGTGTGGGAACGACCTCTCTCAG
GCTTAGCCTGGGCTGTAGCTATGATAAACCGGCAGGAGATTGGTGGACCTCGCTCTTATACCATCGCAGTTGCTTCCCTG
GGTAAAGGAGTGGCCTGTAATCCTGCCTGCTTCATCACACAGCTCCTCCCTGTGAAAAGGAAGCTAGGGTTCTATGAATG
GACTTCAAGGTTAAGAAGTCACATAAATCCCACAGGCACTGTTTTGCTTCAGCTAtctgaaaaggacgaattatgaCCTA
GGCTCGCAAAGTTTCGAACCAAATCCTCAAAAAGAGGTCCGAAAAATAATAATAATTTAGGTAAGGGGCGTTCAGGCGGA
AGGCCTAAACCAAAAAGTTTTGATGAAGTTGAAAAAGAGTTTGATAATTTGATTGAAGATGAAGCCGAGACGTCGGTCGC
GGATTCTGATTCGTATTAAATATGTCTTACTCAATCACTTCTCCATCGCAATTTGTGTTTTTGTCATCTGTATGGGCTGA
CCCTATAGAATTGTTAAACGTTTGTACAAATTCGTTAGGTAACCAGTTTCAAACACAGCAAGCAAGAACTACTGTTCAAC
AGCAGTTCAGCGAGGTGTGGAAACCTTTCCCTCAGAGCACCGTCAGATTTCCTGGCGATGTTTATAAGGTGTACAGGTAC
AATGCAGTTTTAGATCCTCTAATTACTGCGTTGCTGGGGGCTTTTGATACTAGGAATAGAATAATCGAAGTAGAAAACCA
GCAGAGTCCGACAACAGCTGAAACGTTAGATGCTACCCGCAGGGTAGACGACGCTACGGTTGCAATTCGGTCTGCTATAA
ATAATTTAGTTAATGAACTAGTAAGAGGTACTGGACTGTACAATCAGAATACTTTTGAAAGTATGTCTGGGTTGGTCTGG
ACCTCTGCACCTGCATCTTAAATGCATAGGTGCTGAAATATAAAGTTTGTGTTTCTAAAACACACGTGGTACGTACGATA
ACGTACAGTGTTTTTCCCTCCACTTAAATCGAAGGGTAGTGTCTTGGAGCGCGCGGAGTAAACATATATGGTTCATATAT
GTCCGTAGGCACGTAAAAAAAGCGAGGGATTCGAATTCCCCCGGAACCCCCGGTTGGGGCCCAGGTACCAATTCTTGAAG
ACGAAAGGGCCTCGTGATACCCCTATTTTTATAGGTTAATGTCATGATAATAATGGTTTCTTAGACGTCAGGTGGCACTT
TTCGGGGAAATGTGCGCGGAACCCCTATTTGTTTATTTTTCTAAATACATTCAAATATGTATCCGCTCATGAGACAATAA
CCCTGATAAATGCTTCAATAATATTGAAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGCTGAAGATCAGTTGGGTGCAC
GAGTGGGTTACATCGAACTGGATCTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTGTTGACGCCGGGCAAGAGCAACTCGGTCGCCGCATACA
CTATTCTCAGAATGACTTGGTTGAGTACTCACCAGTCACAGAAAAGCATCTTACGGATGGCATGACAGTAAGAGAATTAT
```

FIG. 12-3

```
GCAGTGCTGCCATAACCATGAGTGATAACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGGAGCTGAATGAAGCCATACCAAACGA
CGAGCGTGACACCACGATGCCTGCAGCAATGGCAACAACGTTGCGCAAACTATTAACTGGCGAACTACTTACTCTAGCTT
CCCGGCAACAATTAATAGACTGGATGGAGGCGGATAAAGTTGCAGGACCACTTCTGCGCTCGGCCCTTCCGGCTGGCTGG
TTTATTGCTGATAAATCTGGAGCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGATTTAAAACTTCATTTTTAATTT
AAAAGGATCTAGGTGAAGATCCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACTGGCTTCAGCAGAGCG
CAGATACCAAATACTGTCCTTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGGGTTGGACTCAAGACGATAGT
TACCGGATAAGGCGCAGCGGTCGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGCGGAGCCTATGGAAAAACGCCAGCAACGCGGCCTTT
TTACGGTTCCTGGCCTTTTGCTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGTCAGTGAGCGAGGAAGCGGAAG
AGCGCCTGATGCGGTATTTTCTCCTTACGCATCTGTGCGGTATTTCACACCGCATATGGTGCACTCTCAGTACAATCTGC
TCTGATGCCGCATAGTTAAGCCAGTATACACTCCGCTATCGCTACGTGACTGGGTCATGGCTGCGCCCCGACACCCGCCA
ACACCCGCTGACGCGCCCTGACGGGCTTGTCTGCTCCCGGCATCCGCTTACAGACAAGCTGTGACCGTCTCCGGGAGCTG
CATGTGTCAGAGGTTTTCACCGTCATCACCGAAACGCGCGAGGCAGCTGCGGTAAAGCTCATCAGCGTGGTCGTGAAGCG
ATTCACAGATGTCTGCCTGTTCATCCGCGTCCAGCTCGTTGAGTTTCTCCAGAAGCGTTAATGTCTGGCTTCTGATAAAG
CGGGCCATGTTAAGGGCGGTTTTTTCCTGTTTGGTCACTTGATGCCTCCGTGTAAGGGGGAATTTCTGTTCATGGGGGTA
ATGATACCGATGAAACGAGAGAGGATGCTCACGATACGGGTTACTGATGATGAACATGCCCGGTTACTGGAACGTTGTGA
GGGTAAACAACTGGCGGTATGGATGCGGCGGGACCAGAGAAAAATCACTCAGGGTCAATGCCAGCGCTTCGTTAATACAG
ATGTAGGTGTTCCACAGGGTAGCCAGCAGCATCCTGCGATGCAGATCCGGAACATAATGGTGCAGGGCGCTGACTTCCGC
GTTTCCAGACTTTACGAAACACGGAAACCGAAGACCATTCATGTTGTTGCTCAGGTCGCAGACGTTTTGCAGCAGCAGTC
GCTTCACGTTCGCTCGCGTATCGGTGATTCATTCTGCTAACCAGTAAGGCAACCCCGCCAGCCTAGCCGGGTCCTCAACG
ACAGGAGCACGATCATGCGCACCCGTGGCCAGGACCCAACGCTGCCCGAGATGCGCCGCGTGCGGCTGCTGGAGATGGCG
GACGCGATGGATATGTTCTGCCAAGGGTTGGTTTGCGCATTCACAGTTCTCCGCAAGAATTGATTGGCTCCAATTCTTGG
AGTGGTGAATCCGTTAGCGAGGTGCCGCCGGCTTCCATTCAGGTCGAGGTGGCCCGGCTCCATGCACCGCGACGCAACGC
GGGGAGGCAGACAAGGTATAGGGCGGCGCCTACAATCCATGCCAACCCGTTCCATGTGCTCGCCGAGGCGGCATAAATCG
CCGTGACGATCAGCGGTCCAGTGATCGAAGTTAGCCTGGTAAGAGCCGCGAGCGATCCTTGAAGCTGTCCCTGATGGTCG
TCATCTACCTGCCTGGACAGCATGGCCTGCAACGCGGGCATCCCGATGCCGCCGGAAGCGAGAAGAATCATAATGGGGAA
GGCCATCCAGCCTCGCGTCGCGAACGCCAGCAAGACGTAGCCCAGCGCGTCGGCCGCCATGCCGGCGATAATGGCCTGCT
TCTCGCCGAAACGTTTGGTGGCGGGACCAGTGACGAAGGCTTGAGCGAGGGCGTGCAAGATTCCGAATACCGCAAGCGAC
AGGCCCGATCATCGTCGCGCTCCAGCGAAAGCGGTCCTCGCCGAAAATGACCCAGAGCGCTGCCGGCACCTGTCCTACGAG
TTGCATGATAAAGAAGACAGTCATAAGTGCGGCGACGATAGTCATGCCCCGCGCCCACCGGAAGGAGCTGACTGGGTTGA
AGGCTCTCAAGGGCATCGGTCGAGATTTAGGTGACACTATA
```

FIG. 13-1

```
GTATTTTTACAACAATTACCAACAACAACAAACAACAGACAACATTACAATTACTATTTACAATTACAATGGCATACACA
CAGACAGCTACCACATCAGCTTTGCTGGACACTGTCCGAGGAAACAACTCCTTGGTCAATGATCTAGCAAAGCGTCGTCT
TTACGACACAGCGGTTGAAGAGTTTAACGCTCGTGACCGCAGGCCCAAGGTGAACTTTTCAAAAGTAATAAGCGAGGAGC
AGACGCTTATTGCTACCCGGGCGTATCCAGAATTCCAAATTACATTTTATAACACGCAAAATGCCGTGCATTCGCTTGCA
GGTGGATTGCCGATCTTTAGAACTGGAATATCTGATGATGCAAATTCCCTACGGATCATTGACTTATGACATAGGCGGGAA
TTTTGCATCGCATCTGTTCAAGGGACGAGCATATGTACACTGCTGCATGCCCAACCTGGACGTTCGAGACATCATGCGGC
ACGAAGGCCAGAAAGACAGTATTGAACTATACCTTTCTAGGCTAGAGAGAGGCGGGAAAACAGTCCCCAACTTCCAAAAG
GAAGCATTTGACAGATACGCAGAAATTCCTGAAGACGCTGTCTGTCACAATACTTTCCAGACATGCGAACATCAGCCGAT
GCAGCAATCAGGCAGAGTGTATGCCATTGCGCTACACAGCATATATGACATACCAGCCGATGAGTTCGGGGCGGCACTCT
TGAGGAAAAATGTCCATACGTGCTATGCCGCTTTCCACTTCTCCGAGAACCTGCTTCTTGAAGATTCATGCGTCAATTTG
GACGAAATCAACGCGTGTTTTTCGCGCGATGGAGACAAGTTGACCTTTTCTTTTGCATCAGAGAGTACTCTTAATTACTG
TCATAGTTATTCTAATATTCTTAAGTATGTGTGCAAAACTTACTTCCCGGCCTCTAATAGAGAGGTTTACATGAAGGAGT
TTTTAGTCACCAGAGTTAATACCTGGTTTTGTAAGTTTTCTAGAATAGATACTTTTCTTTTGTACAAAGGTCTGGCCCAT
AAAAGTGTAGATAGTGAGCAGTTTTATACTGCAATGGAAGACGCATGGCATTACAAAAAGACTCTTGCAATGTGCAACAG
CGAGAGAATCCTCCTTGGGGATTCATCATCAGTCAATTACTGGTTTCCCAAAATGAGCGATATGGTCATCGTACCATTAT
TCGACATTTCTTTGGAGACTAGTAAGAGGACGCGCAAGGAAGTCTTAGTGTCCAAGGATTTCGTGTTCACAGTGCTTAAC
CACATTCGAACATACCAGGCGAAAGCTCTTACATACGCAAATGTTTTGTCCTTCGTCGAATCGATTCGATCGAGGGTAAT
CATTAACGGTGTGACAGCGAGGTCCGAATGGGATGTGGACAAATCTTTGTTACAATCCTTGTCCATGACGTTTTACCTGC
ATACTAAGCTTGCCGTTCTAAAGGATGACTTACTGATTAGCAAGTTTAGTCTCGGTTCGAAAACGGTGTGCCAGCATGTG
TGGGATGAGATTTCGCTGGCGTTTGGGAACGCATTTCCCTCCGTGAAAGAGAGGCTCTTGAACAGGAAACTTATCAGAGT
GGCAGGCGACGCATTAGAGATCAGGGTGCCTGATCTATATGTGACCTTCCACGACAGATTAGTGACTGAGTACAAGGCCT
CTGTGGACATGCCTGCGCTTGACATTAGGAAGAAGATGGAAGAAACGGAAGTGATGTACAATGCACTTTCAGAATTATCG
GTGTTAAGGGAGTCTGACAAATTCGATGTTGATGTTTTTTCCCAGATGTGCCAATCTTTGGAAGTTGACCCAATGACGGC
AGCGAAGGTTATAGTCGCGGTCATGAGCAATGAGAGCGGTCTGACTCTCACATTTGAACGACCTACTGAGGCGAATGTTG
CGCTAGCTTTACAGGATCAAGACAAGGCTTCAGAAGGTGCATTGGTAGTTACCTCAAGAGAAGTTGAAGAACCGTCCATG
AAGGGTTCGATGCCCAGAGGAGAGTTACAATTAGCTGGTCTTGCTGGAGATCATCCGGAATCGTCCTATTCTAAGAACGA
GGAGATAGAGTCTTTAGAGCAGTTTCATATGGCGACGGCAGATTCGTTAATTCGTAAGCAGATGAGCTCGATTGTGTACA
CGGGTCCGATTAAAGTTCAGCAAATGAAAAACTTTATCGATAGCCTGGTAGCATCACTATCTGCTGCGGTGTCGAATCTC
GTCAAGATCCTCAAAGATACAGCTGCTATTGACCTTGAAACCCGTCAAAAGTTTGGAGTCTTGGATGTTGCATCTAGGAA
GTGGTTAATCAAACCAACGGCCAAGAGTCATGCATGGGGTGTTGTTGAAACCCACGCGAGGGAGTATCATGTGGCGCTTT
TGGAATATGATGAGCAGGGTGTGGTGACATGCGATGATTGGAGAAGAGTAGCTGTTAGCTCTGAGTCTGTTGTTTATTCC
GACATGGCGAAACTCAGAACTCTGCGCAGACTGCTTCGAAACGGAGAACCGCATGTCAGTAGCGCAAAGGTTGTTCTTGT
GGACGGAGTTCCGGGCTGTGGAAAAAACCAAAGAAATTCTTTCCAGGGTTAATTTTGATGAAGATCTAATTTTAGTACCTG
GGAAGCAAGCCGCGGAAATGATCAGAAGACGTGCGAATTCCTCAGGGATTATTGTGGCCACGAAGGACAACGTTAAAACC
GTTGATTCTTTCATGATGAATTTTGGGAAAAGCACACGCTGTCAGTTCAAGAGGTTATTCATTGATGAAGGGTTGATGTT
GCATACTGGTTGTGTTAATTTTCTTGTGGCCGATGTCATTGTGCGAAATTGCATATGTTTACGGAGACACACAGCAGATTC
CATACATCAATAGAGTTTCAGGATTCCCGTACCCCGCCCATTTTGCCAAATTGGAAGTTGACGAGGTGGAGACACGCAGA
ACTACTCTCCGTTGTCCAGCCCGATGTCACACATTATCTGAACAGGAGATATGAGGGCTTTGTCATGAGCACTTCTTCGGT
TAAAAAGTCTGTTTCGCAGGAGATGGTCGGCGGAGCCGCCCGTGATCAATCCGATCTCAAAACCCTTGCATGGCAAGATCC
TGACTTTTACCCAATCGGATAAAGAAGCTCTGCTTTCAAGAGGGTATTCAGATGTTCACACTGTGCATGAAGTGCAAGGC
GAGACATACTCTGATGTTTCACTAGTTAGGTTAACCCCTACACCGGTCTCCATCATTGCAGGAGACAGCCCACATGTTTT
GGTCGCATTGTCAAGGCACACCTGTTCGCTCAAGTACTACACTGTTGTTATGGATCCTTTAGTTAGTATCATTAGAGATC
TAGAGAAACTTAGCTCGTACTTGTTAGATATGTATAAGGTCGATGCAGGAACACAATAGCAATTACAGATTGACTCGGTG
TTCAAAGGTTCCAATCTTTTTGTTGCAGCGCCAAAGACTGGTGATATTTCTGATATGCAGTTTTACTATGATAAGTGTCT
CCCAGGCAACAGCACCATGATGAATAATTTTGATGCTGTTACCATGAGGTTGACTGACATTTCATTGAATGTCAAAGATT
GCATATTGGATATGTCTAAGTCTGTTGCTGCACCTAAGGATCAAATCAAACCACTAATACCTATGGTACGAACGGCGGCA
GAAATGCCACGCCAGACTGGACTATTGGAAAATTTAGTGGCGATGATTAAAAGAAACTTTAACGCACCCGAGTTGTCTGG
CATCATTGATATTGAAAATACTGCATCTTTGGTTGTAGATAAGTTTTTTTGATAGTTATTTGCTTAAAGAAAAAAGAAAAC
CAAATAAAAATGTTTCTTTGTTCAGTAGAGAGTCTCTCAATAGATGGTTAGAAAAGCAGGAACAGGTAACAATAGGCCAG
CTCGCAGATTTTGATTTTGTGGATTTGCCAGCAGTTGATCAGTACAGACACATGATTAAAGCACAACCCAAACAAAAGTT
GGACACTTCAATCCAAACGGAGTACCCGGCTTTGCAGACGATTGTGTACCATTCAAAAAAGATCAATGCAATATTCGGCC
CGTTGTTTAGTGAGCTTACTAGGCAATTACTGGACAGTGTTGATTCGAGCAGATTTTTGTTTTTCACAAGAAAGACACCA
GCGCAGATTGAGGATTTCTTCGGAGATCTCGACAGTCATGTGCCGATGGATGTCTTGGAGCTGGATATATCAAAATACGA
```

FIG. 13-2

```
CAAATCTCAGAATGAATTCCACTGTGCAGTAGAATACGAGATCTGGCGAAGATTGGGTTTCGAAGACTTCTTGGGAGAAG
TTTGGAAACAAGGGCATAGAAAGACCACCCTCAAGGATTATACCGCAGGTATAAAAACTTGCATCTGGTATCAAAGAAAG
AGCGGGGACGTCACGACGTTCATTGGAAACACTCTGATCATTGCTGCATGTTTGGCCTCGATGCTTCCGATGGAGAAAAT
AATCAAAGGAGCCTTTTGCCGGTGACGTAGTCTGCTGTACTTTCCAAAGGGTTGTGAGTTTCCGGATGTGCAACACTCCG
CGAATCTTATGTGGAATTTTGAAGCAAAACTGTTTAAAAAACAGTATGGATACTTTTGCGGAAGATATGTAATACATCAC
GACAGAGGATGCATTGTGTATTACGATCCCCTAAAGTTGATCTCGAAACTTGGTGCTAAACACATCAAGGATTGGGAACA
CTTGGAGGAGTTCAGAAGGTCTCTTTGTGATGTTGCTGTTTCGTTGAACAATTGTGCGTATTACACACAGTTGGACGACG
CTGTATGGGAGGTTCATAAGACCGCCCCTCCAGGTTCGTTTGTTTATAAAAGTCTGGTGAAGTATTTGTCTGATAAAGTT
CTTTTTAGAAGTTTGTTTATAGATGGCTCTAGTTGTTAAAGGAAAAGTGAATATCAATGAGTTTATCGACCTGACAAAAA
TGGAGAAGATCTTACCGTCGATGTTTACCCCTGTAAAGAGTGTTATGTGTTCCAAAGTTGATAAAATAATGGTTCATGAG
AATGAGTCATTGTCAGGGGTGAACCTTCTTAAAGGAGTTAAGCTTATTGATAGTGGATACGTCTGTTTAGCCGGTTTGGT
CGTCACGGGCGAGTGGAACTTGCCTGACAATTGCAGAGGAGGTGTGAGCGTGTGTCTGGTGGACAAAAGGATGGAAAGAG
CCGACGAGGCCATTCTCGGATCTTACTACACAGCAGCTGCAAAGAAAAGATTTCAGTTCAAGGTCGTTCCCAATTATGCT
ATAACCACCCAGGACGCGATGAGAAACGTCTGGCAAGTTTTAGTTAATATTAGAAATGTGAAGATGTCAGCGGGTTTCTG
TCCGCTTTCTCTGGAGTTTGTGTCGGTGTGTATTGTTTATAGAAATAATATAAAATTAGGTTTGAGAGAGAAGATTACAA
ACGTGAGAGACGCAGGGCCCATGGAACTTACAGAAGAAGTCGTTGATGAGTTCATGGAAGATGTCCCTATGTCGATCAGG
CTTGCAAAGTTTCGATCTCGAACCGGAAAAAAGAGTGATGTCCGCAAAGGGAAAAATAGTAGTAGTGATCGGTCAGTGCC
GAACAACAACTATAGAAATGTTAAGGATTTTGGAGGAATGAGTTTTAAAAAGAATAATTTAATCGATGATGATTCGGAGG
CTACTGTCGCCGAATCGGATTCGTTTTAAATAGATCTTACAGTATCACTACTCCATCTCAGTTCGTGTTCTTGTCAttaa
ttaaaatgcagctgaggaacccagaactacatctgggctgcgcgcttgcgcttcgcttcctggccctcgtttcctgggac
atccctggggctagagcactggacaatggattggcaaggacgcctaccatgggctggctgcactgggagcgcttcatgtg
caaccttgactgccaggaagagccagattcctgcatcagtgagaagctcttcatggagatggcagagctcatggtctcag
aaggctggaaggatgcaggttatgagtacctctgcattgatgactgttggatggctccccaaagagattcagaaggcaga
cttcaggcagaccctcagcgctttcctcatgggattcgccagctagctaattatgttcacagcaaaggactgaagctagg
gatttatgcagatgttggaaatgaaacctgcgcaggcttccctggggagttttggatactacgacattgatgcccagacct
tgctgactggggagtagatctgctaaaatttgatggttgttactgtgacagtttggaaaatttggcagatggttataag
cacatgtccttggccctgaataggactggcagaagcattgtgtactcctgtgagtggcctctttatatgtggccctttca
aaagcccaattatacagaaatccgacagtactgcaatcactggcgaaattttgctgacattgatgattcctggaaaagta
taaagagtatcttggactggacatcttttaaccaggagagaattgttgatgttgctggaccaggggggttggaatgaccca
gatatgttagtgattggcaactttggcctcagctggaatcagcaagtaactcagatggccctctgggctatcatggctgc
tcctttattcatgtctaatgacctccgacacatcagccctcaagccaaagctctccttcaggataaggacgtaattgcca
tcaatcaggacccccttgggcaagcaagggtaccagcttagacagggagacaactttgaagtgtgggaacgacctctctca
ggcttagcctgggctgtagctatgataaaccggcaggagattggtggacctcgctcttataccatcgcagttgcttccct
gggtaaaggagtggcctgtaatcctgcctgcttcatcacacagctcctccctgtgaaaaggaagctagggttctatgaat
ggacttcaaggttaagaagtcacataaatcccacaggcactgttttgcttcagctatctgaaaaggacgaattatgacct
aggGGGTAGTCAAGATGCATAATAAATAACGGATTGTGTCCGTAATCACACGTGGTGCGTACGATAACGCATAGTGTTTT
TCCCTCCACTTAAATCGAAGGGTTGTGTCTTGGATCGCGCGGGTCAAATGTATATGGTTCATATACATCCGCAGGCACGT
AATAAAGCGAGGGGTTCGGGTCGAGGTCGGCTGTGAAACTCGAAAAGGTTCCGGAAAACAAAAAAGAGAGTGGTAGGTAA
TAGTGTTAATAATAAGAAAATAAATAATAGTGGTAAGAAAGGTTTGAAAGTTGAGGAAATTGAGCGATAATGTAAGTGATG
ACGAGTCTATCGCGTCATCGAGTACGTTTTAATCAATATGCCTTATACAATCAACTCTCCGAGCCAATTTGTTTACTTAA
GTTCCGCTTATGCAGATCCTGTGCAGCTGATCAATCTGTGTACAAATGCATTGGGTAACCAGTTTCAAACGCAACAAGCT
AGGACAACAGTCCAACAGCAATTTGCGGATGCCTGGAAACCTGTGCCTAGTATGACAGTGAGATTTCCTGCATCGGATTT
CTATGTGTATAGATATAATTCGACGCTTGATCCGTTGATCACGGCGTTATTAAATAGCTTCGATACTAGAAATAGAATAA
TAGAGGTTGATAATCAACCCGCACCGAATACTACTGAAATCGTTAACGCGACTCAGAGGGTAGACGATGCGACTGTAGCT
ATAAGGGCTTCAATCAATAATTTGGCTAATGAACtGGTTCGTGGAACTCGCaTGTTCAATCAAGCAAGCTTTGAGACTGC
TAGTCGACTTGTCTGGACCACAACTCCGGCTACTTAGctattgttgtgagatttcctaaaataaagtcactgaagactta
aaattcagggtggctgataccaaaatcagcagtggttgttcgtccacttaaatataacgattgtcatatctggatccaac
agttaaaccatgtgatggtgtatactgtggtatggcgtaaaacaacggaaaagtcgctgaagacttaaaattcagggtgg
ctgataccaaaatcagcagtggttgttcgtccacttaaaaataacgattgtcatatctggatccaacagttaaaccatgt
gatggtgtatactgtggtatggcgtaaaacaacggagaggttcgaatcctcccctaaccgcgggtagcggccca
```

TRANSGENIC VECTOR FOR rGCB EXPRESSION

SEQUENCE LISTING

<160> NUMBER OF SEQ ID NOS: 37

<210> SEQ ID NO 1
<211> LENGTH: 15
<212> TYPE: PRT
<213> ORGANISM: Rice

<400> SEQUENCE: 1

Ser Asn Leu Thr Ala Gly Met Leu Asp Asn Gly Leu Ala Arg Thr

-continued

<210> SEQ ID NO 2
<211> LENGTH: 15
<212> TYPE: PRT
<213> ORGANISM: Homo sapiens

<400> SEQUENCE: 2

Asp Ile Pro Gly Ala Arg Ala Leu Asp Asn Gly Leu Ala Arg Thr
 1               5                   10                  15

<210> SEQ ID NO 3
<211> LENGTH: 1290
<212> TYPE: DNA
<213> ORGANISM: Homo sapiens
<220> FEATURE:
<221> NAME/KEY: CDS
<222> LOCATION: (1)...(1290)

<400> SEQUENCE: 3

```
atg cag ctg agg aac cca gaa cta cat ctg ggc tgc gcg ctt gcg ctt     48
Met Gln Leu Arg Asn Pro Glu Leu His Leu Gly Cys Ala Leu Ala Leu
 1               5                   10                  15
cgc ttc ctg gcc ctc gtt tcc tgg gac atc cct ggg gct aga gca ctg     96
Arg Phe Leu Ala Leu Val Ser Trp Asp Ile Pro Gly Ala Arg Ala Leu
             20                  25                  30
gac aat gga ttg gca agg acg cct acc atg ggc tgg ctg cac tgg gag    144
Asp Asn Gly Leu Ala Arg Thr Pro Thr Met Gly Trp Leu His Trp Glu
         35                  40                  45
cgc ttc atg tgc aac ctt gac tgc cag gaa gag cca gat tcc tgc atc    192
Arg Phe Met Cys Asn Leu Asp Cys Gln Glu Glu Pro Asp Ser Cys Ile
     50                  55                  60
agt gag aag ctc ttc atg gag atg gca gag ctc atg gtc tca gaa ggc    240
Ser Glu Lys Leu Phe Met Glu Met Ala Glu Leu Met Val Ser Glu Gly
 65                  70                  75                  80
tgg aag gat gca ggt tat gag tac ctc tgc att gat gac tgt tgg atg    288
Trp Lys Asp Ala Gly Tyr Glu Tyr Leu Cys Ile Asp Asp Cys Trp Met
                 85                  90                  95
gct ccc caa aga gat tca gaa ggc aga ctt cag gca gac cct cag cgc    336
Ala Pro Gln Arg Asp Ser Glu Gly Arg Leu Gln Ala Asp Pro Gln Arg
            100                 105                 110
ttt cct cat ggg att cgc cag cta gct aat tat gtt cac agc aaa gga    384
Phe Pro His Gly Ile Arg Gln Leu Ala Asn Tyr Val His Ser Lys Gly
        115                 120                 125
ctg aag cta ggg att tat gca gat gtt gga aat aaa acc tgc gca ggc    432
Leu Lys Leu Gly Ile Tyr Ala Asp Val Gly Asn Lys Thr Cys Ala Gly
    130                 135                 140
ttc cct ggg agt ttt gga tac tac gac att gat gcc cag acc ttt gct    480
Phe Pro Gly Ser Phe Gly Tyr Tyr Asp Ile Asp Ala Gln Thr Phe Ala
145                 150                 155                 160
gac tgg gga gta gat ctg cta aaa ttt gat ggt tgt tac tgt gac agt    528
Asp Trp Gly Val Asp Leu Leu Lys Phe Asp Gly Cys Tyr Cys Asp Ser
                165                 170                 175
ttg gaa aat ttg gca gat ggt tat aag cac atg tcc ttg gcc ctg aat    576
Leu Glu Asn Leu Ala Asp Gly Tyr Lys His Met Ser Leu Ala Leu Asn
            180                 185                 190
agg act ggc aga agc att gtg tac tcc tgt gag tgg cct ctt tat atg    624
Arg Thr Gly Arg Ser Ile Val Tyr Ser Cys Glu Trp Pro Leu Tyr Met
        195                 200                 205
tgg ccc ttt caa aag ccc aat tat aca gaa atc cga cag tac tgc aat    672
Trp Pro Phe Gln Lys Pro Asn Tyr Thr Glu Ile Arg Gln Tyr Cys Asn
    210                 215                 220
cac tgg cga aat ttt gct gac att gat gat tcc tgg aaa agt ata aag    720
His Trp Arg Asn Phe Ala Asp Ile Asp Asp Ser Trp Lys Ser Ile Lys
225                 230                 235                 240
agt atc ttg gac tgg aca tct ttt aac cag gag aga att gtt gat gtt    768
Ser Ile Leu Asp Trp Thr Ser Phe Asn Gln Glu Arg Ile Val Asp Val
                245                 250                 255
gct gga cca ggg ggt tgg aat gac cca gat atg tta gtg att ggc aac    816
Ala Gly Pro Gly Gly Trp Asn Asp Pro Asp Met Leu Val Ile Gly Asn
            260                 265                 270
ttt ggc ctc agc tgg aat cag caa gta act cag atg gcc ctc tgg gct    864
Phe Gly Leu Ser Trp Asn Gln Gln Val Thr Gln Met Ala Leu Trp Ala
        275                 280                 285
atc atg gct gct cct tta ttc atg tct aat gac ctc cga cac atc agc    912
```

```
            Ile Met Ala Ala Pro Leu Phe Met Ser Asn Asp Leu Arg His Ile Ser
                290                 295                 300
cct caa gcc aaa gct ctc ctt cag gat aag gac gta att gcc atc aat        960
Pro Gln Ala Lys Ala Leu Leu Gln Asp Lys Asp Val Ile Ala Ile Asn
305                 310                 315                 320
cag gac ccc ttg ggc aag caa ggg tac cag ctt aga cag gga gac aac       1008
Gln Asp Pro Leu Gly Lys Gln Gly Tyr Gln Leu Arg Gln Gly Asp Asn
                325                 330                 335
ttt gaa gtg tgg gaa cga cct ctc tca ggc tta gcc tgg gct gta gct       1056
Phe Glu Val Trp Glu Arg Pro Leu Ser Gly Leu Ala Trp Ala Val Ala
            340                 345                 350
atg ata aac cgg cag gag att ggt gga cct cgc tct tat acc atc gca       1104
Met Ile Asn Arg Gln Glu Ile Gly Gly Pro Arg Ser Tyr Thr Ile Ala
        355                 360                 365
gtt gct tcc ctg ggt aaa gga gtg gcc tgt aat cct gcc tgc ttc atc       1152
Val Ala Ser Leu Gly Lys Gly Val Ala Cys Asn Pro Ala Cys Phe Ile
370                 375                 380
aca cag ctc ctc cct gtg aaa agg aag cta ggg ttc tat gaa tgg act       1200
Thr Gln Leu Leu Pro Val Lys Arg Lys Leu Gly Phe Tyr Glu Trp Thr
385                 390                 395                 400
tca agg tta aga agt cac ata aat ccc aca ggc act gtt ttg ctt cag       1248
Ser Arg Leu Arg Ser His Ile Asn Pro Thr Gly Thr Val Leu Leu Gln
                405                 410                 415
cta gaa aac aca atg cag atg tct tta aaa gac tta ctt taa               1290
Leu Glu Asn Thr Met Gln Met Ser Leu Lys Asp Leu Leu  *
            420                 425

<210> SEQ ID NO 4
<211> LENGTH: 428
<212> TYPE: PRT
<213> ORGANISM: Homo sapiens

<400> SEQUENCE: 4

Gln Leu Arg Asn Pro Glu Leu His Leu Gly Cys Ala Leu Ala Leu Arg
    1               5                   10                  15
    Phe Leu Ala Leu Val Ser Trp Asp Ile Pro Gly Ala Arg Ala Leu Asp
                20                  25                  30
    Asn Gly Leu Ala Arg Thr Pro Thr Met Gly Trp Leu His Trp Glu Arg
            35                  40                  45
    Phe Met Cys Asn Leu Asp Cys Gln Glu Glu Pro Asp Ser Cys Ile Ser
        50                  55                  60
    Glu Lys Leu Phe Met Glu Met Ala Glu Leu Met Val Ser Glu Gly Trp
    65                  70                  75                  80
    Lys Asp Ala Gly Tyr Glu Tyr Leu Cys Ile Asp Asp Cys Trp Met Ala
                85                  90                  95
    Pro Gln Arg Asp Ser Glu Gly Arg Leu Gln Ala Asp Pro Gln Arg Phe
                100                 105                 110
    Pro His Gly Ile Arg Gln Leu Ala Asn Tyr Val His Ser Lys Gly Leu
            115                 120                 125
    Lys Leu Gly Ile Tyr Ala Asp Val Gly Asn Lys Thr Cys Ala Gly Phe
        130                 135                 140
    Pro Gly Ser Phe Gly Tyr Tyr Asp Ile Asp Ala Gln Thr Phe Ala Asp
    145                 150                 155                 160
    Trp Gly Val Asp Leu Leu Lys Phe Asp Gly Cys Tyr Cys Asp Ser Leu
                165                 170                 175
    Glu Asn Leu Ala Asp Gly Tyr Lys His Met Ser Leu Ala Leu Asn Arg
                180                 185                 190
    Thr Gly Arg Ser Ile Val Tyr Ser Cys Glu Trp Pro Leu Tyr Met Trp
            195                 200                 205
    Pro Phe Gln Lys Pro Asn Tyr Thr Glu Ile Arg Gln Tyr Cys Asn His
        210                 215                 220
    Trp Arg Asn Phe Ala Asp Ile Asp Asp Ser Trp Lys Ser Ile Lys Ser
    225                 230                 235                 240
    Ile Leu Asp Trp Thr Ser Phe Asn Gln Glu Arg Ile Val Asp Val Ala
                245                 250                 255
    Gly Pro Gly Gly Trp Asn Asp Pro Asp Met Leu Val Ile Gly Asn Phe
                260                 265                 270
    Gly Leu Ser Trp Asn Gln Gln Val Thr Gln Met Ala Leu Trp Ala Ile
            275                 280                 285
    Met Ala Ala Pro Leu Phe Met Ser Asn Asp Leu Arg His Ile Ser Pro
        290                 295                 300
    Gln Ala Lys Ala Leu Leu Gln Asp Lys Asp Val Ile Ala Ile Asn Gln
    305                 310                 315                 320
    Asp Pro Leu Gly Lys Gln Gly Tyr Gln Leu Arg Gln Gly Asp Asn Phe
                325                 330                 335
    Glu Val Trp Glu Arg Pro Leu Ser Gly Leu Ala Trp Ala Val Ala Met
                340                 345                 350
```

```
            Ile Asn Arg Gln Glu Ile Gly Gly Pro Arg Ser Tyr Thr Ile Ala Val
                        355                 360                 365
            Ala Ser Leu Gly Lys Gly Val Ala Cys Asn Pro Ala Cys Phe Ile Thr
                    370                 375                 380
            Gln Leu Leu Pro Val Lys Arg Lys Leu Gly Phe Tyr Glu Trp Thr Ser
            385                 390                 395                 400
            Arg Leu Arg Ser His Ile Asn Pro Thr Gly Thr Val Leu Leu Gln Leu
                            405                 410                 415
            Glu Asn Thr Met Gln Met Ser Leu Lys Asp Leu Leu
                        420                 425

<210> SEQ ID NO 5
<211> LENGTH: 1308
<212> TYPE: DNA
<213> ORGANISM: Homo sapiens
<220> FEATURE:
<221> NAME/KEY: CDS
<222> LOCATION: (1)...(1308)

<400> SEQUENCE: 5 atg cag ctg agg aac cca gaa cta cat ctg ggc tgc gcg ctt gcg ctt      48
            Met Gln Leu Arg Asn Pro Glu Leu His Leu Gly Cys Ala Leu Ala Leu
            1               5                   10                  15
            cgc ttc ctg gcc ctc gtt tcc tgg gac atc cct ggg gct aga gca ctg      96
            Arg Phe Leu Ala Leu Val Ser Trp Asp Ile Pro Gly Ala Arg Ala Leu
                        20                  25                  30
            gac aat gga ttg gca agg acg cct acc atg ggc tgg ctg cac tgg gag     144
            Asp Asn Gly Leu Ala Arg Thr Pro Thr Met Gly Trp Leu His Trp Glu
                    35                  40                  45
            cgc ttc atg tgc aac ctt gac tgc cag gaa gag cca gat tcc tgc atc     192
            Arg Phe Met Cys Asn Leu Asp Cys Gln Glu Glu Pro Asp Ser Cys Ile
                50                  55                  60
            agt gag aag ctc ttc atg gag atg gca gag ctc atg gtc tca gaa ggc     240
            Ser Glu Lys Leu Phe Met Glu Met Ala Glu Leu Met Val Ser Glu Gly
            65                  70                  75                  80
            tgg aag gat gca ggt tat gag tac ctc tgc att gat gac tgt tgg atg     288
            Trp Lys Asp Ala Gly Tyr Glu Tyr Leu Cys Ile Asp Asp Cys Trp Met
                            85                  90                  95
            gct ccc caa aga gat tca gaa ggc aga ctt cag gca gac cct cag cgc     336
            Ala Pro Gln Arg Asp Ser Glu Gly Arg Leu Gln Ala Asp Pro Gln Arg
                        100                 105                 110
            ttt cct cat ggg att cgc cag cta gct aat tat gtt cac agc aaa gga     384
            Phe Pro His Gly Ile Arg Gln Leu Ala Asn Tyr Val His Ser Lys Gly
                    115                 120                 125
            ctg aag cta ggg att tat gca gat gtt gga aat aaa acc tgc gca ggc     432
            Leu Lys Leu Gly Ile Tyr Ala Asp Val Gly Asn Lys Thr Cys Ala Gly
                130                 135                 140
            ttc cct ggg agt ttt gga tac tac gac att gat gcc cag acc ttt gct     480
            Phe Pro Gly Ser Phe Gly Tyr Tyr Asp Ile Asp Ala Gln Thr Phe Ala
            145                 150                 155                 160
            gac tgg gga gta gat ctg cta aaa ttt gat ggt tgt tac tgt gac agt     528
            Asp Trp Gly Val Asp Leu Leu Lys Phe Asp Gly Cys Tyr Cys Asp Ser
                            165                 170                 175
            ttg gaa aat ttg gca gat ggt tat aag cac atg tcc ttg gcc ctg aat     576
            Leu Glu Asn Leu Ala Asp Gly Tyr Lys His Met Ser Leu Ala Leu Asn
                        180                 185                 190
            agg act ggc aga agc att gtg tac tcc tgt gag tgg cct ctt tat atg     624
            Arg Thr Gly Arg Ser Ile Val Tyr Ser Cys Glu Trp Pro Leu Tyr Met
                    195                 200                 205
            tgg ccc ttt caa aag ccc aat tat aca gaa atc cga cag tac tgc aat     672
            Trp Pro Phe Gln Lys Pro Asn Tyr Thr Glu Ile Arg Gln Tyr Cys Asn
                210                 215                 220
            cac tgg cga aat ttt gct gac att gat gat tcc tgg aaa agt ata aag     720
            His Trp Arg Asn Phe Ala Asp Ile Asp Asp Ser Trp Lys Ser Ile Lys
            225                 230                 235                 240
            agt atc ttg gac tgg aca tct ttt aac cag gag aga att gtt gat gtt     768
            Ser Ile Leu Asp Trp Thr Ser Phe Asn Gln Glu Arg Ile Val Asp Val
                            245                 250                 255
            gct gga cca ggg ggt tgg aat gac cca gat atg tta gtg att ggc aac     816
            Ala Gly Pro Gly Gly Trp Asn Asp Pro Asp Met Leu Val Ile Gly Asn
                        260                 265                 270
            ttt ggc ctc agc tgg aat cag caa gta act cag atg gcc ctc tgg gct     864
            Phe Gly Leu Ser Trp Asn Gln Gln Val Thr Gln Met Ala Leu Trp Ala
                    275                 280                 285
            atc atg gct gct cct tta ttc atg tct aat gac ctc cga cac atc agc     912
            Ile Met Ala Ala Pro Leu Phe Met Ser Asn Asp Leu Arg His Ile Ser
                290                 295                 300
```

```
cct caa gcc aaa gct ctc ctt cag gat aag gac gta att gcc atc aat    960
Pro Gln Ala Lys Ala Leu Leu Gln Asp Lys Asp Val Ile Ala Ile Asn
305                 310                 315                 320
cag gac ccc ttg ggc aag caa ggg tac cag ctt aga cag gga gac aac    1008
Gln Asp Pro Leu Gly Lys Gln Gly Tyr Gln Leu Arg Gln Gly Asp Asn
                325                 330                 335
ttt gaa gtg tgg gaa cga cct ctc tca ggc tta gcc tgg gct gta gct    1056
Phe Glu Val Trp Glu Arg Pro Leu Ser Gly Leu Ala Trp Ala Val Ala
            340                 345                 350
atg ata aac cgg cag gag att ggt gga cct cgc tct tat acc atc gca    1104
Met Ile Asn Arg Gln Glu Ile Gly Gly Pro Arg Ser Tyr Thr Ile Ala
        355                 360                 365
gtt gct tcc ctg ggt aaa gga gtg gcc tgt aat cct gcc tgc ttc atc    1152
Val Ala Ser Leu Gly Lys Gly Val Ala Cys Asn Pro Ala Cys Phe Ile
    370                 375                 380
aca cag ctc ctc cct gtg aaa agg aag cta ggg ttc tat gaa tgg act    1200
Thr Gln Leu Leu Pro Val Lys Arg Lys Leu Gly Phe Tyr Glu Trp Thr
385                 390                 395                 400
tca agg tta aga agt cac ata aat ccc aca ggc act gtt ttg ctt cag    1248
Ser Arg Leu Arg Ser His Ile Asn Pro Thr Gly Thr Val Leu Leu Gln
                405                 410                 415
cta gaa aac aca atg cag atg tct tta aaa gac tta ctt tct gaa aag    1296
Leu Glu Asn Thr Met Gln Met Ser Leu Lys Asp Leu Leu Ser Glu Lys
            420                 425                 430
gac gaa tta tga                                                    1308
Asp Glu Leu *
        435

<210> SEQ ID NO 6
<211> LENGTH: 435
<212> TYPE: PRT
<213> ORGANISM: Homo sapiens

<400> SEQUENCE: 6

Met Gln Leu Arg Asn Pro Glu Leu His Leu Gly Cys Ala Leu Ala Leu
    1               5                   10                  15
    Arg Phe Leu Ala Leu Val Ser Trp Asp Ile Pro Gly Ala Arg Ala Leu
                    20                  25                  30
    Asp Asn Gly Leu Ala Arg Thr Pro Thr Met Gly Trp Leu His Trp Glu
                35                  40                  45
    Arg Phe Met Cys Asn Leu Asp Cys Gln Glu Glu Pro Asp Ser Cys Ile
            50                  55                  60
    Ser Glu Lys Leu Phe Met Glu Met Ala Glu Leu Met Val Ser Glu Gly
    65                  70                  75                  80
    Trp Lys Asp Ala Gly Tyr Glu Tyr Leu Cys Ile Asp Asp Cys Trp Met
                    85                  90                  95
    Ala Pro Gln Arg Asp Ser Glu Gly Arg Leu Gln Ala Asp Pro Gln Arg
                    100                 105                 110
    Phe Pro His Gly Ile Arg Gln Leu Ala Asn Tyr Val His Ser Lys Gly
                115                 120                 125
    Leu Lys Leu Gly Ile Tyr Ala Asp Val Gly Asn Lys Thr Cys Ala Gly
            130                 135                 140
    Phe Pro Gly Ser Phe Gly Tyr Tyr Asp Ile Asp Ala Gln Thr Phe Ala
    145                 150                 155                 160
    Asp Trp Gly Val Asp Leu Leu Lys Phe Asp Gly Cys Tyr Cys Asp Ser
                    165                 170                 175
    Leu Glu Asn Leu Ala Asp Gly Tyr Lys His Met Ser Leu Ala Leu Asn
                180                 185                 190
    Arg Thr Gly Arg Ser Ile Val Tyr Ser Cys Glu Trp Pro Leu Tyr Met
            195                 200                 205
    Trp Pro Phe Gln Lys Pro Asn Tyr Thr Glu Ile Arg Gln Tyr Cys Asn
        210                 215                 220
    His Trp Arg Asn Phe Ala Asp Ile Asp Asp Ser Trp Lys Ser Ile Lys
    225                 230                 235                 240
    Ser Ile Leu Asp Trp Thr Ser Phe Asn Gln Glu Arg Ile Val Asp Val
                    245                 250                 255
    Ala Gly Pro Gly Gly Trp Asn Asp Pro Asp Met Leu Val Ile Gly Asn
                260                 265                 270
    Phe Gly Leu Ser Trp Asn Gln Gln Val Thr Gln Met Ala Leu Trp Ala
            275                 280                 285
    Ile Met Ala Ala Pro Leu Phe Met Ser Asn Asp Leu Arg His Ile Ser
        290                 295                 300
    Pro Gln Ala Lys Ala Leu Leu Gln Asp Lys Asp Val Ile Ala Ile Asn
    305                 310                 315                 320
    Gln Asp Pro Leu Gly Lys Gln Gly Tyr Gln Leu Arg Gln Gly Asp Asn
                    325                 330                 335
    Phe Glu Val Trp Glu Arg Pro Leu Ser Gly Leu Ala Trp Ala Val Ala
```

```
                    340              345              350
        Met Ile Asn Arg Gln Glu Ile Gly Gly Pro Arg Ser Tyr Thr Ile Ala
                355              360              365
        Val Ala Ser Leu Gly Lys Gly Val Ala Cys Asn Pro Ala Cys Phe Ile
                370              375              380
        Thr Gln Leu Leu Pro Val Lys Arg Lys Leu Gly Phe Tyr Glu Trp Thr
        385              390              395              400
        Ser Arg Leu Arg Ser His Ile Asn Pro Thr Gly Thr Val Leu Leu Gln
                    405              410              415
        Leu Glu Asn Thr Met Gln Met Ser Leu Lys Asp Leu Leu Ser Glu Lys
                420              425              430
        Asp Glu Leu
                435

<210> SEQ ID NO 7
<211> LENGTH: 1278
<212> TYPE: DNA
<213> ORGANISM: Homo sapiens
<220> FEATURE:
<221> NAME/KEY: CDS
<222> LOCATION: (1)...(1275)

<400> SEQUENCE: 7 atg cag ctg agg aac cca gaa cta cat ctg ggc tgc gcg ctt gcg ctt        48
    Met Gln Leu Arg Asn Pro Glu Leu His Leu Gly Cys Ala Leu Ala Leu
    1               5                   10                  15
    cgc ttc ctg gcc ctc gtt tcc tgg gac atc cct ggg gct aga gca ctg        96
    Arg Phe Leu Ala Leu Val Ser Trp Asp Ile Pro Gly Ala Arg Ala Leu
                    20                  25                  30
    gac aat gga ttg gca agg acg cct acc atg ggc tgg ctg cac tgg gag       144
    Asp Asn Gly Leu Ala Arg Thr Pro Thr Met Gly Trp Leu His Trp Glu
                35                  40                  45
    cgc ttc atg tgc aac ctt gac tgc cag gaa gag cca gat tcc tgc atc       192
    Arg Phe Met Cys Asn Leu Asp Cys Gln Glu Glu Pro Asp Ser Cys Ile
            50                  55                  60
    agt gag aag ctc ttc atg gag atg gca gag ctc atg gtc tca gaa ggc       240
    Ser Glu Lys Leu Phe Met Glu Met Ala Glu Leu Met Val Ser Glu Gly
    65                  70                  75                  80
    tgg aag gat gca ggt tat gag tac ctc tgc att gat gac tgt tgg atg       288
    Trp Lys Asp Ala Gly Tyr Glu Tyr Leu Cys Ile Asp Asp Cys Trp Met
                    85                  90                  95
    gct ccc caa aga gat tca gaa ggc aga ctt cag gca gac cct cag cgc       336
    Ala Pro Gln Arg Asp Ser Glu Gly Arg Leu Gln Ala Asp Pro Gln Arg
                    100                 105                 110
    ttt cct cat ggg att cgc cag cta gct aat tat gtt cac agc aaa gga       384
    Phe Pro His Gly Ile Arg Gln Leu Ala Asn Tyr Val His Ser Lys Gly
                115                 120                 125
    ctg aag cta ggg att tat gca gat gtt gga aat aaa acc tgc gca ggc       432
    Leu Lys Leu Gly Ile Tyr Ala Asp Val Gly Asn Lys Thr Cys Ala Gly
            130                 135                 140
    ttc cct ggg agt ttt gga tac tac gac att gat gcc cag acc ttt gct       480
    Phe Pro Gly Ser Phe Gly Tyr Tyr Asp Ile Asp Ala Gln Thr Phe Ala
    145                 150                 155                 160
    gac tgg gga gta gat ctg cta aaa ttt gat ggt tgt tac tgt gac agt       528
    Asp Trp Gly Val Asp Leu Leu Lys Phe Asp Gly Cys Tyr Cys Asp Ser
                    165                 170                 175
    ttg gaa aat ttg gca gat ggt tat aag cac atg tcc ttg gcc ctg aat       576
    Leu Glu Asn Leu Ala Asp Gly Tyr Lys His Met Ser Leu Ala Leu Asn
                    180                 185                 190
    agg act ggc aga agc att gtg tac tcc tgt gag tgg cct ctt tat atg       624
    Arg Thr Gly Arg Ser Ile Val Tyr Ser Cys Glu Trp Pro Leu Tyr Met
                195                 200                 205
    tgg ccc ttt caa aag ccc aat tat aca gaa atc cga cag tac tgc aat       672
    Trp Pro Phe Gln Lys Pro Asn Tyr Thr Glu Ile Arg Gln Tyr Cys Asn
            210                 215                 220
    cac tgg cga aat ttt gct gac att gat gat tcc tgg aaa agt ata aag       720
    His Trp Arg Asn Phe Ala Asp Ile Asp Asp Ser Trp Lys Ser Ile Lys
    225                 230                 235                 240
    agt atc ttg gac tgg aca tct ttt aac cag gag aga att gtt gat gtt       768
    Ser Ile Leu Asp Trp Thr Ser Phe Asn Gln Glu Arg Ile Val Asp Val
                    245                 250                 255
    gct gga cca ggg ggt tgg aat gac cca gat atg tta gtg att ggc aac       816
    Ala Gly Pro Gly Gly Trp Asn Asp Pro Asp Met Leu Val Ile Gly Asn
                    260                 265                 270
    ttt ggc ctc agc tgg aat cag caa gta act cag atg gcc ctc tgg gct       864
    Phe Gly Leu Ser Trp Asn Gln Gln Val Thr Gln Met Ala Leu Trp Ala
                275                 280                 285
```

```
atc atg gct gct cct tta ttc atg tct aat gac ctc cga cac atc agc      912
Ile Met Ala Ala Pro Leu Phe Met Ser Asn Asp Leu Arg His Ile Ser
            290                 295                 300
cct caa gcc aaa gct ctc ctt cag gat aag gac gta att gcc atc aat      960
Pro Gln Ala Lys Ala Leu Leu Gln Asp Lys Asp Val Ile Ala Ile Asn
305                 310                 315                 320
cag gac ccc ttg ggc aag caa ggg tac cag ctt aga cag gga gac aac     1008
Gln Asp Pro Leu Gly Lys Gln Gly Tyr Gln Leu Arg Gln Gly Asp Asn
                325                 330                 335
ttt gaa gtg tgg gaa cga cct ctc tca ggc tta gcc tgg gct gta gct     1056
Phe Glu Val Trp Glu Arg Pro Leu Ser Gly Leu Ala Trp Ala Val Ala
            340                 345                 350
atg ata aac cgg cag gag att ggt gga cct cgc tct tat acc atc gca     1104
Met Ile Asn Arg Gln Glu Ile Gly Gly Pro Arg Ser Tyr Thr Ile Ala
        355                 360                 365
gtt gct tcc ctg ggt aaa gga gtg gcc tgt aat cct gcc tgc ttc atc     1152
Val Ala Ser Leu Gly Lys Gly Val Ala Cys Asn Pro Ala Cys Phe Ile
370                 375                 380
aca cag ctc ctc cct gtg aaa agg aag cta ggg ttc tat gaa tgg act     1200
Thr Gln Leu Leu Pro Val Lys Arg Lys Leu Gly Phe Tyr Glu Trp Thr
385                 390                 395                 400
tca agg tta aga agt cac ata aat ccc aca ggc act gtt ttg ctt cag     1248
Ser Arg Leu Arg Ser His Ile Asn Pro Thr Gly Thr Val Leu Leu Gln
                405                 410                 415
cta gaa aca atg cag atg tct tta tga                                 1278
Leu Glu Asn Thr Met Gln Met Ser Leu
            420                 425
```

<210> SEQ ID NO 8
<211> LENGTH: 424
<212> TYPE: PRT
<213> ORGANISM: Homo sapiens

<400> SEQUENCE: 8

```
Gln Leu Arg Asn Pro Glu Leu His Leu Gly Cys Ala Leu Ala Leu Arg
 1               5                  10                  15
Phe Leu Ala Leu Val Ser Trp Asp Ile Pro Gly Ala Arg Ala Leu Asp
                20                  25                  30
Asn Gly Leu Ala Arg Thr Pro Thr Met Gly Trp Leu His Trp Glu Arg
            35                  40                  45
Phe Met Cys Asn Leu Asp Cys Gln Glu Glu Pro Asp Ser Cys Ile Ser
        50                  55                  60
Glu Lys Leu Phe Met Glu Met Ala Glu Leu Met Val Ser Glu Gly Trp
 65                  70                  75                  80
Lys Asp Ala Gly Tyr Glu Tyr Leu Cys Ile Asp Asp Cys Trp Met Ala
                85                  90                  95
Pro Gln Arg Asp Ser Glu Gly Arg Leu Gln Ala Asp Pro Gln Arg Phe
            100                 105                 110
Pro His Gly Ile Arg Gln Leu Ala Asn Tyr Val His Ser Lys Gly Leu
        115                 120                 125
Lys Leu Gly Ile Tyr Ala Asp Val Gly Asn Lys Thr Cys Ala Gly Phe
130                 135                 140
Pro Gly Ser Phe Gly Tyr Tyr Asp Ile Asp Ala Gln Thr Phe Ala Asp
145                 150                 155                 160
Trp Gly Val Asp Leu Leu Lys Phe Asp Gly Cys Tyr Cys Asp Ser Leu
                165                 170                 175
Glu Asn Leu Ala Asp Gly Tyr Lys His Met Ser Leu Ala Leu Asn Arg
            180                 185                 190
Thr Gly Arg Ser Ile Val Tyr Ser Cys Glu Trp Pro Leu Tyr Met Trp
        195                 200                 205
Pro Phe Gln Lys Pro Asn Tyr Thr Glu Ile Arg Gln Tyr Cys Asn His
    210                 215                 220
Trp Arg Asn Phe Ala Asp Ile Asp Asp Ser Trp Lys Ser Ile Lys Ser
225                 230                 235                 240
Ile Leu Asp Trp Thr Ser Phe Asn Gln Glu Arg Ile Val Asp Val Ala
                245                 250                 255
Gly Pro Gly Gly Trp Asn Asp Pro Asp Met Leu Val Ile Gly Asn Phe
            260                 265                 270
Gly Leu Ser Trp Asn Gln Gln Val Thr Gln Met Ala Leu Trp Ala Ile
        275                 280                 285
Met Ala Ala Pro Leu Phe Met Ser Asn Asp Leu Arg His Ile Ser Pro
    290                 295                 300
Gln Ala Lys Ala Leu Leu Gln Asp Lys Asp Val Ile Ala Ile Asn Gln
305                 310                 315                 320
Asp Pro Leu Gly Lys Gln Gly Tyr Gln Leu Arg Gln Gly Asp Asn Phe
                325                 330                 335
Glu Val Trp Glu Arg Pro Leu Ser Gly Leu Ala Trp Ala Val Ala Met
```

|     |     |     |     |     |     |     |     |     |     |     |     |     |
| --- | --- | --- | --- | --- | --- | --- | --- | --- | --- | --- | --- | --- |
|     |     | 340 |     |     |     | 345 |     |     |     | 350 |     |     |
| Ile | Asn | Arg | Gln | Glu | Ile | Gly | Gly | Pro | Arg | Ser | Tyr | Thr | Ile | Ala | Val |
|     |     |     | 355 |     |     |     | 360 |     |     |     | 365 |     |
| Ala | Ser | Leu | Gly | Lys | Gly | Val | Ala | Cys | Asn | Pro | Ala | Cys | Phe | Ile | Thr |
|     | 370 |     |     |     | 375 |     |     |     | 380 |     |     |     |
| Gln | Leu | Leu | Pro | Val | Lys | Arg | Lys | Leu | Gly | Phe | Tyr | Glu | Trp | Thr | Ser |
| 385 |     |     |     | 390 |     |     |     | 395 |     |     |     | 400 |
| Arg | Leu | Arg | Ser | His | Ile | Asn | Pro | Thr | Gly | Thr | Val | Leu | Leu | Gln | Leu |
|     |     |     | 405 |     |     |     | 410 |     |     |     | 415 |     |
| Glu | Asn | Thr | Met | Gln | Met | Ser | Leu |
|     |     |     | 420 |

<210> SEQ ID NO 9
<211> LENGTH: 1296
<212> TYPE: DNA
<213> ORGANISM: Homo sapiens
<220> FEATURE:
<221> NAME/KEY: CDS
<222> LOCATION: (1)...(1296)

<400> SEQUENCE: 9

| atg | cag | ctg | agg | aac | cca | gaa | cta | cat | ctg | ggc | tgc | gcg | ctt | gcg | ctt | 48 |
| Met | Gln | Leu | Arg | Asn | Pro | Glu | Leu | His | Leu | Gly | Cys | Ala | Leu | Ala | Leu |
| 1   |     |     |     | 5   |     |     |     |     | 10  |     |     |     |     | 15  |
| cgc | ttc | ctg | gcc | ctc | gtt | tcc | tgg | gac | atc | cct | ggg | gct | aga | gca | ctg | 96 |
| Arg | Phe | Leu | Ala | Leu | Val | Ser | Trp | Asp | Ile | Pro | Gly | Ala | Arg | Ala | Leu |
|     |     |     | 20  |     |     |     |     | 25  |     |     |     |     | 30  |     |
| gac | aat | gga | ttg | gca | agg | acg | cct | acc | atg | ggc | tgg | ctg | cac | tgg | gag | 144 |
| Asp | Asn | Gly | Leu | Ala | Arg | Thr | Pro | Thr | Met | Gly | Trp | Leu | His | Trp | Glu |
|     |     | 35  |     |     |     |     | 40  |     |     |     |     | 45  |     |     |
| cgc | ttc | atg | tgc | aac | ctt | gac | tgc | cag | gaa | gag | cca | gat | tcc | tgc | atc | 192 |
| Arg | Phe | Met | Cys | Asn | Leu | Asp | Cys | Gln | Glu | Glu | Pro | Asp | Ser | Cys | Ile |
|     | 50  |     |     |     |     | 55  |     |     |     |     | 60  |     |     |     |
| agt | gag | aag | ctc | ttc | atg | gag | atg | gca | gag | ctc | atg | gtc | tca | gaa | ggc | 240 |
| Ser | Glu | Lys | Leu | Phe | Met | Glu | Met | Ala | Glu | Leu | Met | Val | Ser | Glu | Gly |
| 65  |     |     |     |     | 70  |     |     |     |     | 75  |     |     |     |     | 80  |
| tgg | aag | gat | gca | ggt | tat | gag | tac | ctc | tgc | att | gat | gac | tgt | tgg | atg | 288 |
| Trp | Lys | Asp | Ala | Gly | Tyr | Glu | Tyr | Leu | Cys | Ile | Asp | Asp | Cys | Trp | Met |
|     |     |     |     | 85  |     |     |     |     | 90  |     |     |     |     | 95  |     |
| gct | ccc | caa | aga | gat | tca | gaa | ggc | aga | ctt | cag | gca | gac | cct | cag | cgc | 336 |
| Ala | Pro | Gln | Arg | Asp | Ser | Glu | Gly | Arg | Leu | Gln | Ala | Asp | Pro | Gln | Arg |
|     |     |     | 100 |     |     |     |     | 105 |     |     |     |     | 110 |     |
| ttt | cct | cat | ggg | att | cgc | cag | cta | gct | aat | tat | gtt | cac | agc | aaa | gga | 384 |
| Phe | Pro | His | Gly | Ile | Arg | Gln | Leu | Ala | Asn | Tyr | Val | His | Ser | Lys | Gly |
|     |     | 115 |     |     |     |     | 120 |     |     |     |     | 125 |     |     |
| ctg | aag | cta | ggg | att | tat | gca | gat | gtt | gga | aat | aaa | acc | tgc | gca | ggc | 432 |
| Leu | Lys | Leu | Gly | Ile | Tyr | Ala | Asp | Val | Gly | Asn | Lys | Thr | Cys | Ala | Gly |
|     | 130 |     |     |     |     | 135 |     |     |     |     | 140 |     |     |     |
| ttc | cct | ggg | agt | ttt | gga | tac | tac | gac | att | gat | gcc | cag | acc | ttt | gct | 480 |
| Phe | Pro | Gly | Ser | Phe | Gly | Tyr | Tyr | Asp | Ile | Asp | Ala | Gln | Thr | Phe | Ala |
| 145 |     |     |     |     | 150 |     |     |     |     | 155 |     |     |     |     | 160 |
| gac | tgg | gga | gta | gat | ctg | cta | aaa | ttt | gat | ggt | tgt | tac | tgt | gac | agt | 528 |
| Asp | Trp | Gly | Val | Asp | Leu | Leu | Lys | Phe | Asp | Gly | Cys | Tyr | Cys | Asp | Ser |
|     |     |     |     | 165 |     |     |     |     | 170 |     |     |     |     | 175 |     |
| ttg | gaa | aat | ttg | gca | gat | ggt | tat | aag | cac | atg | tcc | ttg | gcc | ctg | aat | 576 |
| Leu | Glu | Asn | Leu | Ala | Asp | Gly | Tyr | Lys | His | Met | Ser | Leu | Ala | Leu | Asn |
|     |     |     | 180 |     |     |     |     | 185 |     |     |     |     | 190 |     |
| agg | act | ggc | aga | agc | att | gtg | tac | tcc | tgt | gag | tgg | cct | ctt | tat | atg | 624 |
| Arg | Thr | Gly | Arg | Ser | Ile | Val | Tyr | Ser | Cys | Glu | Trp | Pro | Leu | Tyr | Met |
|     |     | 195 |     |     |     |     | 200 |     |     |     |     | 205 |     |     |
| tgg | ccc | ttt | caa | aag | ccc | aat | tat | aca | gaa | atc | cga | cag | tac | tgc | aat | 672 |
| Trp | Pro | Phe | Gln | Lys | Pro | Asn | Tyr | Thr | Glu | Ile | Arg | Gln | Tyr | Cys | Asn |
|     | 210 |     |     |     |     | 215 |     |     |     |     | 220 |     |     |     |
| cac | tgg | cga | aat | ttt | gct | gac | att | gat | gat | tcc | tgg | aaa | agt | ata | aag | 720 |
| His | Trp | Arg | Asn | Phe | Ala | Asp | Ile | Asp | Asp | Ser | Trp | Lys | Ser | Ile | Lys |
| 225 |     |     |     |     | 230 |     |     |     |     | 235 |     |     |     |     | 240 |
| agt | atc | ttg | gac | tgg | aca | tct | ttt | aac | cag | gag | aga | att | gtt | gat | gtt | 768 |
| Ser | Ile | Leu | Asp | Trp | Thr | Ser | Phe | Asn | Gln | Glu | Arg | Ile | Val | Asp | Val |
|     |     |     |     | 245 |     |     |     |     | 250 |     |     |     |     | 255 |     |
| gct | gga | cca | ggg | ggt | tgg | aat | gac | cca | gat | atg | tta | gtg | att | ggc | aac | 816 |
| Ala | Gly | Pro | Gly | Gly | Trp | Asn | Asp | Pro | Asp | Met | Leu | Val | Ile | Gly | Asn |
|     |     |     | 260 |     |     |     |     | 265 |     |     |     |     | 270 |     |
| ttt | ggc | ctc | agc | tgg | aat | cag | caa | gta | act | cag | atg | gcc | ctc | tgg | gct | 864 |
| Phe | Gly | Leu | Ser | Trp | Asn | Gln | Gln | Val | Thr | Gln | Met | Ala | Leu | Trp | Ala |
|     |     | 275 |     |     |     |     | 280 |     |     |     |     | 285 |     |     |
| atc | atg | gct | gct | cct | tta | ttc | atg | tct | aat | gac | ctc | cga | cac | atc | agc | 912 |
| Ile | Met | Ala | Ala | Pro | Leu | Phe | Met | Ser | Asn | Asp | Leu | Arg | His | Ile | Ser |

```
                  290                     295                     300
        cct caa gcc aaa gct ctc ctt cag gat aag gac gta att gcc atc aat      960
        Pro Gln Ala Lys Ala Leu Leu Gln Asp Lys Asp Val Ile Ala Ile Asn
        305                 310                     315                 320
        cag gac ccc ttg ggc aag caa ggg tac cag ctt aga cag gga gac aac     1008
        Gln Asp Pro Leu Gly Lys Gln Gly Tyr Gln Leu Arg Gln Gly Asp Asn
                        325                     330                 335
        ttt gaa gtg tgg gaa cga cct ctc tca ggc tta gcc tgg gct gta gct     1056
        Phe Glu Val Trp Glu Arg Pro Leu Ser Gly Leu Ala Trp Ala Val Ala
                    340                     345                 350
        atg ata aac cgg cag gag att ggt gga cct cgc tct tat acc atc gca     1104
        Met Ile Asn Arg Gln Glu Ile Gly Gly Pro Arg Ser Tyr Thr Ile Ala
                355                     360                 365
        gtt gct tcc ctg ggt aaa gga gtg gcc tgt aat cct gcc tgc ttc atc     1152
        Val Ala Ser Leu Gly Lys Gly Val Ala Cys Asn Pro Ala Cys Phe Ile
            370                     375                 380
        aca cag ctc ctc cct gtg aaa agg aag cta ggg ttc tat gaa tgg act     1200
        Thr Gln Leu Leu Pro Val Lys Arg Lys Leu Gly Phe Tyr Glu Trp Thr
        385                 390                     395                 400
        tca agg tta aga agt cac ata aat ccc aca ggc act gtt ttg ctt cag     1248
        Ser Arg Leu Arg Ser His Ile Asn Pro Thr Gly Thr Val Leu Leu Gln
                        405                     410                 415
        cta gaa aac aca atg cag atg tct tta tct gaa aag gac gaa tta tga     1296
        Leu Glu Asn Thr Met Gln Met Ser Leu Ser Glu Lys Asp Glu Leu  *
                    420                     425                 430

<210> SEQ ID NO 10
<211> LENGTH: 431
<212> TYPE: PRT
<213> ORGANISM: Homo sapiens

<400> SEQUENCE: 10

Met Gln Leu Arg Asn Pro Glu Leu His Leu Gly Cys Ala Leu Ala Leu
    1               5                   10                  15
    Arg Phe Leu Ala Leu Val Ser Trp Asp Ile Pro Gly Ala Arg Ala Leu
                    20                  25                  30
    Asp Asn Gly Leu Ala Arg Thr Pro Thr Met Gly Trp Leu His Trp Glu
                35                  40                  45
    Arg Phe Met Cys Asn Leu Asp Cys Gln Glu Glu Pro Asp Ser Cys Ile
            50                  55                  60
    Ser Glu Lys Leu Phe Met Glu Met Ala Glu Leu Met Val Ser Glu Gly
    65                  70                  75                  80
    Trp Lys Asp Ala Gly Tyr Glu Tyr Leu Cys Ile Asp Asp Cys Trp Met
                    85                  90                  95
    Ala Pro Gln Arg Asp Ser Glu Gly Arg Leu Gln Ala Asp Pro Gln Arg
                100                 105                 110
    Phe Pro His Gly Ile Arg Gln Leu Ala Asn Tyr Val His Ser Lys Gly
                115                 120                 125
    Leu Lys Leu Gly Ile Tyr Ala Asp Val Gly Asn Lys Thr Cys Ala Gly
            130                 135                 140
    Phe Pro Gly Ser Phe Gly Tyr Tyr Asp Ile Asp Ala Gln Thr Phe Ala
    145                 150                 155                 160
    Asp Trp Gly Val Asp Leu Leu Lys Phe Asp Gly Cys Tyr Cys Asp Ser
                    165                 170                 175
    Leu Glu Asn Leu Ala Asp Gly Tyr Lys His Met Ser Leu Ala Leu Asn
                180                 185                 190
    Arg Thr Gly Arg Ser Ile Val Tyr Ser Cys Glu Trp Pro Leu Tyr Met
            195                 200                 205
    Trp Pro Phe Gln Lys Pro Asn Tyr Thr Glu Ile Arg Gln Tyr Cys Asn
    210                 215                 220
    His Trp Arg Asn Phe Ala Asp Ile Asp Asp Ser Trp Lys Ser Ile Lys
    225                 230                 235                 240
    Ser Ile Leu Asp Trp Thr Ser Phe Asn Gln Glu Arg Ile Val Asp Val
                    245                 250                 255
    Ala Gly Pro Gly Gly Trp Asn Asp Pro Asp Met Leu Val Ile Gly Asn
                260                 265                 270
    Phe Gly Leu Ser Trp Asn Gln Gln Val Thr Gln Met Ala Leu Trp Ala
            275                 280                 285
    Ile Met Ala Ala Pro Leu Phe Met Ser Asn Asp Leu Arg His Ile Ser
    290                 295                 300
    Pro Gln Ala Lys Ala Leu Leu Gln Asp Lys Asp Val Ile Ala Ile Asn
    305                 310                 315                 320
    Gln Asp Pro Leu Gly Lys Gln Gly Tyr Gln Leu Arg Gln Gly Asp Asn
                    325                 330                 335
    Phe Glu Val Trp Glu Arg Pro Leu Ser Gly Leu Ala Trp Ala Val Ala
                340                 345                 350
    Met Ile Asn Arg Gln Glu Ile Gly Gly Pro Arg Ser Tyr Thr Ile Ala
```

```
            355                 360                 365
    Val Ala Ser Leu Gly Lys Gly Val Ala Cys Asn Pro Ala Cys Phe Ile
    370                 375                 380
    Thr Gln Leu Leu Pro Val Lys Arg Lys Leu Gly Phe Tyr Glu Trp Thr
385                 390                 395                 400
    Ser Arg Leu Arg Ser His Ile Asn Pro Thr Gly Thr Val Leu Leu Gln
                    405                 410                 415
    Leu Glu Asn Thr Met Gln Met Ser Leu Ser Glu Lys Asp Glu Leu
                420                 425                 430

<210> SEQ ID NO 11
<211> LENGTH: 1266
<212> TYPE: DNA
<213> ORGANISM: Homo sapiens
<220> FEATURE:
<221> NAME/KEY: CDS
<222> LOCATION: (1)...(1266)

<400> SEQUENCE: 11 atg cag ctg agg aac cca gaa cta cat ctg ggc tgc gcg ctt gcg ctt     48
    Met Gln Leu Arg Asn Pro Glu Leu His Leu Gly Cys Ala Leu Ala Leu
      1               5                  10                  15
    cgc ttc ctg gcc ctc gtt tcc tgg gac atc cct ggg gct aga gca ctg     96
    Arg Phe Leu Ala Leu Val Ser Trp Asp Ile Pro Gly Ala Arg Ala Leu
                     20                  25                  30
    gac aat gga ttg gca agg acg cct acc atg ggc tgg ctg cac tgg gag    144
    Asp Asn Gly Leu Ala Arg Thr Pro Thr Met Gly Trp Leu His Trp Glu
                 35                  40                  45
    cgc ttc atg tgc aac ctt gac tgc cag gaa gag cca gat tcc tgc atc    192
    Arg Phe Met Cys Asn Leu Asp Cys Gln Glu Glu Pro Asp Ser Cys Ile
             50                  55                  60
    agt gag aag ctc ttc atg gag atg gca gag ctc atg gtc tca gaa ggc    240
    Ser Glu Lys Leu Phe Met Glu Met Ala Glu Leu Met Val Ser Glu Gly
     65                  70                  75                  80
    tgg aag gat gca ggt tat gag tac ctc tgc att gat gac tgt tgg atg    288
    Trp Lys Asp Ala Gly Tyr Glu Tyr Leu Cys Ile Asp Asp Cys Trp Met
                     85                  90                  95
    gct ccc caa aga gat tca gaa ggc aga ctt cag gca gac cct cag cgc    336
    Ala Pro Gln Arg Asp Ser Glu Gly Arg Leu Gln Ala Asp Pro Gln Arg
                    100                 105                 110
    ttt cct cat ggg att cgc cag cta gct aat tat gtt cac agc aaa gga    384
    Phe Pro His Gly Ile Arg Gln Leu Ala Asn Tyr Val His Ser Lys Gly
                115                 120                 125
    ctg aag cta ggg att tat gca gat gtt gga aat aaa acc tgc gca ggc    432
    Leu Lys Leu Gly Ile Tyr Ala Asp Val Gly Asn Lys Thr Cys Ala Gly
            130                 135                 140
    ttc cct ggg agt ttt gga tac tac gac att gat gcc cag acc ttt gct    480
    Phe Pro Gly Ser Phe Gly Tyr Tyr Asp Ile Asp Ala Gln Thr Phe Ala
    145                 150                 155                 160
    gac tgg gga gta gat ctg cta aaa ttt gat ggt tgt tac tgt gac agt    528
    Asp Trp Gly Val Asp Leu Leu Lys Phe Asp Gly Cys Tyr Cys Asp Ser
                    165                 170                 175
    ttg gaa aat ttg gca gat ggt tat aag cac atg tcc ttg gcc ctg aat    576
    Leu Glu Asn Leu Ala Asp Gly Tyr Lys His Met Ser Leu Ala Leu Asn
                180                 185                 190
    agg act gga aga agc att gtg tac tcc tgt gag tgg cct ctt tat atg    624
    Arg Thr Gly Arg Ser Ile Val Tyr Ser Cys Glu Trp Pro Leu Tyr Met
                195                 200                 205
    tgg ccc ttt caa aag ccc aat tat aca gaa atc cga cag tac tgc aat    672
    Trp Pro Phe Gln Lys Pro Asn Tyr Thr Glu Ile Arg Gln Tyr Cys Asn
            210                 215                 220
    cac tgg cga aat ttt gct gac att gat gat tcc tgg aaa agt ata aag    720
    His Trp Arg Asn Phe Ala Asp Ile Asp Asp Ser Trp Lys Ser Ile Lys
    225                 230                 235                 240
    agt atc ttg gac tgg aca tct ttt aac cag gag aga att gtt gat gtt    768
    Ser Ile Leu Asp Trp Thr Ser Phe Asn Gln Glu Arg Ile Val Asp Val
                    245                 250                 255
    gct gga cca ggg ggt tgg aat gac cca gat atg tta gtg att ggc aac    816
    Ala Gly Pro Gly Gly Trp Asn Asp Pro Asp Met Leu Val Ile Gly Asn
                260                 265                 270
    ttt ggc ctc agc tgg aat cag caa gta act cag atg gcc ctc tgg gct    864
    Phe Gly Leu Ser Trp Asn Gln Gln Val Thr Gln Met Ala Leu Trp Ala
                275                 280                 285
    atc atg gct gct cct tta ttc atg tct aat gac ctc cga cac atc agc    912
    Ile Met Ala Ala Pro Leu Phe Met Ser Asn Asp Leu Arg His Ile Ser
            290                 295                 300
    cct caa gcc aaa gct ctc ctt cag gat aag gac gta att gcc atc aat    960
```

-continued

```
        Pro Gln Ala Lys Ala Leu Leu Gln Asp Lys Asp Val Ile Ala Ile Asn
        305                 310                 315                 320
cag gac ccc ttg ggc aag caa ggg tac cag ctt aga cag gga gac aac       1008
Gln Asp Pro Leu Gly Lys Gln Gly Tyr Gln Leu Arg Gln Gly Asp Asn
                325                 330                 335
ttt gaa gtg tgg gaa cga cct ctc tca ggc tta gcc tgg gct gta gct       1056
Phe Glu Val Trp Glu Arg Pro Leu Ser Gly Leu Ala Trp Ala Val Ala
            340                 345                 350
atg ata aac cgg cag gag att ggt gga cct cgc tct tat acc atc gca       1104
Met Ile Asn Arg Gln Glu Ile Gly Gly Pro Arg Ser Tyr Thr Ile Ala
        355                 360                 365
gtt gct tcc ctg ggt aaa gga gtg gcc tgt aat cct gcc tgc ttc atc       1152
Val Ala Ser Leu Gly Lys Gly Val Ala Cys Asn Pro Ala Cys Phe Ile
    370                 375                 380
aca cag ctc ctc cct gtg aaa agg aag cta ggg ttc tat gaa tgg act       1200
Thr Gln Leu Leu Pro Val Lys Arg Lys Leu Gly Phe Tyr Glu Trp Thr
385                 390                 395                 400
tca agg tta aga agt cac ata aat ccc aca ggc act gtt ttg ctt cag       1248
Ser Arg Leu Arg Ser His Ile Asn Pro Thr Gly Thr Val Leu Leu Gln
                405                 410                 415
cta gaa aac aca atg taa                                               1266
Leu Glu Asn Thr Met *
                420

<210> SEQ ID NO 12
<211> LENGTH: 421
<212> TYPE: PRT
<213> ORGANISM: Homo sapiens

<400> SEQUENCE: 12

Met Gln Leu Arg Asn Pro Glu Leu His Leu Gly Cys Ala Leu Ala Leu
    1               5                   10                  15
    Arg Phe Leu Ala Leu Val Ser Trp Asp Ile Pro Gly Ala Arg Ala Leu
                    20                  25                  30
    Asp Asn Gly Leu Ala Arg Thr Pro Thr Met Gly Trp Leu His Trp Glu
                35                  40                  45
    Arg Phe Met Cys Asn Leu Asp Cys Gln Glu Glu Pro Asp Ser Cys Ile
        50                  55                  60
    Ser Glu Lys Leu Phe Met Glu Met Ala Glu Leu Met Val Ser Glu Gly
    65                  70                  75                  80
    Trp Lys Asp Ala Gly Tyr Glu Tyr Leu Cys Ile Asp Asp Cys Trp Met
                    85                  90                  95
    Ala Pro Gln Arg Asp Ser Glu Gly Arg Leu Gln Ala Asp Pro Gln Arg
                    100                 105                 110
    Phe Pro His Gly Ile Arg Gln Leu Ala Asn Tyr Val His Ser Lys Gly
                115                 120                 125
    Leu Lys Leu Gly Ile Tyr Ala Asp Val Gly Asn Lys Thr Cys Ala Gly
        130                 135                 140
    Phe Pro Gly Ser Phe Gly Tyr Tyr Asp Ile Asp Ala Gln Thr Phe Ala
    145                 150                 155                 160
    Asp Trp Gly Val Asp Leu Leu Lys Phe Asp Gly Cys Tyr Cys Asp Ser
                    165                 170                 175
    Leu Glu Asn Leu Ala Asp Gly Tyr Lys His Met Ser Leu Ala Leu Asn
                    180                 185                 190
    Arg Thr Gly Arg Ser Ile Val Tyr Ser Cys Glu Trp Pro Leu Tyr Met
        195                 200                 205
    Trp Pro Phe Gln Lys Pro Asn Tyr Thr Glu Ile Arg Gln Tyr Cys Asn
        210                 215                 220
    His Trp Arg Asn Phe Ala Asp Ile Asp Asp Ser Trp Lys Ser Ile Lys
    225                 230                 235                 240
    Ser Ile Leu Asp Trp Thr Ser Phe Asn Gln Glu Arg Ile Val Asp Val
                    245                 250                 255
    Ala Gly Pro Gly Gly Trp Asn Asp Pro Asp Met Leu Val Ile Gly Asn
                260                 265                 270
    Phe Gly Leu Ser Trp Asn Gln Gln Val Thr Gln Met Ala Leu Trp Ala
        275                 280                 285
    Ile Met Ala Ala Pro Leu Phe Met Ser Asn Asp Leu Arg His Ile Ser
        290                 295                 300
    Pro Gln Ala Lys Ala Leu Leu Gln Asp Lys Asp Val Ile Ala Ile Asn
    305                 310                 315                 320
    Gln Asp Pro Leu Gly Lys Gln Gly Tyr Gln Leu Arg Gln Gly Asp Asn
                    325                 330                 335
    Phe Glu Val Trp Glu Arg Pro Leu Ser Gly Leu Ala Trp Ala Val Ala
                340                 345                 350
    Met Ile Asn Arg Gln Glu Ile Gly Gly Pro Arg Ser Tyr Thr Ile Ala
        355                 360                 365
    Val Ala Ser Leu Gly Lys Gly Val Ala Cys Asn Pro Ala Cys Phe Ile
```

```
            370                 375                 380
        Thr Gln Leu Leu Pro Val Lys Arg Lys Leu Gly Phe Tyr Glu Trp Thr
        385                 390                 395                 400
        Ser Arg Leu Arg Ser His Ile Asn Pro Thr Gly Thr Val Leu Leu Gln
                        405                 410                 415
        Leu Glu Asn Thr Met
                    420

<210> SEQ ID NO 13
<211> LENGTH: 1284
<212> TYPE: DNA
<213> ORGANISM: Homo sapiens
<220> FEATURE:
<221> NAME/KEY: CDS
<222> LOCATION: (1)...(1284)

<400> SEQUENCE: 13 atg cag ctg agg aac cca gaa cta cat ctg ggc tgc gcg ctt gcg ctt      48
        Met Gln Leu Arg Asn Pro Glu Leu His Leu Gly Cys Ala Leu Ala Leu
        1               5                   10                  15
        cgc ttc ctg gcc ctc gtt tcc tgg gac atc cct ggg gct aga gca ctg      96
        Arg Phe Leu Ala Leu Val Ser Trp Asp Ile Pro Gly Ala Arg Ala Leu
                        20                  25                  30
        gac aat gga ttg gca agg acg cct acc atg ggc tgg ctg cac tgg gag     144
        Asp Asn Gly Leu Ala Arg Thr Pro Thr Met Gly Trp Leu His Trp Glu
                    35                  40                  45
        cgc ttc atg tgc aac ctt gac tgc cag gaa gag cca gat tcc tgc atc     192
        Arg Phe Met Cys Asn Leu Asp Cys Gln Glu Glu Pro Asp Ser Cys Ile
            50                  55                  60
        agt gag aag ctc ttc atg gag atg gca gag ctc atg gtc tca gaa ggc     240
        Ser Glu Lys Leu Phe Met Glu Met Ala Glu Leu Met Val Ser Glu Gly
        65                  70                  75                  80
        tgg aag gat gca ggt tat gag tac ctc tgc att gat gac tgt tgg atg     288
        Trp Lys Asp Ala Gly Tyr Glu Tyr Leu Cys Ile Asp Asp Cys Trp Met
                        85                  90                  95
        gct ccc caa aga gat tca gaa ggc aga ctt cag gca gac cct cag cgc     336
        Ala Pro Gln Arg Asp Ser Glu Gly Arg Leu Gln Ala Asp Pro Gln Arg
                    100                 105                 110
        ttt cct cat ggg att cgc cag cta gct aat tat gtt cac agc aaa gga     384
        Phe Pro His Gly Ile Arg Gln Leu Ala Asn Tyr Val His Ser Lys Gly
                115                 120                 125
        ctg aag cta ggg att tat gca gat gtt gga aat aaa acc tgc gca ggc     432
        Leu Lys Leu Gly Ile Tyr Ala Asp Val Gly Asn Lys Thr Cys Ala Gly
        130                 135                 140
        ttc cct ggg agt ttt gga tac tac gac att gat gcc cag acc ttt gct     480
        Phe Pro Gly Ser Phe Gly Tyr Tyr Asp Ile Asp Ala Gln Thr Phe Ala
        145                 150                 155                 160
        gac tgg gga gta gat ctg cta aaa ttt gat ggt tgt tac tgt gac agt     528
        Asp Trp Gly Val Asp Leu Leu Lys Phe Asp Gly Cys Tyr Cys Asp Ser
                        165                 170                 175
        ttg gaa aat ttg gca gat ggt tat aag cac atg tcc ttg gcc ctg aat     576
        Leu Glu Asn Leu Ala Asp Gly Tyr Lys His Met Ser Leu Ala Leu Asn
                    180                 185                 190
        agg act ggc aga agc att gtg tac tcc tgt gag tgg cct ctt tat atg     624
        Arg Thr Gly Arg Ser Ile Val Tyr Ser Cys Glu Trp Pro Leu Tyr Met
                195                 200                 205
        tgg ccc ttt caa aag ccc aat tat aca gaa atc cga cag tac tgc aat     672
        Trp Pro Phe Gln Lys Pro Asn Tyr Thr Glu Ile Arg Gln Tyr Cys Asn
        210                 215                 220
        cac tgg cga aat ttt gct gac att gat gat tcc tgg aaa agt ata aag     720
        His Trp Arg Asn Phe Ala Asp Ile Asp Asp Ser Trp Lys Ser Ile Lys
        225                 230                 235                 240
        agt atc ttg gac tgg aca tct ttt aac cag gag aga att gtt gat gtt     768
        Ser Ile Leu Asp Trp Thr Ser Phe Asn Gln Glu Arg Ile Val Asp Val
                        245                 250                 255
        gct gga cca ggg ggt tgg aat gac cca gat atg tta gtg att ggc aac     816
        Ala Gly Pro Gly Gly Trp Asn Asp Pro Asp Met Leu Val Ile Gly Asn
                    260                 265                 270
        ttt ggc ctc agc tgg aat cag caa gta act cag atg gcc ctc tgg gct     864
        Phe Gly Leu Ser Trp Asn Gln Gln Val Thr Gln Met Ala Leu Trp Ala
                275                 280                 285
        atc atg gct gct cct tta ttc atg tct aat gac ctc cga cac atc agc     912
        Ile Met Ala Ala Pro Leu Phe Met Ser Asn Asp Leu Arg His Ile Ser
        290                 295                 300
        cct caa gcc aaa gct ctc ctt cag gat aag gac gta att gcc atc aat     960
        Pro Gln Ala Lys Ala Leu Leu Gln Asp Lys Asp Val Ile Ala Ile Asn
        305                 310                 315                 320
```

```
        cag gac ccc ttg ggc aag caa ggg tac cag ctt aga cag gga gac aac     1008
        Gln Asp Pro Leu Gly Lys Gln Gly Tyr Gln Leu Arg Gln Gly Asp Asn
                        325                 330                 335
        ttt gaa gtg tgg gaa cga cct ctc tca ggc tta gcc tgg gct gta gct     1056
        Phe Glu Val Trp Glu Arg Pro Leu Ser Gly Leu Ala Trp Ala Val Ala
                    340                 345                 350
        atg ata aac cgg cag gag att ggt gga cct cgc tct tat acc atc gca     1104
        Met Ile Asn Arg Gln Glu Ile Gly Gly Pro Arg Ser Tyr Thr Ile Ala
                355                 360                 365
        gtt gct tcc ctg ggt aaa gga gtg gcc tgt aat cct gcc tgc ttc atc     1152
        Val Ala Ser Leu Gly Lys Gly Val Ala Cys Asn Pro Ala Cys Phe Ile
            370                 375                 380
        aca cag ctc ctc cct gtg aaa agg aag cta ggg ttc tat gaa tgg act     1200
        Thr Gln Leu Leu Pro Val Lys Arg Lys Leu Gly Phe Tyr Glu Trp Thr
        385                 390                 395                 400
        tca agg tta aga agt cac ata aat ccc aca ggc act gtt tgt ctt cag     1248
        Ser Arg Leu Arg Ser His Ile Asn Pro Thr Gly Thr Val Leu Leu Gln
                        405                 410                 415
        cta gaa aac aca atg tct gaa aag gac gaa tta tga                     1284
        Leu Glu Asn Thr Met Ser Glu Lys Asp Glu Leu *
                    420                 425

<210> SEQ ID NO 14
<211> LENGTH: 427
<212> TYPE: PRT
<213> ORGANISM: Homo sapiens

<400> SEQUENCE: 14

Met Gln Leu Arg Asn Pro Glu Leu His Leu Gly Cys Ala Leu Ala Leu
    1               5                   10                  15
    Arg Phe Leu Ala Leu Val Ser Trp Asp Ile Pro Gly Ala Arg Ala Leu
                20                  25                  30
    Asp Asn Gly Leu Ala Arg Thr Pro Thr Met Gly Trp Leu His Trp Glu
            35                  40                  45
    Arg Phe Met Cys Asn Leu Asp Cys Gln Glu Glu Pro Asp Ser Cys Ile
        50                  55                  60
    Ser Glu Lys Leu Phe Met Glu Met Ala Glu Leu Met Val Ser Glu Gly
    65                  70                  75                  80
    Trp Lys Asp Ala Gly Tyr Glu Tyr Leu Cys Ile Asp Asp Cys Trp Met
                    85                  90                  95
    Ala Pro Gln Arg Asp Ser Glu Gly Arg Leu Gln Ala Asp Pro Gln Arg
                100                 105                 110
    Phe Pro His Gly Ile Arg Gln Leu Ala Asn Tyr Val His Ser Lys Gly
            115                 120                 125
    Leu Lys Leu Gly Ile Tyr Ala Asp Val Gly Asn Lys Thr Cys Ala Gly
        130                 135                 140
    Phe Pro Gly Ser Phe Gly Tyr Tyr Asp Ile Asp Ala Gln Thr Phe Ala
    145                 150                 155                 160
    Asp Trp Gly Val Asp Leu Leu Lys Phe Asp Gly Cys Tyr Cys Asp Ser
                    165                 170                 175
    Leu Glu Asn Leu Ala Asp Gly Tyr Lys His Met Ser Leu Ala Leu Asn
                180                 185                 190
    Arg Thr Gly Arg Ser Ile Val Tyr Ser Cys Glu Trp Pro Leu Tyr Met
            195                 200                 205
    Trp Pro Phe Gln Lys Pro Asn Tyr Thr Glu Ile Arg Gln Tyr Cys Asn
        210                 215                 220
    His Trp Arg Asn Phe Ala Asp Ile Asp Asp Ser Trp Lys Ser Ile Lys
    225                 230                 235                 240
    Ser Ile Leu Asp Trp Thr Ser Phe Asn Gln Glu Arg Ile Val Asp Val
                    245                 250                 255
    Ala Gly Pro Gly Gly Trp Asn Asp Pro Asp Met Leu Val Ile Gly Asn
                260                 265                 270
    Phe Gly Leu Ser Trp Asn Gln Gln Val Thr Gln Met Ala Leu Trp Ala
            275                 280                 285
    Ile Met Ala Ala Pro Leu Phe Met Ser Asn Asp Leu Arg His Ile Ser
        290                 295                 300
    Pro Gln Ala Lys Ala Leu Leu Gln Asp Lys Asp Val Ile Ala Ile Asn
    305                 310                 315                 320
    Gln Asp Pro Leu Gly Lys Gln Gly Tyr Gln Leu Arg Gln Gly Asp Asn
                    325                 330                 335
    Phe Glu Val Trp Glu Arg Pro Leu Ser Gly Leu Ala Trp Ala Val Ala
                340                 345                 350
    Met Ile Asn Arg Gln Glu Ile Gly Gly Pro Arg Ser Tyr Thr Ile Ala
            355                 360                 365
    Val Ala Ser Leu Gly Lys Gly Val Ala Cys Asn Pro Ala Cys Phe Ile
        370                 375                 380
    Thr Gln Leu Leu Pro Val Lys Arg Lys Leu Gly Phe Tyr Glu Trp Thr
```

```
                385                 390                 395                 400
            Ser Arg Leu Arg Ser His Ile Asn Pro Thr Gly Thr Val Leu Leu Gln
                            405                 410                 415
            Leu Glu Asn Thr Met Ser Glu Lys Asp Glu Leu
                        420                 425

<210> SEQ ID NO 15
<211> LENGTH: 1254
<212> TYPE: DNA
<213> ORGANISM: Homo sapiens
<220> FEATURE:
<221> NAME/KEY: CDS
<222> LOCATION: (1)...(1254)

<400> SEQUENCE: 15 atg cag ctg agg aac cca gaa cta cat ctg ggc tgc gcg ctt gcg ctt      48
    Met Gln Leu Arg Asn Pro Glu Leu His Leu Gly Cys Ala Leu Ala Leu
    1               5                   10                  15
    cgc ttc ctg gcc ctc gtt tcc tgg gac atc cct ggg gct aga gca ctg      96
    Arg Phe Leu Ala Leu Val Ser Trp Asp Ile Pro Gly Ala Arg Ala Leu
                    20                  25                  30
    gac aat gga ttg gca agg acg cct acc atg ggc tgg ctg cac tgg gag     144
    Asp Asn Gly Leu Ala Arg Thr Pro Thr Met Gly Trp Leu His Trp Glu
                35                  40                  45
    cgc ttc atg tgc aac ctt gac tgc cag gaa gag cca gat tcc tgc atc     192
    Arg Phe Met Cys Asn Leu Asp Cys Gln Glu Glu Pro Asp Ser Cys Ile
        50                  55                  60
    agt gag aag ctc ttc atg gag atg gca gag ctc atg gtc tca gaa ggc     240
    Ser Glu Lys Leu Phe Met Glu Met Ala Glu Leu Met Val Ser Glu Gly
    65                  70                  75                  80
    tgg aag gat gca ggt tat gag tac ctc tgc att gat gac tgt tgg atg     288
    Trp Lys Asp Ala Gly Tyr Glu Tyr Leu Cys Ile Asp Asp Cys Trp Met
                    85                  90                  95
    gct ccc caa aga gat tca gaa ggc aga ctt cag gca gac cct cag cgc     336
    Ala Pro Gln Arg Asp Ser Glu Gly Arg Leu Gln Ala Asp Pro Gln Arg
                    100                 105                 110
    ttt cct cat ggg att cgc cag cta gct aat tat gtt cac agc aaa gga     384
    Phe Pro His Gly Ile Arg Gln Leu Ala Asn Tyr Val His Ser Lys Gly
                115                 120                 125
    ctg aag cta ggg att tat gca gat gtt gga aat aaa acc tgc gca ggc     432
    Leu Lys Leu Gly Ile Tyr Ala Asp Val Gly Asn Lys Thr Cys Ala Gly
        130                 135                 140
    ttc cct ggg agt ttt gga tac tac gac att gat gcc cag acc ttt gct     480
    Phe Pro Gly Ser Phe Gly Tyr Tyr Asp Ile Asp Ala Gln Thr Phe Ala
    145                 150                 155                 160
    gac tgg gga gta gat ctg cta aaa ttt gat ggt tgt tac tgt gac agt     528
    Asp Trp Gly Val Asp Leu Leu Lys Phe Asp Gly Cys Tyr Cys Asp Ser
                    165                 170                 175
    ttg gaa aat ttg gca gat ggt tat aag cac atg tcc ttg gcc ctg aat     576
    Leu Glu Asn Leu Ala Asp Gly Tyr Lys His Met Ser Leu Ala Leu Asn
                    180                 185                 190
    agg act ggc aga agc att gtg tac tcc tgt gag tgg cct ctt tat atg     624
    Arg Thr Gly Arg Ser Ile Val Tyr Ser Cys Glu Trp Pro Leu Tyr Met
                195                 200                 205
    tgg ccc ttt caa aag ccc aat tat aca gaa atc cga cag tac tgc aat     672
    Trp Pro Phe Gln Lys Pro Asn Tyr Thr Glu Ile Arg Gln Tyr Cys Asn
        210                 215                 220
    cac tgg cga aat ttt gct gac att gat gat tcc tgg aaa agt ata aag     720
    His Trp Arg Asn Phe Ala Asp Ile Asp Asp Ser Trp Lys Ser Ile Lys
    225                 230                 235                 240
    agt atc ttg gac tgg aca tct ttt aac cag gag aga att gtt gat gtt     768
    Ser Ile Leu Asp Trp Thr Ser Phe Asn Gln Glu Arg Ile Val Asp Val
                    245                 250                 255
    gct gga cca ggg ggt tgg aat gac cca gat atg tta gtg att ggc aac     816
    Ala Gly Pro Gly Gly Trp Asn Asp Pro Asp Met Leu Val Ile Gly Asn
                    260                 265                 270
    ttt ggc ctc agc tgg aat cag caa gta act cag atg gcc ctc tgg gct     864
    Phe Gly Leu Ser Trp Asn Gln Gln Val Thr Gln Met Ala Leu Trp Ala
                275                 280                 285
    atc atg gct gct cct tta ttc atg tct aat gac ctc cga cac atc agc     912
    Ile Met Ala Ala Pro Leu Phe Met Ser Asn Asp Leu Arg His Ile Ser
        290                 295                 300
    cct caa gcc aaa gct ctc ctt cag gat aag gac gta att gcc atc aat     960
    Pro Gln Ala Lys Ala Leu Leu Gln Asp Lys Asp Val Ile Ala Ile Asn
    305                 310                 315                 320
    cag gac ccc ttg ggc aag caa ggg tac cag ctt aga cag gga gac aac    1008
    Gln Asp Pro Leu Gly Lys Gln Gly Tyr Gln Leu Arg Gln Gly Asp Asn
```

```
                              325                      330                      335
         ttt gaa gtg tgg gaa cga cct ctc tca ggc tta gcc tgg gct gta gct    1056
         Phe Glu Val Trp Glu Arg Pro Leu Ser Gly Leu Ala Trp Ala Val Ala
                340                      345                      350
         atg ata aac cgg cag gag att ggt gga cct cgc tct tat acc atc gca    1104
         Met Ile Asn Arg Gln Glu Ile Gly Gly Pro Arg Ser Tyr Thr Ile Ala
                    355                      360                      365
         gtt gct tcc ctg ggt aaa gga gtg gcc tgt aat cct gcc tgc ttc atc    1152
         Val Ala Ser Leu Gly Lys Gly Val Ala Cys Asn Pro Ala Cys Phe Ile
                370                      375                      380
         aca cag ctc ctc cct gtg aaa agg aag cta ggg ttc tat gaa tgg act    1200
         Thr Gln Leu Leu Pro Val Lys Arg Lys Leu Gly Phe Tyr Glu Trp Thr
         385                      390                      395                      400
         tca agg tta aga agt cac ata aat ccc aca ggc act gtt ttg ctt cag    1248
         Ser Arg Leu Arg Ser His Ile Asn Pro Thr Gly Thr Val Leu Leu Gln
                        405                      410                      415
         cta taa                                                            1254
         Leu *

<210> SEQ ID NO 16
<211> LENGTH: 417
<212> TYPE: PRT
<213> ORGANISM: Homo sapiens

<400> SEQUENCE: 16

Met Gln Leu Arg Asn Pro Glu Leu His Leu Gly Cys Ala Leu Ala Leu
    1               5                   10                  15
    Arg Phe Leu Ala Leu Val Ser Trp Asp Ile Pro Gly Ala Arg Ala Leu
                20                  25                  30
    Asp Asn Gly Leu Ala Arg Thr Pro Thr Met Gly Trp Leu His Trp Glu
            35                  40                  45
    Arg Phe Met Cys Asn Leu Asp Cys Gln Glu Glu Pro Asp Ser Cys Ile
        50                  55                  60
    Ser Glu Lys Leu Phe Met Glu Met Ala Glu Leu Met Val Ser Glu Gly
    65                  70                  75                  80
    Trp Lys Asp Ala Gly Tyr Glu Tyr Leu Cys Ile Asp Asp Cys Trp Met
                    85                  90                  95
    Ala Pro Gln Arg Asp Ser Glu Gly Arg Leu Gln Ala Asp Pro Gln Arg
                100                 105                 110
    Phe Pro His Gly Ile Arg Gln Leu Ala Asn Tyr Val His Ser Lys Gly
            115                 120                 125
    Leu Lys Leu Gly Ile Tyr Ala Asp Val Gly Asn Lys Thr Cys Ala Gly
        130                 135                 140
    Phe Pro Gly Ser Phe Gly Tyr Tyr Asp Ile Asp Ala Gln Thr Phe Ala
    145                 150                 155                 160
    Asp Trp Gly Val Asp Leu Leu Lys Phe Asp Gly Cys Tyr Cys Asp Ser
                    165                 170                 175
    Leu Glu Asn Leu Ala Asp Gly Tyr Lys His Met Ser Leu Ala Leu Asn
                180                 185                 190
    Arg Thr Gly Arg Ser Ile Val Tyr Ser Cys Glu Trp Pro Leu Tyr Met
            195                 200                 205
    Trp Pro Phe Gln Lys Pro Asn Tyr Thr Glu Ile Arg Gln Tyr Cys Asn
        210                 215                 220
    His Trp Arg Asn Phe Ala Asp Ile Asp Asp Ser Trp Lys Ser Ile Lys
    225                 230                 235                 240
    Ser Ile Leu Asp Trp Thr Ser Phe Asn Gln Glu Arg Ile Val Asp Val
                    245                 250                 255
    Ala Gly Pro Gly Gly Trp Asn Asp Pro Asp Met Leu Val Ile Gly Asn
                260                 265                 270
    Phe Gly Leu Ser Trp Asn Gln Gln Val Thr Gln Met Ala Leu Trp Ala
            275                 280                 285
    Ile Met Ala Ala Pro Leu Phe Met Ser Asn Asp Leu Arg His Ile Ser
        290                 295                 300
    Pro Gln Ala Lys Ala Leu Leu Gln Asp Lys Asp Val Ile Ala Ile Asn
    305                 310                 315                 320
    Gln Asp Pro Leu Gly Lys Gln Gly Tyr Gln Leu Arg Gln Gly Asp Asn
                    325                 330                 335
    Phe Glu Val Trp Glu Arg Pro Leu Ser Gly Leu Ala Trp Ala Val Ala
                340                 345                 350
    Met Ile Asn Arg Gln Glu Ile Gly Gly Pro Arg Ser Tyr Thr Ile Ala
            355                 360                 365
    Val Ala Ser Leu Gly Lys Gly Val Ala Cys Asn Pro Ala Cys Phe Ile
        370                 375                 380
    Thr Gln Leu Leu Pro Val Lys Arg Lys Leu Gly Phe Tyr Glu Trp Thr
    385                 390                 395                 400
    Ser Arg Leu Arg Ser His Ile Asn Pro Thr Gly Thr Val Leu Leu Gln
                    405                 410                 415
```

Leu

<210> SEQ ID NO 17
<211> LENGTH: 1272
<212> TYPE: DNA
<213> ORGANISM: Homo sapiens
<220> FEATURE:
<221> NAME/KEY: CDS
<222> LOCATION: (1)...(1272)

<400> SEQUENCE: 17

| | | | | | | | | | | | | | | | | |
|---|---|---|---|---|---|---|---|---|---|---|---|---|---|---|---|---|
| atg | cag | ctg | agg | aac | cca | gaa | cta | cat | ctg | ggc | tgc | gcg | ctt | gcg | ctt | 48 |
| Met | Gln | Leu | Arg | Asn | Pro | Glu | Leu | His | Leu | Gly | Cys | Ala | Leu | Ala | Leu | |
| 1 | | | | 5 | | | | | 10 | | | | | 15 | | |
| cgc | ttc | ctg | gcc | ctc | gtt | tcc | tgg | gac | atc | cct | ggg | gct | aga | gca | ctg | 96 |
| Arg | Phe | Leu | Ala | Leu | Val | Ser | Trp | Asp | Ile | Pro | Gly | Ala | Arg | Ala | Leu | |
| | | | 20 | | | | | 25 | | | | | 30 | | | |
| gac | aat | gga | ttg | gca | agg | acg | cct | acc | atg | ggc | tgg | ctg | cac | tgg | gag | 144 |
| Asp | Asn | Gly | Leu | Ala | Arg | Thr | Pro | Thr | Met | Gly | Trp | Leu | His | Trp | Glu | |
| | 35 | | | | | 40 | | | | | 45 | | | | | |
| cgc | ttc | atg | tgc | aac | ctt | gac | tgc | cag | gaa | gag | cca | gat | tcc | tgc | atc | 192 |
| Arg | Phe | Met | Cys | Asn | Leu | Asp | Cys | Gln | Glu | Glu | Pro | Asp | Ser | Cys | Ile | |
| 50 | | | | | 55 | | | | | 60 | | | | | | |
| agt | gag | aag | ctc | ttc | atg | gag | atg | gca | gag | ctc | atg | gtc | tca | gaa | ggc | 240 |
| Ser | Glu | Lys | Leu | Phe | Met | Glu | Met | Ala | Glu | Leu | Met | Val | Ser | Glu | Gly | |
| 65 | | | | | 70 | | | | | 75 | | | | | 80 | |
| tgg | aag | gat | gca | ggt | tat | gag | tac | ctc | tgc | att | gat | gac | tgt | tgg | atg | 288 |
| Trp | Lys | Asp | Ala | Gly | Tyr | Glu | Tyr | Leu | Cys | Ile | Asp | Asp | Cys | Trp | Met | |
| | | | | 85 | | | | | 90 | | | | | 95 | | |
| gct | ccc | caa | aga | gat | tca | gaa | ggc | aga | ctt | cag | gca | gac | cct | cag | cgc | 336 |
| Ala | Pro | Gln | Arg | Asp | Ser | Glu | Gly | Arg | Leu | Gln | Ala | Asp | Pro | Gln | Arg | |
| | | | 100 | | | | | 105 | | | | | 110 | | | |
| ttt | cct | cat | ggg | att | cgc | cag | cta | gct | aat | tat | gtt | cac | agc | aaa | gga | 384 |
| Phe | Pro | His | Gly | Ile | Arg | Gln | Leu | Ala | Asn | Tyr | Val | His | Ser | Lys | Gly | |
| | | 115 | | | | | 120 | | | | | 125 | | | | |
| ctg | aag | cta | ggg | att | tat | gca | gat | gtt | gga | aat | aaa | acc | tgc | gca | ggc | 432 |
| Leu | Lys | Leu | Gly | Ile | Tyr | Ala | Asp | Val | Gly | Asn | Lys | Thr | Cys | Ala | Gly | |
| | 130 | | | | | 135 | | | | | 140 | | | | | |
| ttc | cct | ggg | agt | ttt | gga | tac | tac | gac | att | gat | gcc | cag | acc | ttt | gct | 480 |
| Phe | Pro | Gly | Ser | Phe | Gly | Tyr | Tyr | Asp | Ile | Asp | Ala | Gln | Thr | Phe | Ala | |
| 145 | | | | | 150 | | | | | 155 | | | | | 160 | |
| gac | tgg | gga | gta | gat | ctg | cta | aaa | ttt | gat | ggt | tgt | tac | tgt | gac | agt | 528 |
| Asp | Trp | Gly | Val | Asp | Leu | Leu | Lys | Phe | Asp | Gly | Cys | Tyr | Cys | Asp | Ser | |
| | | | | 165 | | | | | 170 | | | | | 175 | | |
| ttg | gaa | aat | ttg | gca | gat | ggt | tat | aag | cac | atg | tcc | ttg | gcc | ctg | aat | 576 |
| Leu | Glu | Asn | Leu | Ala | Asp | Gly | Tyr | Lys | His | Met | Ser | Leu | Ala | Leu | Asn | |
| | | | 180 | | | | | 185 | | | | | 190 | | | |
| agg | act | ggc | aga | agc | att | gtg | tac | tcc | tgt | gag | tgg | cct | ctt | tat | atg | 624 |
| Arg | Thr | Gly | Arg | Ser | Ile | Val | Tyr | Ser | Cys | Glu | Trp | Pro | Leu | Tyr | Met | |
| | | 195 | | | | | 200 | | | | | 205 | | | | |
| tgg | ccc | ttt | caa | aag | ccc | aat | tat | aca | gaa | atc | cga | cag | tac | tgc | aat | 672 |
| Trp | Pro | Phe | Gln | Lys | Pro | Asn | Tyr | Thr | Glu | Ile | Arg | Gln | Tyr | Cys | Asn | |
| | 210 | | | | | 215 | | | | | 220 | | | | | |
| cac | tgg | cga | aat | ttt | gct | gac | att | gat | gat | tcc | tgg | aaa | agt | ata | aag | 720 |
| His | Trp | Arg | Asn | Phe | Ala | Asp | Ile | Asp | Asp | Ser | Trp | Lys | Ser | Ile | Lys | |
| 225 | | | | | 230 | | | | | 235 | | | | | 240 | |
| agt | atc | ttg | gac | tgg | aca | tct | ttt | aac | cag | gag | aga | att | gtt | gat | gtt | 768 |
| Ser | Ile | Leu | Asp | Trp | Thr | Ser | Phe | Asn | Gln | Glu | Arg | Ile | Val | Asp | Val | |
| | | | | 245 | | | | | 250 | | | | | 255 | | |
| gct | gga | cca | ggg | ggt | tgg | aat | gac | cca | gat | atg | tta | gtg | att | ggc | aac | 816 |
| Ala | Gly | Pro | Gly | Gly | Trp | Asn | Asp | Pro | Asp | Met | Leu | Val | Ile | Gly | Asn | |
| | | | 260 | | | | | 265 | | | | | 270 | | | |
| ttt | ggc | ctc | agc | tgg | aat | cag | caa | gta | act | cag | atg | gcc | ctc | tgg | gct | 864 |
| Phe | Gly | Leu | Ser | Trp | Asn | Gln | Gln | Val | Thr | Gln | Met | Ala | Leu | Trp | Ala | |
| | | 275 | | | | | 280 | | | | | 285 | | | | |
| atc | atg | gct | gct | cct | tta | ttc | atg | tct | aat | gac | ctc | cga | cac | atc | agc | 912 |
| Ile | Met | Ala | Ala | Pro | Leu | Phe | Met | Ser | Asn | Asp | Leu | Arg | His | Ile | Ser | |
| | 290 | | | | | 295 | | | | | 300 | | | | | |
| cct | caa | gcc | aaa | gct | ctc | ctt | cag | gat | aag | gac | gta | att | gcc | atc | aat | 960 |
| Pro | Gln | Ala | Lys | Ala | Leu | Leu | Gln | Asp | Lys | Asp | Val | Ile | Ala | Ile | Asn | |
| 305 | | | | | 310 | | | | | 315 | | | | | 320 | |
| cag | gac | ccc | ttg | ggc | aag | caa | ggg | tac | cag | ctt | aga | cag | gga | gac | aac | 1008 |
| Gln | Asp | Pro | Leu | Gly | Lys | Gln | Gly | Tyr | Gln | Leu | Arg | Gln | Gly | Asp | Asn | |
| | | | | 325 | | | | | 330 | | | | | 335 | | |
| ttt | gaa | gtg | tgg | gaa | cga | cct | ctc | tca | ggc | tta | gcc | tgg | gct | gta | gct | 1056 |
| Phe | Glu | Val | Trp | Glu | Arg | Pro | Leu | Ser | Gly | Leu | Ala | Trp | Ala | Val | Ala | |
| | | | 340 | | | | | 345 | | | | | 350 | | | |

```
    atg ata aac cgg cag gag att ggt gga cct cgc tct tat acc atc gca    1104
    Met Ile Asn Arg Gln Glu Ile Gly Gly Pro Arg Ser Tyr Thr Ile Ala
        355                 360                 365
    gtt gct tcc ctg ggt aaa gga gtg gcc tgt aat cct gcc tgc ttc atc    1152
    Val Ala Ser Leu Gly Lys Gly Val Ala Cys Asn Pro Ala Cys Phe Ile
        370                 375                 380
    aca cag ctc ctc cct gtg aaa agg aag cta ggg ttc tat gaa tgg act    1200
    Thr Gln Leu Leu Pro Val Lys Arg Lys Leu Gly Phe Tyr Glu Trp Thr
    385                 390                 395                 400
    tca agg tta aga agt cac ata aat ccc aca ggc act gtt ttg ctt cag    1248
    Ser Arg Leu Arg Ser His Ile Asn Pro Thr Gly Thr Val Leu Leu Gln
                    405                 410                 415
    cta tct gaa aag gac gaa tta tga                                    1272
    Leu Ser Glu Lys Asp Glu Leu  *
                420
```

<210> SEQ ID NO 18
<211> LENGTH: 423
<212> TYPE: PRT
<213> ORGANISM: Homo sapiens

<400> SEQUENCE: 18

```
    Met Gln Leu Arg Asn Pro Glu Leu His Leu Gly Cys Ala Leu Ala Leu
    1               5                   10                  15
    Arg Phe Leu Ala Leu Val Ser Trp Asp Ile Pro Gly Ala Arg Ala Leu
                    20                  25                  30
    Asp Asn Gly Leu Ala Arg Thr Pro Thr Met Gly Trp Leu His Trp Glu
                35                  40                  45
    Arg Phe Met Cys Asn Leu Asp Cys Gln Glu Glu Pro Asp Ser Cys Ile
            50                  55                  60
    Ser Glu Lys Leu Phe Met Glu Met Ala Glu Leu Met Val Ser Glu Gly
    65                  70                  75                  80
    Trp Lys Asp Ala Gly Tyr Glu Tyr Leu Cys Ile Asp Asp Cys Trp Met
                    85                  90                  95
    Ala Pro Gln Arg Asp Ser Glu Gly Arg Leu Gln Ala Asp Pro Gln Arg
                100                 105                 110
    Phe Pro His Gly Ile Arg Gln Leu Ala Asn Tyr Val His Ser Lys Gly
                115                 120                 125
    Leu Lys Leu Gly Ile Tyr Ala Asp Val Gly Asn Lys Thr Cys Ala Gly
            130                 135                 140
    Phe Pro Gly Ser Phe Gly Tyr Tyr Asp Ile Asp Ala Gln Thr Phe Ala
    145                 150                 155                 160
    Asp Trp Gly Val Asp Leu Leu Lys Phe Asp Gly Cys Tyr Cys Asp Ser
                    165                 170                 175
    Leu Glu Asn Leu Ala Asp Gly Tyr Lys His Met Ser Leu Ala Leu Asn
                180                 185                 190
    Arg Thr Gly Arg Ser Ile Val Tyr Ser Cys Glu Trp Pro Leu Tyr Met
                195                 200                 205
    Trp Pro Phe Gln Lys Pro Asn Tyr Thr Glu Ile Arg Gln Tyr Cys Asn
            210                 215                 220
    His Trp Arg Asn Phe Ala Asp Ile Asp Asp Ser Trp Lys Ser Ile Lys
    225                 230                 235                 240
    Ser Ile Leu Asp Trp Thr Ser Phe Asn Gln Glu Arg Ile Val Asp Val
                    245                 250                 255
    Ala Gly Pro Gly Gly Trp Asn Asp Pro Asp Met Leu Val Ile Gly Asn
                260                 265                 270
    Phe Gly Leu Ser Trp Asn Gln Gln Val Thr Gln Met Ala Leu Trp Ala
                275                 280                 285
    Ile Met Ala Ala Pro Leu Phe Met Ser Asn Asp Leu Arg His Ile Ser
        290                 295                 300
    Pro Gln Ala Lys Ala Leu Leu Gln Asp Lys Asp Val Ile Ala Ile Asn
    305                 310                 315                 320
    Gln Asp Pro Leu Gly Lys Gln Gly Tyr Gln Leu Arg Gln Gly Asp Asn
                    325                 330                 335
    Phe Glu Val Trp Glu Arg Pro Leu Ser Gly Leu Ala Trp Ala Val Ala
                340                 345                 350
    Met Ile Asn Arg Gln Glu Ile Gly Gly Pro Arg Ser Tyr Thr Ile Ala
            355                 360                 365
    Val Ala Ser Leu Gly Lys Gly Val Ala Cys Asn Pro Ala Cys Phe Ile
        370                 375                 380
    Thr Gln Leu Leu Pro Val Lys Arg Lys Leu Gly Phe Tyr Glu Trp Thr
    385                 390                 395                 400
    Ser Arg Leu Arg Ser His Ile Asn Pro Thr Gly Thr Val Leu Leu Gln
                    405                 410                 415
    Leu Ser Glu Lys Asp Glu Leu
                420
```

<210> SEQ ID NO 19
<211> LENGTH: 1215
<212> TYPE: DNA
<213> ORGANISM: Homo sapiens
<220> FEATURE:
<221> NAME/KEY: CDS
<222> LOCATION: (10)...(1215)

<400> SEQUENCE: 19

```
atgcagctg agg aac cca gaa cta cat ctg ggc tgc gcg ctt gcg ctt cgc        51
          Arg Asn Pro Glu Leu His Leu Gly Cys Ala Leu Ala Leu Arg
            1               5                  10
ttc ctg gcc ctc gtt tcc tgg gac atc cct ggg gct aga gca ctg gac          99
Phe Leu Ala Leu Val Ser Trp Asp Ile Pro Gly Ala Arg Ala Leu Asp
 15                  20                  25                  30
aat gga ttg gca agg acg cct acc atg ggc tgg ctg cac tgg gag cgc         147
Asn Gly Leu Ala Arg Thr Pro Thr Met Gly Trp Leu His Trp Glu Arg
                 35                  40                  45
ttc atg tgc aac ctt gac tgc cag gaa gag cca gat tcc tgc atc agt         195
Phe Met Cys Asn Leu Asp Cys Gln Glu Glu Pro Asp Ser Cys Ile Ser
         50                  55                  60
gag aag ctc ttc atg gag atg gca gag ctc atg gtc tca gaa ggc tgg         243
Glu Lys Leu Phe Met Glu Met Ala Glu Leu Met Val Ser Glu Gly Trp
 65                  70                  75
aag gat gca ggt tat gag tac ctc tgc att gat gac tgt tgg atg gct         291
Lys Asp Ala Gly Tyr Glu Tyr Leu Cys Ile Asp Asp Cys Trp Met Ala
             80                  85                  90
ccc caa aga gat tca gaa ggc aga ctt cag gca gac cct cag cgc ttt         339
Pro Gln Arg Asp Ser Glu Gly Arg Leu Gln Ala Asp Pro Gln Arg Phe
 95                 100                 105                 110
cct cat ggg att cgc cag cta gct aat tat gtt cac agc aaa gga ctg         387
Pro His Gly Ile Arg Gln Leu Ala Asn Tyr Val His Ser Lys Gly Leu
                115                 120                 125
aag cta ggg att tat gca gat gtt gga aat aaa acc tgc gca ggc ttc         435
Lys Leu Gly Ile Tyr Ala Asp Val Gly Asn Lys Thr Cys Ala Gly Phe
            130                 135                 140
cct ggg agt ttt gga tac tac gac att gat gcc cag acc ttt gct gac         483
Pro Gly Ser Phe Gly Tyr Tyr Asp Ile Asp Ala Gln Thr Phe Ala Asp
        145                 150                 155
tgg gga gta gat ctg cta aaa ttt gat ggt tgt tac tgt gac agt ttg         531
Trp Gly Val Asp Leu Leu Lys Phe Asp Gly Cys Tyr Cys Asp Ser Leu
160                 165                 170
gaa aat ttg gca gat ggt tat aag cac atg tcc ttg gcc ctg aat agg         579
Glu Asn Leu Ala Asp Gly Tyr Lys His Met Ser Leu Ala Leu Asn Arg
175                 180                 185                 190
act ggc aga agc att gtg tac tcc tgt gag tgg cct ctt tat atg tgg         627
Thr Gly Arg Ser Ile Val Tyr Ser Cys Glu Trp Pro Leu Tyr Met Trp
                195                 200                 205
ccc ttt caa aag ccc aat tat aca gaa atc cga cag tac tgc aat cac         675
Pro Phe Gln Lys Pro Asn Tyr Thr Glu Ile Arg Gln Tyr Cys Asn His
            210                 215                 220
tgg cga aat ttt gct gac att gat gat tcc tgg aaa agt ata aag agt         723
Trp Arg Asn Phe Ala Asp Ile Asp Asp Ser Trp Lys Ser Ile Lys Ser
        225                 230                 235
atc ttg gac tgg aca tct ttt aac cag gag aga att gtt gat gtt gct         771
Ile Leu Asp Trp Thr Ser Phe Asn Gln Glu Arg Ile Val Asp Val Ala
240                 245                 250
gga cca ggg ggt tgg aat gac cca gat atg tta gtg att ggc aac ttt         819
Gly Pro Gly Gly Trp Asn Asp Pro Asp Met Leu Val Ile Gly Asn Phe
255                 260                 265                 270
ggc ctc agc tgg aat cag caa gta act cag atg gcc ctc tgg gct atc         867
Gly Leu Ser Trp Asn Gln Gln Val Thr Gln Met Ala Leu Trp Ala Ile
                275                 280                 285
atg gct gct cct tta ttc atg tct aat gac ctc cga cac atc agc cct         915
Met Ala Ala Pro Leu Phe Met Ser Asn Asp Leu Arg His Ile Ser Pro
            290                 295                 300
caa gcc aaa gct ctc ctt cag gat aag gac gta att gcc atc aat cag         963
Gln Ala Lys Ala Leu Leu Gln Asp Lys Asp Val Ile Ala Ile Asn Gln
        305                 310                 315
gac ccc ttg ggc aag caa ggg tac cag ctt aga cag gga gac aac ttt        1011
Asp Pro Leu Gly Lys Gln Gly Tyr Gln Leu Arg Gln Gly Asp Asn Phe
320                 325                 330
gaa gtg tgg gaa cga cct ctc tca ggc tta gcc tgg gct gta gct atg        1059
Glu Val Trp Glu Arg Pro Leu Ser Gly Leu Ala Trp Ala Val Ala Met
335                 340                 345                 350
ata aac cgg cag gag att ggt gga cct cgc tct tat acc atc gca gtt        1107
Ile Asn Arg Gln Glu Ile Gly Gly Pro Arg Ser Tyr Thr Ile Ala Val
```

```
                     355                 360                 365
   gct tcc ctg ggt aaa gga gtg gcc tgt aat cct gcc tgc ttc atc aca     1155
   Ala Ser Leu Gly Lys Gly Val Ala Cys Asn Pro Ala Cys Phe Ile Thr
               370                 375                 380
   cag ctc ctc cct gtg aaa agg aag cta ggg ttc tat gaa tgg act tca     1203
   Gln Leu Leu Pro Val Lys Arg Lys Leu Gly Phe Tyr Glu Trp Thr Ser
       385                 390                 395
   agg tta aga taa                                                     1215
   Arg Leu Arg *
       400
```

<210> SEQ ID NO 20
<211> LENGTH: 401
<212> TYPE: PRT
<213> ORGANISM: Homo sapiens

<400> SEQUENCE: 20

```
   Arg Asn Pro Glu Leu His Leu Gly Cys Ala Leu Ala Leu Arg Phe Leu
    1               5                  10                  15
   Ala Leu Val Ser Trp Asp Ile Pro Gly Ala Arg Ala Leu Asp Asn Gly
                   20                  25                  30
   Leu Ala Arg Thr Pro Thr Met Gly Trp Leu His Trp Glu Arg Phe Met
               35                  40                  45
   Cys Asn Leu Asp Cys Gln Glu Glu Pro Asp Ser Cys Ile Ser Glu Lys
           50                  55                  60
   Leu Phe Met Glu Met Ala Glu Leu Met Val Ser Glu Gly Trp Lys Asp
   65                  70                  75                  80
   Ala Gly Tyr Glu Tyr Leu Cys Ile Asp Asp Cys Trp Met Ala Pro Gln
                   85                  90                  95
   Arg Asp Ser Glu Gly Arg Leu Gln Ala Asp Pro Gln Arg Phe Pro His
                  100                 105                 110
   Gly Ile Arg Gln Leu Ala Asn Tyr Val His Ser Lys Gly Leu Lys Leu
                  115                 120                 125
   Gly Ile Tyr Ala Asp Val Gly Asn Lys Thr Cys Ala Gly Phe Pro Gly
                  130                 135                 140
   Ser Phe Gly Tyr Tyr Asp Ile Asp Ala Gln Thr Phe Ala Asp Trp Gly
   145                 150                 155                 160
   Val Asp Leu Leu Lys Phe Asp Gly Cys Tyr Cys Asp Ser Leu Glu Asn
                   165                 170                 175
   Leu Ala Asp Gly Tyr Lys His Met Ser Leu Ala Leu Asn Arg Thr Gly
                  180                 185                 190
   Arg Ser Ile Val Tyr Ser Cys Glu Trp Pro Leu Tyr Met Trp Pro Phe
                  195                 200                 205
   Gln Lys Pro Asn Tyr Thr Glu Ile Arg Gln Tyr Cys Asn His Trp Arg
                  210                 215                 220
   Asn Phe Ala Asp Ile Asp Asp Ser Trp Lys Ser Ile Lys Ser Ile Leu
   225                 230                 235                 240
   Asp Trp Thr Ser Phe Asn Gln Glu Arg Ile Val Asp Val Ala Gly Pro
                   245                 250                 255
   Gly Gly Trp Asn Asp Pro Asp Met Leu Val Ile Gly Asn Phe Gly Leu
                  260                 265                 270
   Ser Trp Asn Gln Gln Val Thr Gln Met Ala Leu Trp Ala Ile Met Ala
                  275                 280                 285
   Ala Pro Leu Phe Met Ser Asn Asp Leu Arg His Ile Ser Pro Gln Ala
                  290                 295                 300
   Lys Ala Leu Leu Gln Asp Lys Asp Val Ile Ala Ile Asn Gln Asp Pro
   305                 310                 315                 320
   Leu Gly Lys Gln Gly Tyr Gln Leu Arg Gln Gly Asp Asn Phe Glu Val
                   325                 330                 335
   Trp Glu Arg Pro Leu Ser Gly Leu Ala Trp Ala Val Ala Met Ile Asn
                  340                 345                 350
   Arg Gln Glu Ile Gly Gly Pro Arg Ser Tyr Thr Ile Ala Val Ala Ser
                  355                 360                 365
   Leu Gly Lys Gly Val Ala Cys Asn Pro Ala Cys Phe Ile Thr Gln Leu
                  370                 375                 380
   Leu Pro Val Lys Arg Lys Leu Gly Phe Tyr Glu Trp Thr Ser Arg Leu
   385                 390                 395                 400
   Arg
```

<210> SEQ ID NO 21
<211> LENGTH: 1233
<212> TYPE: DNA
<213> ORGANISM: Homo sapiens
<220> FEATURE:
<221> NAME/KEY: CDS
<222> LOCATION: (1)...(1233)

-continued

<400> SEQUENCE: 21

```
atg cag ctg agg aac cca gaa cta cat ctg ggc tgc gcg ctt gcg ctt        48
Met Gln Leu Arg Asn Pro Glu Leu His Leu Gly Cys Ala Leu Ala Leu
 1               5                  10                  15
cgc ttc ctg gcc ctc gtt tcc tgg gac atc cct ggg gct aga gca ctg        96
Arg Phe Leu Ala Leu Val Ser Trp Asp Ile Pro Gly Ala Arg Ala Leu
                 20                  25                  30
gac aat gga ttg gca agg acg cct acc atg ggc tgg ctg cac tgg gag       144
Asp Asn Gly Leu Ala Arg Thr Pro Thr Met Gly Trp Leu His Trp Glu
             35                  40                  45
cgc ttc atg tgc aac ctt gac tgc cag gaa gag cca gat tcc tgc atc       192
Arg Phe Met Cys Asn Leu Asp Cys Gln Glu Glu Pro Asp Ser Cys Ile
 50                  55                  60
agt gag aag ctc ttc atg gag atg gca gag ctc atg gtc tca gaa ggc       240
Ser Glu Lys Leu Phe Met Glu Met Ala Glu Leu Met Val Ser Glu Gly
 65                  70                  75                  80
tgg aag gat gca ggt tat gag tac ctc tgc att gat gac tgt tgg atg       288
Trp Lys Asp Ala Gly Tyr Glu Tyr Leu Cys Ile Asp Asp Cys Trp Met
                 85                  90                  95
gct ccc caa aga gat tca gaa ggc aga ctt cag gca gac cct cag cgc       336
Ala Pro Gln Arg Asp Ser Glu Gly Arg Leu Gln Ala Asp Pro Gln Arg
            100                 105                 110
ttt cct cat ggg att cgc cag cta gct aat tat gtt cac agc aaa gga       384
Phe Pro His Gly Ile Arg Gln Leu Ala Asn Tyr Val His Ser Lys Gly
            115                 120                 125
ctg aag cta ggg att tat gca gat gtt gga aat aaa acc tgc gca ggc       432
Leu Lys Leu Gly Ile Tyr Ala Asp Val Gly Asn Lys Thr Cys Ala Gly
        130                 135                 140
ttc cct ggg agt ttt gga tac tac gac att gat gcc cag acc ttt gct       480
Phe Pro Gly Ser Phe Gly Tyr Tyr Asp Ile Asp Ala Gln Thr Phe Ala
145                 150                 155                 160
gac tgg gga gta gat ctg cta aaa ttt gat ggt tgt tac tgt gac agt       528
Asp Trp Gly Val Asp Leu Leu Lys Phe Asp Gly Cys Tyr Cys Asp Ser
                165                 170                 175
ttg gaa aat ttg gca gat ggt tat aag cac atg tcc ttg gcc ctg aat       576
Leu Glu Asn Leu Ala Asp Gly Tyr Lys His Met Ser Leu Ala Leu Asn
            180                 185                 190
agg act ggc aga agc att gtg tac tcc tgt gag tgg cct ctt tat atg       624
Arg Thr Gly Arg Ser Ile Val Tyr Ser Cys Glu Trp Pro Leu Tyr Met
        195                 200                 205
tgg ccc ttt caa aag ccc aat tat aca gaa atc cga cag tac tgc aat       672
Trp Pro Phe Gln Lys Pro Asn Tyr Thr Glu Ile Arg Gln Tyr Cys Asn
    210                 215                 220
cac tgg cga aat ttt gct gac att gat gat tcc tgg aaa agt ata aag       720
His Trp Arg Asn Phe Ala Asp Ile Asp Asp Ser Trp Lys Ser Ile Lys
225                 230                 235                 240
agt atc ttg gac tgg aca tct ttt aac cag gag aga att gtt gat gtt       768
Ser Ile Leu Asp Trp Thr Ser Phe Asn Gln Glu Arg Ile Val Asp Val
                245                 250                 255
gct gga cca ggg ggt tgg aat gac cca gat atg tta gtg att ggc aac       816
Ala Gly Pro Gly Gly Trp Asn Asp Pro Asp Met Leu Val Ile Gly Asn
            260                 265                 270
ttt ggc ctc agc tgg aat cag caa gta act cag atg gcc ctc tgg gct       864
Phe Gly Leu Ser Trp Asn Gln Gln Val Thr Gln Met Ala Leu Trp Ala
        275                 280                 285
atc atg gct gct cct tta ttc atg tct aat gac ctc cga cac atc agc       912
Ile Met Ala Ala Pro Leu Phe Met Ser Asn Asp Leu Arg His Ile Ser
    290                 295                 300
cct caa gcc aaa gct ctc ctt cag gat aag gac gta att gcc atc aat       960
Pro Gln Ala Lys Ala Leu Leu Gln Asp Lys Asp Val Ile Ala Ile Asn
305                 310                 315                 320
cag gac ccc ttg ggc aag caa ggg tac cag ctt aga cag gga gac aac      1008
Gln Asp Pro Leu Gly Lys Gln Gly Tyr Gln Leu Arg Gln Gly Asp Asn
                325                 330                 335
ttt gaa gtg tgg gaa cga cct ctc tca ggc tta gcc tgg gct gta gct      1056
Phe Glu Val Trp Glu Arg Pro Leu Ser Gly Leu Ala Trp Ala Val Ala
            340                 345                 350
atg ata aac cgg cag gag att ggt gga cct cgc tct tat acc atc gca      1104
Met Ile Asn Arg Gln Glu Ile Gly Gly Pro Arg Ser Tyr Thr Ile Ala
        355                 360                 365
gtt gct tcc ctg ggt aaa gga gtg gcc tgt aat cct gcc tgc ttc atc      1152
Val Ala Ser Leu Gly Lys Gly Val Ala Cys Asn Pro Ala Cys Phe Ile
    370                 375                 380
aca cag ctc ctc cct gtg aaa agg aag cta ggg ttc tat gaa tgg act      1200
Thr Gln Leu Leu Pro Val Lys Arg Lys Leu Gly Phe Tyr Glu Trp Thr
385                 390                 395                 400
tca agg tta aga tct gaa aag gac gaa tta tga                          1233
```

```
            Ser Arg Leu Arg Ser Glu Lys Asp Glu Leu  *
                        405                 410

<210> SEQ ID NO 22
<211> LENGTH: 409
<212> TYPE: PRT
<213> ORGANISM: Homo sapiens

<400> SEQUENCE: 22

Gln Leu Arg Asn Pro Glu Leu His Leu Gly Cys Ala Leu Ala Leu Arg
     1               5                  10                  15
    Phe Leu Ala Leu Val Ser Trp Asp Ile Pro Gly Ala Arg Ala Leu Asp
                    20                  25                  30
    Asn Gly Leu Ala Arg Thr Pro Thr Met Gly Trp Leu His Trp Glu Arg
                35                  40                  45
    Phe Met Cys Asn Leu Asp Cys Gln Glu Glu Pro Asp Ser Cys Ile Ser
     50                  55                  60
    Glu Lys Leu Phe Met Glu Met Ala Glu Leu Met Val Ser Glu Gly Trp
     65                  70                  75                  80
    Lys Asp Ala Gly Tyr Glu Tyr Leu Cys Ile Asp Asp Cys Trp Met Ala
                    85                  90                  95
    Pro Gln Arg Asp Ser Glu Gly Arg Leu Gln Ala Asp Pro Gln Arg Phe
                   100                 105                 110
    Pro His Gly Ile Arg Gln Leu Ala Asn Tyr Val His Ser Lys Gly Leu
                115                 120                 125
    Lys Leu Gly Ile Tyr Ala Asp Val Gly Asn Lys Thr Cys Ala Gly Phe
    130                 135                 140
    Pro Gly Ser Phe Gly Tyr Tyr Asp Ile Asp Ala Gln Thr Phe Ala Asp
    145                 150                 155                 160
    Trp Gly Val Asp Leu Leu Lys Phe Asp Gly Cys Tyr Cys Asp Ser Leu
                    165                 170                 175
    Glu Asn Leu Ala Asp Gly Tyr Lys His Met Ser Leu Ala Leu Asn Arg
                180                 185                 190
    Thr Gly Arg Ser Ile Val Tyr Ser Cys Glu Trp Pro Leu Tyr Met Trp
                195                 200                 205
    Pro Phe Gln Lys Pro Asn Tyr Thr Glu Ile Arg Gln Tyr Cys Asn His
                210                 215                 220
    Trp Arg Asn Phe Ala Asp Ile Asp Asp Ser Trp Lys Ser Ile Lys Ser
    225                 230                 235                 240
    Ile Leu Asp Trp Thr Ser Phe Asn Gln Glu Arg Ile Val Asp Val Ala
                    245                 250                 255
    Gly Pro Gly Gly Trp Asn Asp Pro Asp Met Leu Val Ile Gly Asn Phe
                260                 265                 270
    Gly Leu Ser Trp Asn Gln Gln Val Thr Gln Met Ala Leu Trp Ala Ile
                275                 280                 285
    Met Ala Ala Pro Leu Phe Met Ser Asn Asp Leu Arg His Ile Ser Pro
    290                 295                 300
    Gln Ala Lys Ala Leu Leu Gln Asp Lys Asp Val Ile Ala Ile Asn Gln
    305                 310                 315                 320
    Asp Pro Leu Gly Lys Gln Gly Tyr Gln Leu Arg Gln Gly Asp Asn Phe
                    325                 330                 335
    Glu Val Trp Glu Arg Pro Leu Ser Gly Leu Ala Trp Ala Val Ala Met
                340                 345                 350
    Ile Asn Arg Gln Glu Ile Gly Gly Pro Arg Ser Tyr Thr Ile Ala Val
                355                 360                 365
    Ala Ser Leu Gly Lys Gly Val Ala Cys Asn Pro Ala Cys Phe Ile Thr
            370                 375                 380
    Gln Leu Leu Pro Val Lys Arg Lys Leu Gly Phe Tyr Glu Trp Thr Ser
    385                 390                 395                 400
    Arg Leu Arg Ser Glu Lys Asp Glu Leu
                        405

<210> SEQ ID NO 23
<211> LENGTH: 30
<212> TYPE: PRT
<213> ORGANISM: Tobacco mosaic virus

<400> SEQUENCE: 23

Thr Ser Arg Leu Arg Ser His Ile Asn Pro Thr Gly Thr Val Leu Leu
     1               5                  10                  15
    Gln Leu Glu Asn Thr Met Gln Met Ser Leu Lys Asp Leu Leu
                    20                  25                  30

<210> SEQ ID NO 24
```

```
<211> LENGTH: 36
<212> TYPE: PRT
<213> ORGANISM: Tobacco mosaic virus

<400> SEQUENCE: 24

Thr Ser Arg Leu Arg Ser His Ile Asn Pro Thr Gly Thr Val Leu Leu
    1               5                   10                  15
    Gln Leu Glu Asn Thr Met Gln Met Ser Leu Lys Asp Leu Leu Ser Glu
                20                  25                  30
    Lys Asp Glu Leu
                35

<210> SEQ ID NO 25
<211> LENGTH: 26
<212> TYPE: PRT
<213> ORGANISM: Tobacco mosaic virus

<400> SEQUENCE: 25

Thr Ser Arg Leu Arg Ser His Ile Asn Pro Thr Gly Thr Val Leu Leu
    1               5                   10                  15
    Gln Leu Glu Asn Thr Met Gln Met Ser Leu
                20                  25

<210> SEQ ID NO 26
<211> LENGTH: 32
<212> TYPE: PRT
<213> ORGANISM: Tobacco mosaic virus

<400> SEQUENCE: 26

Thr Ser Arg Leu Arg Ser His Ile Asn Pro Thr Gly Thr Val Leu Leu
    1               5                   10                  15
    Gln Leu Glu Asn Thr Met Gln Met Ser Leu Ser Glu Lys Asp Glu Leu
                20                  25                  30

<210> SEQ ID NO 27
<211> LENGTH: 22
<212> TYPE: PRT
<213> ORGANISM: Tobacco mosaic virus

<400> SEQUENCE: 27

Thr Ser Arg Leu Arg Ser His Ile Asn Pro Thr Gly Thr Val Leu Leu
    1               5                   10                  15
    Gln Leu Glu Asn Thr Met
                20

<210> SEQ ID NO 28
<211> LENGTH: 29
<212> TYPE: PRT
<213> ORGANISM: Tobacco mosaic virus

<400> SEQUENCE: 28

Thr Ser Arg Leu Arg Ser His Ile Asn Pro Thr Gly Thr Thr Val Leu
    1               5                   10                  15
    Leu Gln Leu Glu Asn Thr Met Ser Glu Lys Asp Glu Leu
                20                  25

<210> SEQ ID NO 29
<211> LENGTH: 18
<212> TYPE: PRT
<213> ORGANISM: Tobacco mosaic virus

<400> SEQUENCE: 29

Thr Ser Arg Leu Arg Ser His Ile Asn Pro Thr Gly Thr Val Leu Leu
    1               5                   10                  15
    Gln Leu

<210> SEQ ID NO 30
```

```
<211> LENGTH: 24
<212> TYPE: PRT
<213> ORGANISM: Tobacco mosaic virus

<400> SEQUENCE: 30

Thr Ser Arg Leu Arg Ser His Ile Asn Pro Thr Gly Thr Val Leu Leu
    1               5                   10                  15
    Gln Leu Ser Glu Lys Asp Glu Leu
                20

<210> SEQ ID NO 31
<211> LENGTH: 5
<212> TYPE: PRT
<213> ORGANISM: Tobacco mosaic virus

<400> SEQUENCE: 31

Thr Ser Arg Leu Arg
    1               5

<210> SEQ ID NO 32
<211> LENGTH: 11
<212> TYPE: PRT
<213> ORGANISM: Tobacco mosaic virus

<400> SEQUENCE: 32

Thr Ser Arg Leu Arg Ser Glu Lys Asp Glu Leu
    1               5                   10

<210> SEQ ID NO 33
<211> LENGTH: 11641
<212> TYPE: DNA
<213> ORGANISM: Tobacco mosaic virus

<400> SEQUENCE: 33 gtattttttac aacaattacc aacaacaaca aacaacaaac aacattacaa ttactattta      60
    caattacaat ggcatacaca cagacagcta ccacatcagc tttgctggac actgtccgag     120
    gaaacaactc cttggtcaat gatctagcaa agcgtcgtct ttacgacaca gcggttgaag     180
    agtttaacgc tcgtgaccgc aggcccaagg tgaacttttc aaaagtaata agcgaggagc     240
    agacgcttat tgctaccagg cgtatccag aattccaaat tacattttat aacacgcaaa      300
    atgccgtgca ttcgcttgca ggtggattgc gatctttaga actggaatat ctgatgatgc     360
    aaattcccta cggatcattg acttatgaca taggcgggaa ttttgcatcg catctgttca     420
    agggacgagc atatgtacac tgctgtatgc ccaacctgga cgttcgagac atcatgcggc     480
    acgaaggcca gaaagacagt attgaactat acctttctag gctagagaga gggggaaaa     540
    cagtccccaa cttccaaaag gaagcatttg acagatacgc agaaattcct gaagacgctg     600
    tctgtcacaa tacttttcag acaatgcgac atcagccgat gcagcaatca ggcagagtgt     660
    atgccattgc gctacacagc atatatgaca taccagccga tgagttcggg cggcactct      720
    tgaggaaaaa tgtccatacg tgctatgccg cttttccactt ctctgagaac ctgcttcttg    780
    aagattcata cgtcaatttg gacgaaatca acgcgtgttt ttcgcgcgat gggacaagt      840
    tgacctttc ttttgcatca gagagtactc ttaattattg tcatagttat tctaatattc      900
    ttaagtatgt gtgcaaaact tacttccegg cctctaatag agaggtttac atgaaggagt     960
    ttttagtcac cagagttaat acctggtttt gtaagttttc tagaatagat acttttctt     1020
    tgtacaaagg tgtggcccat aaaagtgtag atagtgagca gttttatact gcaatggaag    1080
    acgcatggca ttacaaaaag actcttgcaa tgtgcaacag cgagagaatc ctccttgagg    1140
    attcatcatc agtcaattac tggtttccca aaatgaggga tatggtcatc gtaccattat    1200
    tcgacatttc tttggagact agtaagagga cgcgcaagga agtcttagtg tccaaggatt    1260
    tcgtgtttac agtgcttaac cacattcgaa cataccaggc gaaagctctt acatacgcaa    1320
    atgttttgtc ctttgtcgaa tcgattcgat cgagggtaat cattaacggt gtgacagcga    1380
    ggtccgaatg ggatgtggac aaatctttgt acaatccctt gtccatgacg ttttacctgc    1440
    atactaagct tgccgttcta aaggatgact tactgattag caagttttag ctcggttcga    1500
    aaacggtgtg ccagcatgtg tgggatgaga tttcgctggc gtttgggaac gcatttccct    1560
    ccgtgaaaga gaggctcttg aacaggaaac ttatcagagt ggcaggcgac gcattagaga    1620
    tcagggtgcc tgatctatat gtgaccttcc acgacagatt agtgactgag tacaaggcct    1680
    ctgtggacat gcctgcgctt gacattagga gaagatgga agaaacggaa gtgatgtaca    1740
    atgcactttc agagttatcg gtgttaaggg agtctgacaa attcgatgtt gatgtttttt    1800
    cccagatgtg ccaatctttg gaagttgacc caatgacggc agcgaaggtt atagtcgcgg    1860
    tcatgagcaa tgagagcggt ctgactctca catttgaacg acctactgag gcgaatgttg    1920
    cgctagcttt acaggatcaa gagaaggctt cagaaggtgc tttggtagtt acctcaagag    1980
    aagttgaaga accgtccatg aaggggttcga tggccagagg agttacaa ttagctggtc     2040
    ttgctggaga tcatccggag tcgtccctatt ctaagaacga ggagatagag tctttagagc    2100
    agtttcatat ggcaacggca gattcgttaa ttcgtaagca gatgagctcg attgtgtaca    2160
    cgggtccgat taagttcag caaatgaaaa actttatcga tagcctggta gcatcactat    2220
    ctgctgcggt gtcgaatctc gtcaagatcc tcaaagatac agctgctatt gaccttgaaa    2280
```

```
cccgtcaaaa gtttggagtc ttggatgttg catctaggaa gtggttaatc aaaccaacgg   2340
ccaagagtca tgcatggggt gttgttgaaa cccacgcgag gaagtatcat gtgcgctttt   2400
tggaatatga tgagcagggt gtggtgacat gcgatgattg gagaagagta gctgtcagct   2460
ctgagtctgt tgtttattcc gacatggcga aactcagaac tctgccagag ctgcttcgaa   2520
acgagaaacc gcatgtcagt agcgcaaagg ttgttcttgt ggacggagtt ccgggctgtg   2580
ggaaaaccaa agaaattctt tccaggggta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcaacacgt   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatcc   3120
tgactttac ccaatcggat aaagaagctc tgctttcaag agggtattca gatgttcaca   3180
ctgtgcatga agtgcaaggc gagacatact ctgatgtttc actagttagg ttaaccccta   3240
caccagtctc catcattgca ggagacagcc cacatgtttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaaatagc   3420
aattacagat tgactcggtg ttcaaaggtt ccaatctttt tgttgacgcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaagatt   3600
gcatattgga tatgtctaag tctgttgctg cgcctaagga tcaaatcaaa ccactaatac   3660
ctatggtacg aacgcgcgca gaaatgccac gccagactgg actattggaa aatttagtgg   3720
cgatgattaa aaggaacttt aacgcacccg agttgtctgg catcattgat attgaaaata   3780
ctgcatcttt agttgtagat aagttttttg atagttattt gcttaaagaa aaaagaaaac   3840
caaataaaaa tgtttctttg ttcagtagag agtctctcaa tagatggtta gaaaagcagg   3900
aacaggtaac aataggccag ctcgcagatt ttgattttgt agatttgcca gcagttgatc   3960
agtacagaca catgattaaa gcacaaccca agcaaaaatt ggacacttca atccaaacgg   4020
agtacccggc tttgcagacg attgtgtacc attcaaaaaa gatcaatgca atatttggcc   4080
cgttgtttag tgagcttact aggcaattac tggacagtgt tgattcgagc agattttttgt   4140
ttttcacaag aaagacacca gcgcagattg aggatttctt cggagatctc gacagtcatg   4200
tgccgatgga tgtcttggag ctggatatat caaaatacga caaatctcag aatgaattcc   4260
actgtgcagt agaatacgag atctcggcgaa gattgggttt tgaagacttc ttgggagaag   4320
tttggaaaca agggcataga aagaccaccc tcaaggatta taccgcaggt ataaaaactt   4380
gcatctggta tcaaagaaag agcggggacg tcacgacgtt cattggaaac actgtgatca   4440
ttgctgcatg tttggcctcg atgcttccga tggagaaaat aatcaaagga gccttttgcg   4500
gtgacgatag tctgctgtac tttccaaagg gttgtgagtt tccggatgtg caacactccg   4560
cgaatcttat gtggaatttt gaagcaaaac tgtttaaaaa acagtatgga tactttgtcg   4620
gaagatatgt aatacatcac gacagaggat gcattgtgta ttacgatccc ctaaagttga   4680
tctcgaaact tggtgctaaa cacatcaagg attgggaaca cttgaggag ttcagaaggt   4740
ctctttgtga tgttgctgtt tcgttgaaca attgtgcgta ttacacacag ttggacgacg   4800
ctgtatggga ggttcataag accgcccctc caggttcgtt tgtttataaa agtctggtga   4860
agtatttgtc tgataaagtt ctttttagaa gtttgtttat agatggctct agttgttaaa   4920
ggaaaagtga atatcaaata gtttatcgac ctgacaaaaa tggagaagat cttaccgtcg   4980
atgtttaccc ctgtaaagag tgttatgtgt tccaaagttg ataaaataat ggttcatgag   5040
aatgagtcat tgtcagaggt gaaccttctt aaaaggagtta agcttattga tagtggatac   5100
gtctgtttag ccggtttggt cgtcacgggc gagtggaact tgcctgacaa ttgcagagga   5160
ggtgtgagcg tgtgtctggt ggacaaaagg atggaaagag ccgacgaggc cactctcgga   5220
tcttactaca cagcagctgc aaagaaaaga tttcagttca aggtcgttcc caattatgct   5280
ataaccaccc aggacgcgat gaaaaacgtc tggcaagttt tagttaatat tagaaatgtg   5340
aagatgtcag cgggtttctg tccgctttct ctggagtttg tgtcggtgtg tattgtttat   5400
agaaataata taaaattagg tttgagagag aagattacaa acgtgagaga cggagggccc   5460
atggaactta cagaagaagt cgttgatgag ttcatggaag atgtccctat gtcgatcagg   5520
cttgcaaagt ttcgatctcg aaccggaaaa aagagtgatg tccgcaaagg gaaaaatagt   5580
agtaatgatc ggtcagtgcc gaacaagaac tatagaaatg ttaaggattt tggaggaatg   5640
agttttaaaa agaataattt aatcgatgat gattcggagg ctactgtcgc cgaatcggat   5700
tcgttttaaa tagatcttac agtatcacta ctccatctca gttcgtgttc ttgtcattaa   5760
tatgcaggtg ctgaacacca tggtgaacaa acacttcttg tcccttttcgg tcctcatcgt   5820
cctccttggc ctctcctcca acttgacagc cggcatgctg gacaatggat tggcaaggac   5880
gcctaccatg ggctggctgc actgggagcg cttcatgtgc aaccttgact gccaggaaga   5940
gccagattcc tgcatcagtg agaagctctt catggagatg gcagagctca tggtctcaga   6000
aggctggaag gatgcaggtt atgagtacct ctgcattgat gactgttgga tggctcccca   6060
aagagattca gaaggcagac ttcaggcaga ccctcagcgc tttcctcatg ggattcgcca   6120
gctagctaat tatgttcaca gcaaaggact gaagctaggg atttatgcag atgttggaaa   6180
taaacctgc gcaggcttcc ctgggagttt tggatactac gacattgtga cccgacctt   6240
tgctgactgg ggagtagatc tgctaaaatt tgatggttgt tactgtgaca gtttggaaaa   6300
tttggcagat ggttataagc acatgtcctt ggcccgtgaat aggactggca gaagcattgt   6360
gtactcctgt gagtggcctc tttatatgtg gccctttcaa aagcccaatt atacagaaat   6420
ccgacagtac tgcaatcact ggcgaaattt tgctgacatt gatgattcct ggaaaaagtat   6480
aaagagtatc ttggactgga catcttttaa ccaggaagga attgttgatg ttgctggacc   6540
aggggggttgg aatgacccag atatgttagt gattggcaac tttgccctca gctggaatca   6600
gcaagtaact cagatggccc tctgggctat catggctgct cctttattca tgtctaatga   6660
cctccgacac atcagccctc aagccaaagc tctccttcag gataaggacg taattgccat   6720
caatcaggac cccttggcca gcaaggggta ccagcttagg caggagaca actttgaagt   6780
gtgggaacga cctctctcag gcttagcctg ggctgtagct atgataaacc ggcaggagat   6840
tggtggacct cgctcttata ccatcgcagt tgcttccctg gtaaaggag tggcctgtaa   6900
tcctgcctgc ttcatcacac agctcctccc tgtgaaaagg aagctagggt tctatgaatg   6960
gacttcaagg ttaagaagtc acataaatcc cacaggcact gttttgcttc agctatctga   7020
```

-continued

```
aaaggacgaa ttatgaccta ggctcgcaaa gtttcgaacc aaatcctcaa aaagaggtcc     7080
gaaaaataat aataatttag gtaaggggcg ttcaggcgga aggcctaaac caaaaagttt     7140
tgatgaagtt gaaaagagt ttgataattt gattgaagat gaagccgaga cgtcggtcgc      7200
ggattctgat tcgtattaaa tatgtcttac tcaatcactt ctccatcgca atttgtgttt     7260
ttgtcatctg tatgggctga ccctatagaa ttgttaaacg tttgtacaaa ttcgttaggt     7320
aaccagtttc aaacacagca agcaagaact actgttcaac agcagttcag cgaggtgtgg    7380
aaacctttcc ctcagagcac cgtcagattt cctggcgatg tttataaggt gtacaggtac    7440
aatgcagttt tagatcctct aattactgcg ttgctggggg cttttgatac taggaataga    7500
ataatcgaag tagaaaacca gcagagtccg acaacagctg aaacgttaga tgctacccgc    7560
agggtagacg acgctacggt tgcaattcgg tctgctataa ataatttagt taatgaacta    7620
gtaagaggta ctggactgta caatcagaat acttttgaaa gtatgtctgg gttggtctgg    7680
acctctgcac ctgcatctta aatgcatagg tgctgaaata taaagtttgt gtttctaaaa    7740
cacacgtggt acgtacgata acgtacagtg ttttttccctc cacttaaatc gaagggtagt   7800
gtcttggagc gcgcggagta aacatatatg gttcatatat gtccgtaggc acgtaaaaaa    7860
agcgagggat tcgaattccc ccggaacccc cggttgggc ccaggtacca attcttgaag     7920
acgaaagggc ctcgtgatac gcctattttt ataggttaat gtcatgataa taatggtttc    7980
ttagacgtca ggtggcactt ttcggggaaa tgtgcgcgga accccctattt gtttatttt    8040
ctaaatacat tcaaatatgt atccgctcat gagacaataa ccctgataaa tgcttcaata    8100
atattgaaaa aggaagagta tgagtattca acatttccgt gtcgccctta ttccctttt     8160
tgcggcattt tgccttcctg ttttgctca cccagaaacg ctggtgaaag taaaagatgc     8220
tgaagatcag ttgggtgcac gagtgggtta catcgaactg gatctcaaca gcggtaagat    8280
ccttgagagt tttcgccccg aagaacgttt tccaatgatg agcacttta aagttctgct     8340
atgtggcgcg gtattatccc gtgttgacgc cgggcaagag caactcggtc gccgcataca    8400
ctattctcag aatgacttgg ttgagtactc accagtcaca gaaaagcatc ttacggatgg    8460
catgacagta agagaattat gcagtgctgc cataaccatg agtgataaa ctgcggccaa     8520
cttacttctg acaacgatcg gaggaccgaa ggagctaacc gcttttttgc acaacatggg    8580
ggatcatgta actcgccttg atcgttggga accggagctg aatgaagcca taccaaacga    8640
cgagcgtgac accacgatgc ctgcagcaat ggcaacaacg ttgcgcaaac tattaactgg    8700
cgaactactt actctagctt cccggcaaca attaatagac tggatggagg cggataaagt    8760
tgcaggacca cttctgcgct cggcccttcc ggctggctgg tttattgctg ataaatctgg    8820
agccggtgag cgtgggtctc gcggtatcat tgcagcactg gggccagatg gtaagccctc    8880
ccgtatcgta gttatctaca cgacggggag tcaggcaact atggatgaac gaaatagaca    8940
gatcgctgag ataggtgcct cactgattaa gcattggtaa tcgtcagacc aagtttactc    9000
atatatactt tagattgatt taaaacttca tttttaattt aaaaggatct aggtgaagat    9060
ccttttgat aatctcatga ccaaaatccc ttaacgtgag ttttcgttcc actgagcgtc    9120
agacccgta gaaaagatca aaggatcttc ttgagatcct ttttttctgc gcgtaatctg    9180
ctgcttgcaa acaaaaaaac caccgctacc agcggtggtt tgtttgccgg atcaagagct     9240
accaactctt tttccgaagg taactggctt cagcagagcg cagataccaa atactgtcct    9300
tctagtgtag ccgtagttag gccaccactt caagaactct gtagcaccgc ctacatacct    9360
cgctctgcta atcctgttac cagtggctgc tgccagtggc gataagtcgt gtcttaccgg    9420
gttggactca agacgatagt taccggataa ggcgcagcgg tcgggctgaa cggggggttc    9480
gtgcacacag cccagcttgg agcgaacgac ctacaccgaa ctgagatacc tacagcgtga    9540
gctatgagaa agcgccacgc ttcccgaagg gagaaaggcg gacaggtatc cggtaagcgg    9600
cagggtcgga acaggagagc gcacgaggga gcttccaggg ggaaacgcct ggtatcttta    9660
tagtcctgtc gggtttcgcc acctctgact tgagcgtcga ttttgtgat gctcgtcagg    9720
ggggcggagc ctatggaaaa acgccagcaa cgcggccttt ttacggttcc tggccttttg    9780
ctggcctttt gctcacatgt tctttcctgc gttatcccct gattctgtgg ataaccgtat    9840
taccgccttt gagtgagctg ataccgctcg ccgcagccga acgaccgagc gcagcgagtc    9900
agtgagcgag gaagcggaag agcgcctgat gcggtatttt ctccttacgc atctgtgcgg    9960
tatttcacac cgcatatggt gcactctcac tacaatctgc tctgatgccg catagttaag   10020
ccagtataca ctccgctatc gctacgtgac tgggtcatgg ctgcgccccg acacccgcca   10080
acacccgctg acgcgccctg acgggcttgt ctgctcccgg catccgctta cagacaagct   10140
gtgaccgtct ccgggagctg catgtgtcag aggttttcac cgtcatcacc gaaacgcgcg   10200
aggcagctgc ggtaaagctc atcagcgtgg tcgtgaagcg attcacagat gtctgcctgt   10260
tcatccgcgt ccagctcgtt gagtttctcc agaagcgtta atgtctggct tctgataaag    10320
cgggccatgt taagggcggt tttttcctgt ttggtcactt gatgcctccg tgtaagggg    10380
aatttctgtt catggggta atgataccga tgaaacgaga gaggatgctc acgatacggg   10440
ttactgatga tgaacatgcc cggttactgg aacgttgtga gggtaaacaa ctggcggtat   10500
ggatgcggcg ggaccagaga aaaatcactc agggtcaatg ccagcgcttc gttaatacag   10560
atgtaggtgt tccacagggt agccagcagc atcctgcgat gcagatccgg aacataatgg   10620
tgcagggcgc tgacttccgc gtttccagac tttacgaaac acggaaaccg aagaccattc   10680
atgttgttgc tcaggtcgca gacgttttgc agcagcagtc gcttcacgtt cgctcgcgta   10740
tcggtgattc attctgctaa ccagtaaggc aaccccgcca gcctagccgg gtcctcaacg   10800
acaggagcac gatcatgcgc acccgtggcc aggacccaac gctgcccgag atgcgccgcg   10860
tgcggctgct ggagatgcg gacgcgatgg atatgttctg ccaagggttg gtttgcgcat   10920
tcacagttct ccgcaagaat tgattggctc caattcttgg agtggtgaat ccgttagcga   10980
ggtgccgccg cttccattc aggtcgaggt ggcccggctc catgcaccgc gacgcaacgc    11040
ggggaggcag acaaggtata gggcggcgcc tacaatccat gccaaccgt tccatgtgct     11100
cgccgaggcg cataaatcg ccgtgacgat cagcggtcca gtgatcgaag ttaggctggt    11160
aagagccgcg agcgatcctt gaagctgtcc ctgatggtcg tcatctacct gcctggacag   11220
catgcctgc aacgcgggca tcccgatgcc gccgaagcg agaagaatca taatggggaa     11280
ggccatccag cctcgcgtcg cgaacgccag caagacgtag cccagcgcgt cggccgccat    11340
gccggcgata atggcctgct tctcgccgaa acgtttggtg gcgggaccag tgacgaaggc   11400
ttgagcgagg gcgtgcaaga ttccgaatac cgcaagcgac aggccgatca tcgtcgcgct    11460
ccagcgaaag cggtcctcgc cgaaaatgac ccagagcgct gccgctacgag              11520
ttgcatgata aagaagacag tcataagtgc ggcgacgata gtcatgcccc gcgcccaccg   11580
gaaggagctg actgggttga aggctctcaa gggcatcggt cgagatttag gtgacactat   11640
a                                                                   11641
```

<210> SEQ ID NO 34
<211> LENGTH: 8234
<212> TYPE: DNA
<213> ORGANISM: Tobacco mosaic virus

<400> SEQUENCE: 34

```
gtatttttac aacaattacc aacaacaaca aacaacagac aacattacaa ttactattta     60
caattacaat ggcatacaca cagacagcta ccacatcagc tttgctggac actgtccgag    120
gaaacaactc cttggtcaat gatctagcaa agcgtcgtct ttacgacaca gcggttgaag    180
agtttaacgc tcgtgaccgc aggcccaagg tgaacttttc aaaagtaata agcgaggagc    240
agacgcttat tgctacccgg gcgtatccag aattccaaat tacattttat aacacgcaaa    300
atgccgtgca ttcgcttgca ggtggattgc gatctttaga actggaatat ctgatgatgc    360
aaattcccta cggatcattg acttatgaca taggcgggaa ttttgcatcg catctgttca    420
agggacgagc atatgtacac tgctgcatgc ccaacctgga cgttcgagac atcatgcggc    480
acgaaggcca gaaagacagt attgaactat acctttctag gctagagaga ggggggaaaa    540
cagtccccaa cttccaaaag gaagcatttg acagatacgc agaaattcct gaagacgctg    600
tctgtcacaa tactttccag acatgcgaac atcagccgat gcagcaatca ggcagagtgt    660
atgccattgc gctacacagc atatatgaca taccagccga tgagttcggg gcggcactct    720
tgaggaaaaa tgtccatacg tgctatgccg ctttccactt ctccgagaac ctgcttcttg    780
aagattcatg cgtcaatttg gacgaaatca acgcgtgttt ttcgcgcgat ggagacaagt    840
tgaccttttc ttttgcatca gagagtactc ttaattactg tcatagttat tctaatattc    900
ttaagtatgt gtgcaaaact tacttcccgg cctctaatag agaggtttac atgaaggagt    960
ttttagtcac cagagttaat acctggtttt gtaagttttc tagaatagat acttttcttt   1020
tgtacaaagg tgtggcccat aaaagtgtag atagtgagca gttttatact gcaatggaag   1080
acgcatggca ttacaaaaag actcttgcaa tgtgcaacag cgagagaatc ctccttgggg   1140
attcatcatc agtcaattac tggtttccca aaatgaggga tatggtcatc gtaccattat   1200
tcgacatttc tttggagact agtaagagga cgcgcaagga agtcttagtg tccaaggatt   1260
tcgtgttcac agtgcttaac cacattcgaa cataccaggc gaaagctctt acatacgcaa   1320
atgttttgtc cttcgtcgaa tcgattcgat cgagggtaat cattaacggt gtgacagcga   1380
ggtccgaatg ggatgtggac aaatctttgt tacaatcctt gtccatgacg ttttacctgc   1440
atactaagct tgccgttcta aaggatgact tactgattag caagtttagt ctcggttcga   1500
aaacggtgtg ccagcatgtg tgggatgaga tttcgctggc gtttgggaac gcatttccct   1560
ccgtgaaaga gaggctcttg aacaggaaac ttatcagagt ggcaggcgac gcattagaga   1620
tcagggtgcc tgatctatat gtgaccttcc acgacagatt agtgactgag tacaaggcct   1680
ctgtggacat gcctgcgctt gacattagga agaagatgga agaaacggaa gtgatgtaca   1740
atgcactttc agaattatcg gtgttaaggg agtctgacaa attcgatgtt gatgtttttt   1800
cccagatgtg ccaatctttg gaagttgacc caatgacggc agcgaaggtt atagtcgcgg   1860
tcatgagcaa tgagagcggt ctgactctca catttgaacg acctactgag gcgaatgttg   1920
cgctagcttt acaggatcaa gagaaggctt cagaaggtgc attggtagtt acctcaagag   1980
aagttgaaga accgtccatg aagggttcga tggccagagg agagttacaa ttagctggtc   2040
ttgctggaga tcatccggaa tcgtcctatt ctaagaacga ggagatagag tctttagagc   2100
agtttcatat ggcgacggca gattcgttaa ttcgtaagca gatgagctcg attgtgtaca   2160
cgggtccgat taaagttcag caaatgaaaa actttatcga tagcctggta gcatcactat   2220
ctgctgcggt gtcgaatctc gtcaagatcc tcaaagatac agctgctatt gaccttgaaa   2280
cccgtcaaaa gtttggagtc ttggatgttg catctaggaa gtggttaatc aaaccaacgg   2340
ccaagagtca tgcatggggt gttgttgaaa cccacgcgag gagtatcat gtggcgcttt   2400
tggaatatga tgagcagggt gtggtgacat gcgatgattg gagaagagta gctgttagct   2460
ctgagtctgt tgtttattcc gacatggcga aactcagaac tctgcgcaga ctgcttcgaa   2520
acggagaacc gcatgtcagt agcgcaaagg ttgttcttgt ggacggagtt ccgggctgtg   2580
gaaaaaccaa agaaattctt tccagggtta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcacacgct   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatcc   3120
tgacttttac ccaatcggat aaagaagctc tgctttcaag agggtattca gatgttcaca   3180
ctgtgcatga agtgcaaggc gagacatact ctgatgtttc actagttagg ttaaccccta   3240
caccggtctc catcattgca ggagacagcc cacatgtttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaatagc   3420
aattacagat tgactcggtg ttcaaaggtt ccaatctttt tgttgcagcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaagatt   3600
gcatattgga tatgtctaag tctgttgctg cacctaagga tcaaatcaaa ccactaatac   3660
ctatggtacg aacggcggca gaaatgccac gccagactgg actattggaa aatttagtgg   3720
cgatgattaa aagaaacttt aacgcacccg agttgtctgg catcattgat attgaaaata   3780
ctgcatcttt ggttgtagat aagttttttg atagttattt gcttaaagaa aaaagaaaac   3840
caaataaaaa tgtttctttg ttcagtagag agtctctcaa tagatggtta gaaaagcagg   3900
aacaggtaac aataggccag ctcgcagatt ttgattttgt ggatttgcca gcagttgatc   3960
agtacagaca catgattaaa gcacaaccca aacaaaagtt ggacacttca atccaaacgg   4020
agtaccccgc tttgcagacg attgtgtacc attcaaaaaa gatcaatgca atattcggcc   4080
cgttgtttag tgagcttact aggcaattac tggacagtgt tgattcgagc agatttttgt   4140
tttcacaaag aaagacacca gcgcagattg aggatttctt cggagatctc gacagtcatg   4200
tgccgatgga tgtcttggag ctggatatat caaaatacga caaatctcag aatgaattcc   4260
```

```
                   actgtgcagt agaatacgag atctggcgaa gattgggttt cgaagacttc ttgggagaag    4320
                   tttggaaaca agggcataga aagaccaccc tcaaggatta taccgcaggt ataaaaactt    4380
                   gcatctggta tcaaagaaag agcggggacg tcacgacgtt cattggaaac actgtgatca    4440
                   ttgctgcatg tttggcctcg atgcttccga tggagaaaat aatcaaagga gccttttgcg    4500
                   gtgacgatag tctgctgtac tttccaaagg gttgtgagtt tccggatgtg caacactccg    4560
                   cgaatcttat gtggaatttt gaagcaaaac tgtttaaaaa acagtatgga tactttgcg    4620
                   gaagatatgt aatacatcac gacagaggat gcattgtgta ttacgatccc ctaaagttga    4680
                   tctcgaaact tggtgctaaa cacatcaagg attgggaaca cttggaggag ttcagaaggt    4740
                   ctctttgtga tgttgctgtt tcgttgaaca attgtgcgta ttacacacag ttggacgacg    4800
                   ctgtatggga ggttcataag accgcccctc caggttcgtt tgtttataaa agtctggtga    4860
                   agtatttgtc tgataaagtt cttttttagaa gtttgtttat agatggctct agttgttaaa    4920
                   ggaaaagtga atatcaatga gtttatcgac ctgacaaaaa tggagaagat cttaccgtcg    4980
                   atgtttaccc ctgtaaagag tgttatgtgt tccaaagttg ataaataat ggttcatgag    5040
                   aatgagtcat tgtcaggggt gaaccttctt aaaggagtta agcttattga tagtggatac    5100
                   gtctgtttag ccggtttggt cgtcacgggc gagtggaact tgcctgacaa ttgcagagga    5160
                   ggtgtgagcg tgtgtctggt ggacaaaagg atggaaagag ccgacgagct cattctcgga    5220
                   tcttactaca cagcagctgc aaagaaaaga tttcagttca aggtcgttcc caattatgct    5280
                   ataaccaccc aggacgcgat gagaaacgtc tggcaagttt tagttaatat tagaaatgtg    5340
                   aagatgtcag cgggtttctg tccgctttct ctggagtttg tgtcggtgtg tattgtttat    5400
                   agaaataata taaaattagg tttgagagag aagattacaa acgtgagaga cggagggccc    5460
                   atggaactta cagaagaagt cgttgatgag ttcatggaag atgtccctat gtcgatcagg    5520
                   cttgcaaagt ttcgatctcg aaccggaaaa aagagtgatg tccgcaaagg gaaaaatagt    5580
                   agtagtgatc ggtcagtgcc gaacaagaac tatagaaatg ttaaggattt tggaggaatg    5640
                   agttttaaaa agaataattt aatcgatgat gattcggagg ctactgtcgc cgaatcggat    5700
                   tcgttttaaa tagatcttac agtatcacta ctccatctca gttcgtgttc ttgtcattaa    5760
                   ttaaaatgca gctgaggaac ccagaactac atctgggctg cgcgcttgcg cttcgcttcc    5820
                   tggccctcgt ttcctgggac atccctgggg ctagagcact ggacaatgga ttggcaagga    5880
                   cgcctaccat gggctggctg cactgggagc gcttcatgtg caaccttgac tgccaggaag    5940
                   agccagattc ctgcatcagt gagaagctct tcatggagat ggcgagctc atggtctcag    6000
                   aaggctggaa ggatgcaggt tatgagtacc tctgcattga tgactgttgg atggctcccc    6060
                   aaagagattc agaaggcaga cttcaggcag accctcagcg ctttcctcat gggattcgcc    6120
                   agctagctaa ttatgttcac agcaaaggac tgaagctagg gatttatgca gatgttggaa    6180
                   ataaaacctg cgcaggcttc cctgggagtt tgggatacta cgacattgat gcccagacct    6240
                   ttgctgactg gggagtagat ctgctaaaat ttgatggttg ttactgtgac agtttggaaa    6300
                   atttggcaga tggttataag cacatgtcct tggccctgaa taggactggc agaagcattg    6360
                   tgtactcctg tgagtggcct ctttatatgt ggcccttca aaagcccaat tatacagaaa    6420
                   tccgacagta ctgcaatcac tggcgaaatt ttgctgacat tgatgattcc tggaaaagta    6480
                   taaagagtat cttggactgg acatctttta accaggagag aattgttgat gttgctggac    6540
                   caggggttg gaatgaccca gatatgttag tgattggcaa ctttggcctc agctggaatc    6600
                   agcaagtaac tcagatggcc ctctgggcta tcatggctgc tccttttattc atgtctaatg    6660
                   acctccgaca catcagccct caagccaaag ctctccttcg ggataaggac gtaattgcca    6720
                   tcaatcagga ccccttgggc aagcaagggt accagcttag acagggagac aactttgaag    6780
                   tgtgggaacg acctctctca ggcttagcct gggctgtagc tatgataaac cggcaggaga    6840
                   ttggtggacc tcgctcttat accatcgcag ttgcttccct gggtaaagga gtggcctgta    6900
                   atcctgcctg cttcatcaca cagctcctcc ctgtgaagg gaagctaggg ttctatgaat    6960
                   ggacttcaag gttaagaagt cacataaatc ccacaggcac tgtttgctt cagctatctg    7020
                   aaaaggacga attatgacct agggggtagt caagatgcat aataaataac ggattgtgtc    7080
                   cgtaatcaca cgtggtgcgt acgataacgc atagtgtttt tccctccact taaatcgaag    7140
                   ggttgtgtct tggatcgcgc gggtcaaatg tatatggttc atatacatcc gcaggcacgt    7200
                   aataagcga ggggttcggg tcgaggtcgg ctgtgaaact cgaaaaggtt ccggaaaaca    7260
                   aaaaagagag tggtaggtaa tagtgttaat aataagaaaa taaataatag tggtaagaaa    7320
                   ggtttgaaag ttgaggaaat tgaggtaaat gtaagtgatg acgagtctat cgcgtcatcg    7380
                   agtacgtttt aatcaatatg ccttatacaa tcaactctcc gagccaattt gtttacttaa    7440
                   gttccgttca tgcagtcct gtgcagctga tcaatctgtg tacaaatgca ttgggtaacc    7500
                   agtttcaaac gcaacaagct aggacaacag tccaacagca atttgcggat gcctggaaac    7560
                   ctgtgcctag tatgacagtg agatttcctg catcggattt ctatgcgtat agatataatt    7620
                   cgacgcttga tccgttgatc acggcgttat taaatagctt cgatactaga aatagaataa    7680
                   tagaggttga taatcaaccc gcaccgaata ctactgacga cgttaacgcg actcagaggg    7740
                   tagacgatgc gactgtagct ataagggctt caatcaataa tttggctaat gaactggttc    7800
                   gtgaactgg catgttcaat caagcaagct ttgagactgc tagtggactt gtctggacca    7860
                   caactccggc tacttagcta ttgttgtgag atttcctaaa ataaagtcac tgaagactta    7920
                   aaattcaggg tggctgatac caaaatcagc agtggttgtt cgtccactta aatataacga    7980
                   ttgtcatatc tggatccaac agttaaacca tgtgatggtg tatactgtgg tatggcgtaa    8040
                   aacaacggaa aagtcgctga agacttaaaa ttcagggtgg ctgataccaa aatcagcagt    8100
                   ggttgttcgt ccacttaaaa ataacgattg tcatatctgg atccaacagt taaaccatgt    8160
                   gatggtgtat actgtggtat ggcgtaaaac aacggagagg ttcgaatcct cccctaaccg    8220
                   cgggtagcgg ccca                                                        8234
```

<210> SEQ ID NO 35
<211> LENGTH: 11
<212> TYPE: PRT
<213> ORGANISM: Tobacco mosaic virus
<220> FEATURE:
<223> OTHER INFORMATION: Xaa = any amino acid

<400> SEQUENCE: 35

Xaa Xaa Pro Xaa Ile Pro Lys Ser Phe Gly Tyr

-continued

```
<210> SEQ ID NO 36
<211> LENGTH: 11
<212> TYPE: PRT
<213> ORGANISM: Tobacco mosaic virus

<400> SEQUENCE: 36

Ala Arg Pro Cys Ile Pro Lys Ser Phe Gly Tyr
    1               5                   10

<210> SEQ ID NO 37
<211> LENGTH: 6
<212> TYPE: PRT
<213> ORGANISM: Rice

<400> SEQUENCE: 37

Ser Glu Lys Asp Glu Leu
    1               5
```

PRODUCTION OF LYSOSOMAL ENZYMES IN PLANTS BY TRANSIENT EXPRESSION

RELATED APPLICATIONS

This present application is a continuation of U.S. application Ser. No. 09/993,059, filed Nov. 13, 2001, which is a continuation-in-part of U.S. application Ser. No. 09/626,127, filed Jul. 26, 2000.

FIELD OF THE INVENTION

This invention is in the field of therapeutic peptides. Specifically this invention relates to the production of pharmaceutical peptides and proteins encoded on a recombinant plant virus or and produced by an infected plant or produced by a recombinant plant. The present invention relates especially to the production of human and animal lysosomal enzymes in plants comprising expressing the genetic coding sequence of a human or animal lysosomal enzyme in a plant expression system. The plant expression system provides for post-translational modification and processing to produce recombinant protein having enzymatic activity. The invention is demonstrated herein by working examples in which transgenic or transfected tobacco plants produce a modified human α galactosidase and a glucocerebrosidase, both of which are enzymatically active. The recombinant lysosomal enzymes produced in accordance with the invention may be used for a variety of purposes including but not limited to enzyme replacement therapy for the therapeutic treatment of lysosomal storage diseases, research for development of new approaches to medical treatment of lysosomal storage diseases, and industrial processes involving enzymatic substrate hydrolysis.

BACKGROUND OF THE INVENTION

Lysosomes, which are present in all animal cells, are acidic cytoplasmic organelles that contain an assortment of hydrolytic enzymes. These enzymes function in the degradation of internalized and endogenous macromolecular substrates. When there is a lysosomal enzyme deficiency, the deficient enzyme's undegraded substrates gradually accumulate within the lysosomes causing a progressive increase in the size and number of these organelles within the cell. This accumulation within the cell eventually leads to malfunction of the organ and to the gross pathology of a lysosomal storage disease, with the particular disease depending on the particular enzyme deficiency. More than thirty distinct, inherited lysosomal storage diseases have been characterized in humans.

Enzyme Replacement Therapy

One proven treatment for lysosomal storage diseases is enzyme replacement therapy in which an active form of the enzyme is administered directly to the patient. However, abundant, inexpensive and safe supplies of therapeutic lysosomal enzymes are not commercially available for the treatment of any of the lysosomal storage diseases. There are a large number of metabolic storage disorders known to affect man. As a group, these diseases are the most prevalent genetic abnormalities of humans, yet individually they are quite rare. One of the three major classes of these conditions, comprising the majority of patients, is the sphingolipidoses in which excessive quantities of undegraded fatty components of cell membranes accumulate because of inherited deficiencies of specific catabolic enzymes. Principal disorders in this category are Gaucher disease, Niemann-Pick disease, Fabry disease, and Tay-Sachs disease. All of these disorders are caused by harmful mutations in the genes that code for specific housekeeping enzymes within lysosomes. Thus, to be effective, enzyme replacement therapy requires that the requisite exogenous enzyme be taken up by the cells in which the materials are catabolized and that they be incorporated into lysosomes within these cells. Fabry disease is an ideal candidate for enzyme replacement therapy because the disease does not involve the central nervous system. The therapeutic enzyme does not need to be delivered across the blood-brain barrier (1, 2).

The effectiveness of enzyme replacement therapy has been dramatically documented in the treatment of patients with Gaucher disease. This condition is the most frequent of all metabolic storage disorders. It is estimated that there are 15,000 patients with this condition in the United States and about 80,000 worldwide. Soon after the enzymatic defect in Gaucher disease was established, consideration was given to the possibility of treating patients with purified α-glucocerebrosidase (3). Dr. Brady elected to use human placental tissue as the source of enzyme in order to minimize sensitizing patients to the exogenous protein. Initial studies with small amounts of glucocerebrosidase injected intravenously into patients with Gaucher disease revealed that the exogenous enzyme reduced the quantity of accumulated glucocerebroside in the liver and in the blood (4). A large-scale enzyme purification procedure was developed in order to obtain sufficient quantities for clinical efficacy trials (5). It was then learned that modifications of the terminal sugars on oligosaccharide chains of the enzyme were necessary in order to target intravenously administered enzyme to macrophages where most of the glucocerebroside is stored. Targeting to macrophages was accomplished by sequential enzymatic removal of monosaccharide residues from glucocerebrosidase resulting in mannose-terminal glucocerebrosidase (6). Administration of this glycoform of glucocerebrosidase to patients has brought about immense improvement in their condition (7–10). The modified enzyme (alglucerase) is now produced commercially by Genzyme Corporation in Cambridge, Mass., under the trade name Ceredase™. The beneficial effects of this treatment have been universally confirmed (11–13). Production of recombinant glucocerebrosidase (imiglucerase) is underway in Chinese hamster ovary (CHO) cells, and the product (Cerezyme™) is as effective as placental glucocerebrosidase (14). The experience with Gaucher treatment validates enzyme replacement therapy with a product that requires post-translational modifications.

Fabry disease is caused by deficiencies in the catalytic activity of the lysosomal enzyme α galactosidase A (Gal-A). Human Gal-A is a glycoprotein homodimer with a molecular weight of approximately 101 kDa containing 5–15% Asn-linked carbohydrate. The enzyme contains approximately equal portions of high mannose and complex type glycans. Upon isoelectric focusing, many forms of the enzyme are observed due to differences in sialylation depending on the source of the protein (tissue or plasma forms). The disease is inherited as an X-linked recessive trait. A number of specific mutations in the gene have been characterized, including partial rearrangements, splice-junction defects and point mutations. Most of these mutations are private and therefore, the gene appears to be highly mutable relative to genes encoding other housekeeping enzymes. Defects result in the accumulation of glycosphingolipid substrates, globotriaosylceramide and related glycolipids with terminal α-galactosidic linkages. Uncatabolized substrate accumulates in the plasma, vascular endothelium and various organs leading to an early demise from vascular disease of the heart, brain, and kidney, particularly in the classically affected hemizygous males. In addition to systemic disease, affected individuals often suffer from peripheral neuropathies and have characteristic angiokeratoma of the skin. Heterozygous female carriers may have a more attenuated range of disease phenotypes (1,2).

Exploratory trials of enzyme replacement therapy for Fabry disease have demonstrated the biochemical effectiveness of this approach (15–18). Repeated injections of purified splenic and plasma Gal-A reduced the level of plasma substrate and may have mobilized stored tissue substrate into circulation. No immunological complications were apparent in repeated infusions of enzyme into hemizygous males. Further investigations have not been attempted because of the great difficulty in obtaining sufficient quantities of enzyme for a meaningful replacement trial. The availability of large quantities of enzyme would enable optimization of glycoforms for therapeutic efficacy by improving cell targeting and prolonging the half-life in circulation and target organs.

α Galactosidase

In the early 1970's, several investigators demonstrated the existence of two .α-Galactosidase isozymes designated A and B, which hydrolyzed the α-galactosidic linkages in 4-MU-and/or rho-NP-α-D-galactopyranosides (62, 63, 64, 65, 66, 67, 68, 69) In tissues, about 80%–90% of total α-Galactosidase (α-Gal) activity was due to a thermolabile, myoinositol-inhibitable α-Gal A isozyme, while a relatively thermostable, α-Gal B, accounted for the remainder. The two "isozymes" were separable by electrophoresis, isoelectric focusing, and ion exchange chromatography. After neuraminidase treatment, the electrophoretic migrations and pI value of α-Gal A and B were similar (70), initially suggesting that the two enzymes were the differentially glycosylated products of the same gene. The finding that the purified glycoprotein enzymes had similar physical properties including subunit molecular weight (about 46 kDa), homodimeric structures, and amino acid compositions also indicated their structural relatedness (70. 71. 72. 73. 74. 75. 76. 77). However, the subsequent demonstration that polyclonal antibodies against α-Gal A or B did not cross-react with the other enzyme (78, 79) that only α-Gal A activity was deficient in hemizygotes with Fabry disease (80) and that the genes for α-Gal A and B mapped to different chromosomes (Desnick, et al., 1989, in The Metabolic Basis of Inherited Disease, Scriver, C. R., Beaudet, A. L. Sly, W. S. and Valle, D., eds, pp. 1751–1796, McGraw Hill, New York; deGroot, et al., 1978, Hum. Genet. 44:305–312), clearly demonstrated that these enzymes were genetically distinct.

α-Gal a and Fabry Disease

In Fabry disease, a lysosomal storage disease resulting from the deficient activity of α-Gal A, identification of the enzymatic defect in 1967 (Brady, et al., 1967, N. Eng. J. Med. 276:1163) led to the first in vitro (Dawson, et al., 1973, Pediat. Res. 7: 694–690m) and in vivo (Mapes, et al., 1970, Science 169:987) therapeutic trials of α-Gal A replacement in 1969 and 1970, respectively. These and subsequent trials (Mapes, et al., 1970, Science 169:987; Desnick, et al., 1979, Proc. Natl. Acad. Sci. USA 76: 5326; and, Brady, et al., 1973, N. Engl. J. Med. 289: 9) demonstrated the biochemical effectiveness of direct enzyme replacement for this disease. Repeated injections of purified splenic and plasma α-Gal A (100,000 U/injection) were administered to affected hemizygotes over a four month period (Desnick, et al., 1979, Proc. Natl. Acad. Sci. USA 76:5326). The results of these studies demonstrated that (a) the plasma clearance of the splenic form was 7 times faster than that of the plasma form (10 min vs 70 min); (b) compared to the splenic form of the enzyme, the plasma form effected a 25-fold greater depletion of plasma substrate over a markedly longer period (48 hours vs 1 hour); (c) there was no evidence of an immunologic response to six doses of either form, administered intravenously over a four month period to two affected hemizygotes; and (d) suggestive evidence was obtained indicating that stored tissue substrate was mobilized into the circulation following depletion by the plasma form, but not by the splenic form of the enzyme. Thus, the administered enzyme not only depleted the substrate from the circulation (a major site of accumulation), but also possibly mobilized the previously stored substrate from other depots into the circulation for subsequent clearance. These studies indicated the potential for eliminating, or significantly reducing, the pathological glycolipid storage by repeated enzyme replacement. However, the biochemical and clinical effectiveness of enzyme replacement in Fabry disease has not been commercially available due to the lack of sufficient human enzyme for adequate doses and longterm evaluation.

The α-Gal A Enzyme

The α-Gal A human enzyme has a molecular weight of approximately 101,000 Da. On SDS gel electrophoresis it migrates as a single band of approximately 49,000 Da indicating the enzyme is a homodimer (Bishop & Desnick, 1981, J. Biol. Chem. 256: 1307). α-Gal A is synthesized as a 50,500 Da precursor containing phosphorylated endoglycosidase H sensitive oligosaccharides. This precursor is processed to a mature form of about 46,000 Da within 3–7 days after its synthesis. The intermediates of this processing have not been defined (Lemansky, et al., 1987, J. Biol. Chem. 262:2062). As with many lysosomal enzymes, .α.-Gal A is targeted to the lysosome via the mannose-6-phosphate receptor. This is evidenced by the high secretion rate of this enzyme in mucolipidosis II cells and in fibroblasts treated with $NH_4Cl$.

The enzyme has been shown to contain 5–15% Asn linked carbohydrate (Ledonne, et al., 1983, Arch. Biochem. Biophys. 224:186). The tissue form of this enzyme was shown to have about 52% high mannose and 48% complex type oligosaccharides. The high mannose type coeluted, on Biogel chromatography, with $Man_{8-9}$ GlcNAc while the complex type oligosaccharides were of two categories containing 14 and 19–39 glucose units. Upon isoelectric focusing many forms of this enzyme are observed depending on the sources of the purified enzyme (tissue vs plasma form). However, upon treatment with neuraminidase, a single band is observed (pI-5.1) indicating that this heterogeneity is due to different degrees of sialylation (Bishop & Desnick, 1981, J. Biol. Chem. 256:1307). Initial efforts to express the full-length cDNA encoding α-Gal A involved using various prokaryotic expression vectors (Hantzopoulos and Calhoun, 1987, Gene 57:159; Ioannou, 1990, Ph.D. Thesis, City University of New York). Although microbial expression was achieved, as evidenced by enzyme assays of intact *E. coli* cells and growth on melibiose as the carbon source, the human protein was expressed at low levels and could not be purified from the bacteria. These results indicate that the recombinant enzyme was unstable due to the lack of normal glycosylation and/or the presence of endogenous cytoplasmic or periplasmic proteases.

Gaucher Disease and Treatment

Gaucher disease is the most common lysosomal storage disease in humans, with the highest frequency encountered in the Ashkenazi Jewish population. About 5,000 to 10,000 people in the United States are afflicted with this disease (Grabowski, 1993, Adv. Hum. Genet. 21:377–441). Gaucher disease results from a deficiency in glucocerebrosidase (hGCB); glucosylceramidase; acid β-glucosidase; EC 3.2.1.45). This deficiency leads to an accumulation of the enzyme's substrate, glucocerebroside, in reticuloendothelial cells of the bone marrow, spleen and liver, resulting in significant skeletal complications such as bone marrow expansion and bone deterioration, and also hypersplenism, hepatomegaly, thrombocytopenia, anemia and lung complications (Grabowski, 1993, supra; Lee, 1982, Prog. Clin. Biol. Res. 95:177–217; Brady et al., 1965, Biochem. Biophys. Res. Comm. 18:221–225). hGCB replacement therapy has revolutionized the medical care and management of Gaucher disease, leading to significant improvement in the quality of life of many Gaucher patients (Pastores et al., 1993, Blood 82:408–416; Fallet et al., 1992, Pediatr. Res. 31:496–502). Studies have shown that regular, intravenous administration of specifically modified hGCB (Ceredase.™., Genzyme Corp.) can result in dramatic improvements and even reversals in the hepatic, splenic and hematologic manifestations of the disease (Pastores et al., 1993, supra; Fallet: et al., 1992, supra; Figueroa et al., 1992, N. Eng. J. Med 327:1632–1636; Barton et al., 1991, N. Eng. J. Med. 324:1464–1470; Beutler et al., 1991, Blood 78:1183–1189). Improvements in associated skeletal and lung complications are possible, but require larger doses of enzyme over longer periods of time.

Despite the benefits of hGCB replacement therapy, the source and high cost of the enzyme seriously restricts its availability. Until recently, the only commercial source of purified hGCB has been from pooled human placentae, where ten to twenty kilograms (kg) of placentae yield only 1 milligram (mg) of enzyme. From five hundred to two thousand kilograms of placenta (equivalent to 2,000–8,000 placentae) are required to treat each patient every two weeks. Current costs for hGCB replacement therapy range from $55 to $220/kg patient body weight every two weeks, or from $70,000 to $300,000/year for a 50 kg patient. Since the need for therapy essentially lasts for the duration of a patient's life, costs for the enzyme alone may exceed $15,000,000 during 30 to 70 years of therapy.

A second major problem associated with treating Gaucher patients with glucocerebrosidase isolated from human tissue (and perhaps even from other animal tissues) is the risk of exposing patients to infectious agents which may be present in the pooled placentae, e.g., human immuno-deficiency virus (HIV), hepatitis viruses, and others.

Accordingly, a new source of hGCB is needed to effectively reduce the cost of treatment and to eliminate the risk of exposing Gaucher patients to infectious agents.

Hurler Syndrome and Treatment

Hurler syndrome is the most common of the group of human lysosomal storage disorders known as the mucopolysaccharidosis (MPS) involving an inability to degrade dermatan sulfate and heparan sulfate. Hurler patients are deficient in the lysosomal enzyme, α-L-iduronidase (IDUA), and the resulting accumulation of glucosaminoglycans in the lysosomes of affected cells leads to a variety of clinical manifestations (Neufeld & Ash well, 1980, The Biochemistry of Glycoproteins and Proteoglycans, ed. W. J. Lennarz, Plenum Press, N.Y.; pp. 241–266) including developmental delay, enlargement of the liver and spleen, skeletal abnormalities, mental retardation, coarsened facial features, corneal clouding, and respiratory and cardiovascular involvement. Hurler/Scheie syndrome (MPS I H/S) and Scheie syndrome (MPS IS) represent less severe forms of the disorder but also involve deficiencies in IDUA. Molecular studies on the genes and cDNAs of MPS I patients has led to an emerging understanding of genotype and clinical phenotype (Scott et al., 1990, Am. J. Hum. Genet. 47:802–807). In addition, both a canine and feline form of MPS I have been characterized (Haskins et al., 1979, Pediat. Res. 13:1294–1297; Haskins and Kakkis, 1995, Am. J. Hum. Genet. 57:A39 Abstr. 194; Shull et al., 1994, Proc. Natl. Acad. Sci. USA, 91:12937–12941) providing an effective in vivo model for testing therapeutic approaches.

The efficacy of enzyme replacement in the canine model of Hurler syndrome using human IDUA generated in CHO cells was recently reported (Kakkis et al., 1995, Am. J. Hum. Genet. 57:A39 (Abstr.); Shull et al., 1994, supra). Weekly doses of approximately 1 mg administered over a period of 3 months resulted in normal levels of the enzyme in liver and spleen, lower but significant levels in kidney and Lungs and very low levels in brain, heart, cartilage and cornea (Shull et al., 1994, supra. Tissue examinations showed normalization of lysosomal storage in the liver, spleen and kidney, but no improvement in heart, brain and corneal tissues. One dog was maintained on treatment for 13 months and was clearly more active with improvement in skeletal deformities, joint stiffness, corneal clouding and weight gain (Kakkis et al., 1995, supra. A single higher-dose experiment was quite promising and showed detectable IDUA activity in the brain and cartilage in addition to tissues which previously showed activity at the lower does. Additional higher-dose experiments and trials involving longer administration are currently limited by availability of recombinant enzyme. These experiments underscore the potential of replacement therapy for Hurler patients and the severe constraints on both canine and human trials due to limitations in recombinant enzyme production using current technologies.

Lysosomal Enzymes: Biosynthesis and Targeting

Lysosomal enzymes are synthesized on membrane-bound polysomes in the rough endoplasmic reticulum. Each protein is synthesized as a larger precursor containing a hydrophobic amino terminal signal peptide. This peptide interacts with a signal recognition particle, an 11S ribonucleoprotein, and thereby initiates the vectoral transport of the nascent protein across the endoplasmic reticulum membrane into the lumen (Erickson, et al., 1981, J. Biol. Chem. 256:11224; Erickson, et al., 1983, Biochem. Biophys. Res. Commun. 115:275; Rosenfeld, et al., 1982, J. Cell Biol. 93:135). Lysosomal enzymes are cotranslationally glycosylated by the en bloc transfer of a large preformed oligosaccharide, glucose-3, mannose-9, N-acetylglucosamine-2, from a lipid-linked intermediate to the Asn residue of a consensus sequence Asn-X-Ser/Thr in the nascent polypeptide (Kornfeld, R. & Kornfeld, S., 1985, Annu. Rev. Biochem. 54:631). In the endoplasmic reticulum, the signal peptide is cleaved, and the processing of the Asn-linked oligosaccharide begins by the excision of three glucose residues and one mannose from the oligosaccharide chain.

The proteins move via vesicular transport, to the Golgi stack where they undergo a variety of posttranslational modifications, and are sorted for proper targeting to specific destinations: lysosomes, secretion, plasma membrane. During movement through the Golgi, the oligosaccharide chain on secretory and membrane glycoproteins is processed to the sialic acid-containing complex-type. While some of the oligosaccharide chains on lysosomal enzymes undergo similar processing, most undergo a different series of modifications. The most important modification is the acquisition of phosphomannosyl residues which serve as an essential component in the process of targeting these enzymes to the lysosome (Kaplan, et al., 1977, Proc. Natl. Acad. Sci. USA 74:2026). This recognition marker is generated by the sequential action of two Golgi enzymes. First, N-acetylglucosaminyl-phosphotransferase transfers N-acetylglucosamine-1-phosphate from the nucleotide sugar uridine diphosphate-N-acetylglucosamine to selected mannose residues on lysosomal enzymes to give rise to a phosphodiester intermediate (Reitman & Kornfeld, 1981, J. Biol. Chem. 256:4275; Waheed, et al., 1982, J. Biol. Chem. 257:12322). Then, N-acetylglucosamine-1-phosphodiester α-N-acetylglucosaminidase removes N-acetylglucosamine residue to expose the recognition signal, mannose-6-phosphate (Varki & Kornfeld, 1981, J. Biol. Chem. 256: 9937; Waheed, et al., 1981, J. Biol. Chem. 256:5717).

Following the generation of the phosphomannosyl residues, the lysosomal enzymes bind to mannose-6-phosphate (M-6-P) receptors in the Golgi. In this way the lysosomal enzymes remain intracellular and segregate from the proteins which are destined for secretion. The ligand-receptor complex then exits the Golgi via a coated vesicle and is delivered to a prelysosomal staging area where dissociation of the ligand occurs by acidification of the compartment (Gonzalez-Noriega, et al., 1980, J. Cell Biol. 85: 839). The receptor recycles back to the Golgi while the lysosomal enzymes are packaged into vesicles to form primary lysosomes. Approximately, 5–20% of the lysosomal enzymes do not traffic to the lysosomes and are secreted presumably, by default. A portion of these secreted enzymes may be recaptured by the M-6-P receptor found on the cell surface and be internalized and delivered to the lysosomes (Willingham, et al., 1981, Proc. Natl. Acad. Sci. USA 78:6967).

Two mannose-6-phosphate receptors have been identified. A 215 kDa glycoprotein has been purified from a variety of tissues (Sahagian, et al., 1981, Proc. Natl. Acad. Sci. USA, 78:4289; Steiner & Rome, 1982, Arch. Biochem. Biophys. 214:681). The binding of this receptor is divalent cation independent. A second M-6-P receptor also has been isolated which differs from the 215 kDa receptor in that it has a requirement for divalent cations. Therefore, this receptor is called the cation-dependent (M-6-P.sup.CD) while the 215 kDa one is called cation-independent (M-6-P.sup.CI). The M-6-P.sup.CD receptor appears to be an oligomer with three subunits with a subunit molecular weight of 46 kDa.

Biosynthesis of Lysosomal Enzymes.

Although many lysosomal enzymes are soluble and are transported to lysosomes by M-6-P receptors (MPR), integral membrane and membrane-associated proteins such as human glucocerebrosidase (hGCB) are targeted and transported to lysosomes independent of the M-6-P/MPR system (Kornfeld & Mellman, 1989, Erickson et al., 1985). hGCB does not become soluble after translation, but instead becomes associated with the lysosomal membrane by means which have not been elucidated (von Figura & Hasilik, 1986, Annu. Rev. Biochem. 55:167–193; Kornfeld and Mellman, 1989, Annu. Rev. Cell Biol. 5:483–525). hGCB is synthesized as a single polypeptide (58 kDa) with a signal sequence (2 kDa) at the amino terminus. The signal sequence is co-translationally cleaved and the enzyme is glycosylated with a heterogeneous group of both complex and high-mannose oligosaccharides to form a precursor. The glycans are predominately involved in protein conformation. The "high mannose" precursor, which has a molecular weight of 63 KDa, is post-translationally processed in the Golgi to a 66 KDa intermediate, which is then further modified in the lysosome to the mature enzyme having a molecular weight of 59 KDa (Jonsson et al., 1987, Eur. J. Biochem. 164:171; Erickson et al., 1985, J. Biol. Chem., 260:14319).

The mature hGCB polypeptide is composed of 497 amino acids and contains five N-glycosylation amino acid consensus sequences (Asn-X-Ser/Thr). Four of these sites are normally glycosylated. Glycosylation of the first site is essential for the production of active protein. Both high-mannose and complex oligosaccharide chains have been identified (Berg-Fussman et al., 1993, J. Biol. Chem. 268:14861–14866). hGCB from placenta contains 7% carbohydrate, 20% of which is of the high-mannose type (Grace & Grabowski, 1990, Biochem. Biophys. Res. Comm. 168:771–777). Treatment of placental hGCB with neuraminidase (yielding an asialo enzyme) results in increased clearance and uptake rates by rat liver cells with a concomitant increase in hepatic enzymatic activity (Furbish et al., 1981, Biochim. Biophys. Acta 673:425–434). This glycan-modified placental hGCB is currently used as a therapeutic agent in the treatment of Gaucher's disease. Biochemical and site-directed mutagenesis studies have provided an initial map of regions and residues important to folding, activator interaction, and active site location (Grace et al., 1994, J. Biol. Chem. 269:2283–2291).

The complete complementary DNA (cDNA) sequence for hGCB has been published (Tsuji et al., 1986, J. Biol. Chem. 261:50–53; Sorge et al., 1985, Proc. Natl. Acad. Sci. USA 82:7289–7293), and E. coli containing the hGCB cDNA sequence cloned from fibroblast cells, as described (Sorge et al., 1985, supra), is available from the American Type Culture Collection (ATCC) (Accession No. 65696).

Recombinant methodologies have the potential to provide a safer and less expensive source of lysosomal enzymes for replacement therapy. However, production of active enzymes, e.g., hGCB, in a heterologous system requires correct targeting to the ER, and appropriate N-linked glycosylation at levels or efficiencies that avoid ER-based degradation or aggregation. Since mature lysosomal enzymes must be glycosylated to be active, bacterial systems cannot be used. For example, hGCB expressed in E. coli is enzymatically inactive (Grace & Grabowski, 1990, supra).

Active monomers of hGCB have been purified from insect cells (Sf9 cells) and Chinese hamster ovary (CHO) cells infected or transfected, respectively, with hGCB cDNA (Grace & Grabowski, 1990, supra; Grabowski et al., 1989, Enzyme 41:131–142). A method for producing recombinant hGCB in CHO cell cultures and in insect cell cultures was recently disclosed in U.S. Pat. No. 5,236,838. Recombinant hGCB produced in these heterologous systems had an apparent molecular weight ranging from 64 to 73 kDa and contained from 5 to 15% carbohydrate (Grace & Grabowski, 1990, supra; Grace et al., 1990, J. Biol. Chem. 265:6827–6835). These recombinant hGCBs had kinetic properties identical to the natural enzyme isolated from human placentae, as based on analyses using a series of substrate and transition state analogues, negatively-charged lipid activators, protein activators (saposin C), and mechanism-based covalent inhibitors (Grace et al., 1994, supra; Berg-Fussman et al., 1993, supra; Grace et al., 1990, J. Biol. Chem. 265:6827–6835; Grabowski et al., 1989, supra). However, both insect cells and CHO cells retained most of the enzyme rather than secreting it into the medium, significantly increasing the difficulty and cost of harvesting the pure enzyme (Grabowski et al., 1989, supra). Accordingly, a recombinant system is needed that can produce human or animal lysosomal enzymes in an active form at lower cost, and that will be appropriately targeted for ease of recovery.

Enormous Costs of Pharmaceutical Enzyme Production

While the clinical treatment of Gaucher patients provides a dramatically successful example of an effective therapy, the expense underscores an equally inadequate production technology. For example, the present cost for the first year of treatment for a severely affected 70 kg patient with Gaucher disease can reach $382,000. If the patient's clinical parameters are not restored to normal in that time, treatment at this level of expense will be prolonged before dose reduction can be initiated. Even with dose reduction, it is likely that the maintenance cost for such an individual will be in the range of $135,000 per year (at $3.70/IU). Many patients are unable to pay this large cost, and health carriers are extremely reluctant to underwrite this treatment for the life of these patients. Cerezyme™ is as expensive as Ceredase™ and at this time is available only in limited quantities. The number of patients with Gaucher disease in the US currently receiving therapy is estimated to be only 10–15% of the total. According an article in Nature Medicine, since the introduction of this therapy six years ago the cost of treating Gaucher patients worldwide will soon approach one billion dollars (19). Although the total number of patients worldwide who would benefit from therapy is not known with any certainty, it is safe to assume that at least 80% of the world Gaucher population remain untreated. To quote from the NIH Technology Assessment Conference Summary Statement, Feb. 27–Mar. 1, 1995. "As a prototype for all rare diseases, the plight of patients with Gaucher disease raises difficult financial and ethical issues, which we as a society must address (20)." Fabry disease is estimated to occur at a frequency of 1 in 40,000. Over 400 hemizygous male patients have been clinically described. It is imperative that fundamentally new methods of enzyme production be developed to reduce these costs so that all who suffer from these rare disorders can be treated.

Mammalian Lysosomes Versus Plant Vacuoles

Because plants are eukaryotes, plant expression systems have advantages over prokaryotic expression systems, particularly with respect to correct processing of eukaryotic gene products. However, unlike animal cells, plant cells do not possess lysosomes. Although the plant vacuole appears functionally analogous to the lysosome, plants do not contain MPRs (Chrispeels, 1991, Ann. Rev. Pl. Phys. Pl. Mol. Biol. 42:21–53; Chrispeels and Tague, 1991, Intl. Rev. Cytol. 125:1–45), and the mechanisms of vacuolar targeting can differ significantly from those of lysosomal targeting. For example, the predominant mechanism of vacuolar targeting in plants does not appear to be glycan-dependent, but appears to be based instead on C- or N-terminal peptide sequences (Gomez & Chrispeels, 1993, Plant Cell 5:1113–1124; Chrispeels & Raikhal, 1992, Cell 68:613–618; Holwerda et al., 1992, Plant Cell 4:307–318; Neuhaus et al., 1991, Proc. Natl. Acad. Sci. USA 88:10362–10366; Chrispeels, 1991, supra; Chrispeels & Tague, 1991, supra; Holwerda et al., 1990, Plant Cell 2:1091–1106; Voelker et al., 1989, Plant Cell 1:95–104). As a result, plants have not been viewed as appropriate expression systems for lysosomal enzymes which must be appropriately processed to produce an active product.

An object of this invention is to provide the existing patient population with enough active enzyme to develop a lower cost treatment. The enzymatic, structural, and glycan compositional analyses show rGal to be active. There are recent advances in glycoprotein modification and drug delivery that allow, as examples, the chemical conjugation of peptides to carbohydrate, the covalent addition of polyethylene glycol to enzymes and the liposomal encapsulation of protein. Many additional new concepts can be tested to increase the half-life of enzymes in circulation and optimize cellular and subcellular targeting. Ideally, these modifications will require a facile and rapid genetic system to produce large quantities of highly pure enzyme and an effective animal disease model for drug development. Our lab-scale process appears highly scalable and is capable of producing grams of enzyme per month in existing indoor greenhouse growth areas.

Using a viral transfection system and transgenic plants, we have expressed enzymes in plants that have potential as therapeutic agents for humans with the metabolic storage disorders known as Fabry disease and Gaucher disease. High specific activity recombinant enzymes were secreted by tobacco leaf cells via a default pathway of protein sorting into the apoplastic compartment, a network of extracellular space, cell wall matrix materials and intercellular fluid (IF). We further developed a novel bioprocessing method to purify these enzymes from the IF fraction.

Another object of this invention is to provide an optimized preproenzyme amino acid (AA) sequence for secretion of highly active lysosomal enzymes. Another object of this invention is to provide an optimized purification of lysosomal enzymes from either the IF fraction or from whole plant homogenates. Another object of this invention is to provide a molecular characterization of the enzymes purified by this process, including determination of enzyme specific activity.

SUMMARY OF THE INVENTION

The present invention provides for a polypeptide comprising (a) the complete, or a fragment of, the amino acid sequence of α-galactosidase with or without (b) an ER-retention signal, such as the amino acid sequence SEKDEL (SEQ ID NO:37), wherein the ER-retention signal is at the carboxy end of the complete, or a fragment of, the amino acid sequence of α-galactosidase, wherein said fragment of the amino acid sequence of α-galactosidase comprises a deletion of at the carboxy end of α-galactosidase, wherein said deletion is one to twenty-five amino acids. The present invention also provides for a polynucleotide encoding the aforementioned polypeptide.

The present invention also relates to the production of these human or animal lysosomal enzymes, including the aforementioned polypeptides, in transformed or transfected plants, plant cells or plant tissues, and involves constructing and expressing recombinant expression constructs comprising lysosomal enzyme coding sequences in a plant expression system. The plant expression system provides appropriate co-translational and post-translational modifications of the nascent peptide required for processing, e.g., signal sequence cleavage, glycosylation, and sorting of the expression product so that an enzymatically active protein is produced. Using the methods described herein, recombinant lysosomal enzymes are produced in plant expression systems from which the recombinant lysosomal enzymes can be isolated and used for a variety of purposes.

The present invention is exemplified by virally transfected and transgenic tobacco plants with lysosomal enzyme expression constructs. One construct comprises a nucleotide sequence encoding a modified human glucocerebrosidase (hGCB). Another construct comprises nucleotide sequence encoding a human α galactosidase (α gal or α gal A). Virally transfected and transgenic tobacco plants having the expression constructs produce lysosomal enzymes that are enzymatically active and have high specific activity.

The plant expression systems and the recombinant lysosomal enzymes produced therewith have a variety of uses, including but not limited to: (1) the production of enzymatically active lysosomal enzymes for the treatment of lysosomal storage diseases; (2) the production of altered or mutated proteins, enzymatically active or otherwise, to serve as precursors or substrates for further in vivo or in vitro processing to a specialized industrial form for research or therapeutic uses, such as to produce a more effective therapeutic enzyme; (3) the production of antibodies against lysosomal enzymes for medical diagnostic use; and (4) use in any commercial process that involves substrate hydrolysis.

BRIEF DESCRIPTION OF FIGURES

FIG. 3A shows accumulation by Western Analysis of total plant soluble extract anti human GAL-A sera.

FIG. 3B shows activity of WT rGAL-A at 8 and 14+ days post inoculation of the plant host with a viral vector.

FIG. 4A shows Western blot analysis of total plant soluble extract anti human GAL-A sera FIG. 4B shows activity of WT rGAL-wt and rGAL-wtR at 8 and 14+ days post inoculation of the plant host with a viral vector.

Figure 1:
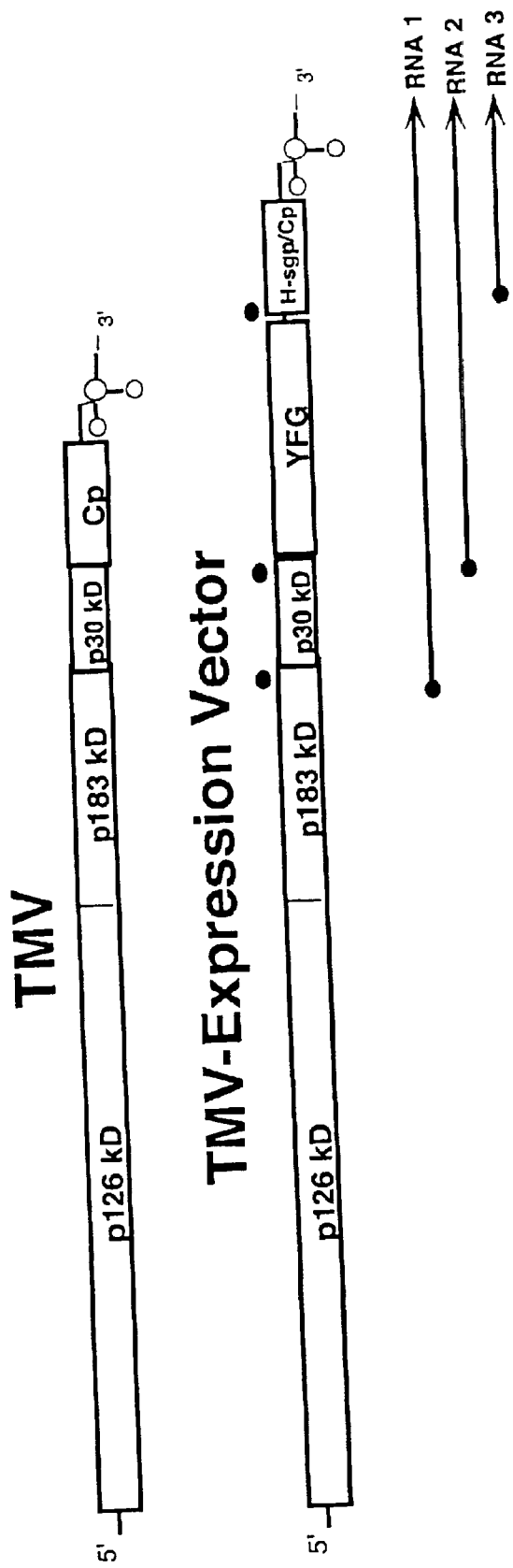
FIG. 1 shows a Tobamovirus expression vectors.
Figure 2:
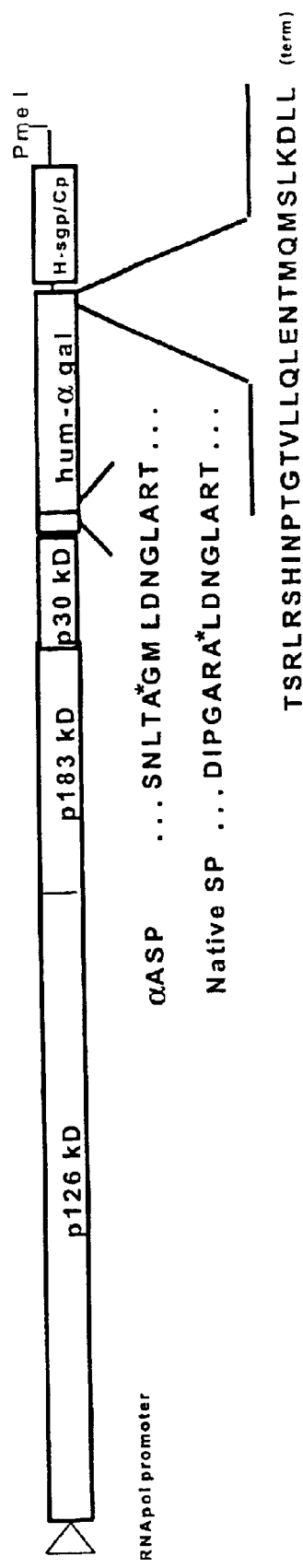
FIG. 2 shows a Tobamovirus expression vector containing the human α galactosidase gene or a variant of the gene. The amino acid sequence of αASP and Native SP depicted in FIG. 2 are depicted in SEQ ID NO: 1 and 2, respectively. The entire amino acid sequence of WT rGAL-A is depicted in SEQ ID NO: 4.
Figure 5:
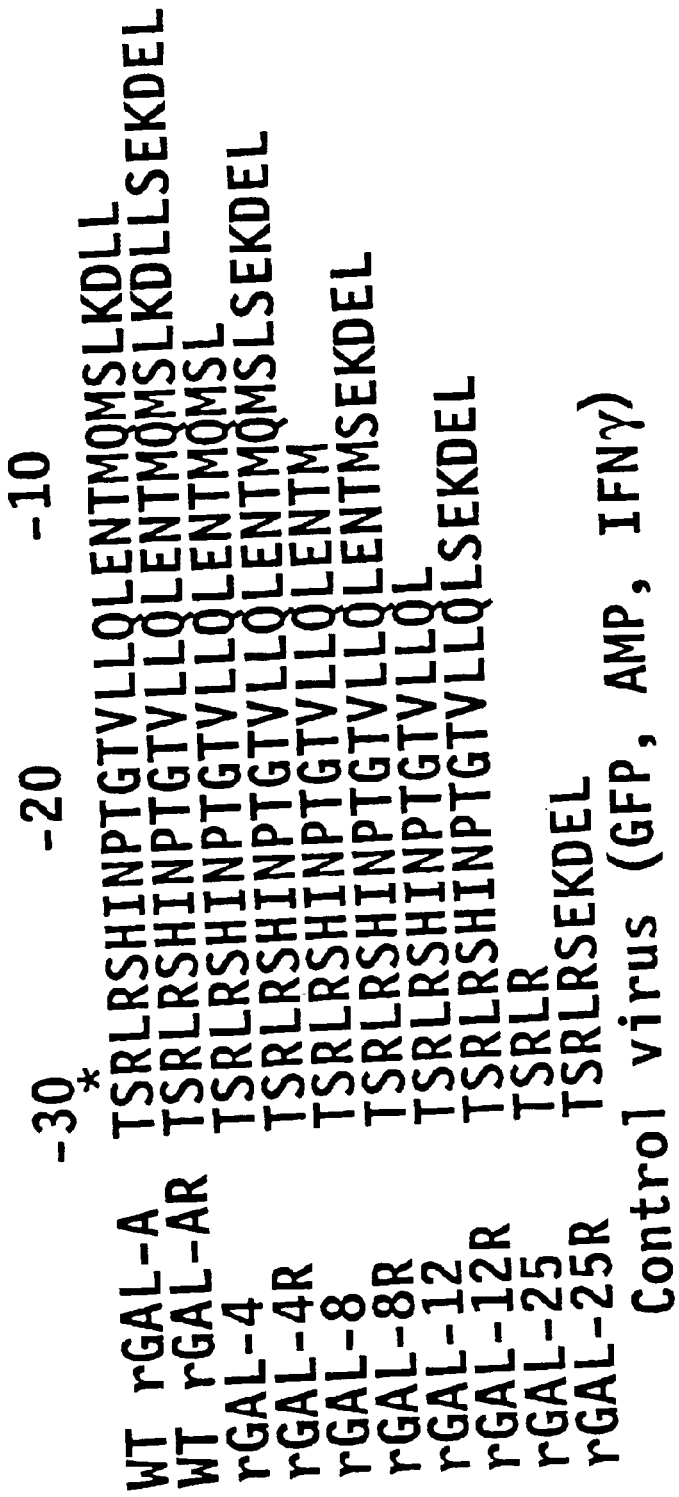
FIG. 5 shows carboxy terminal modifications to α galactosidase. The asterisk indicates a potential CTPP cleavage site according to Gene 58: 177, 1987. The entire nucleic acid and amino acid sequences of WT rGAL-A, WT-rGAL-AR, rGAL-4, rGAL-4R, rGAL-8, rGAL-8R, rGAL-12, rGAL-12R, rGAL-25, and rGAL-25R are depicted in SEQ ID NO: 3–22, respectively.

FIG. 6 shows western blot analysis of the accumulation of 10 carboxy-modified rGAL-A variants from interstitial fluid and from total plant homogenate.

FIG. 7 shows a comparison of enzymatic activity of the 10 carboxy-modified rGAL-A variants. The carboxy termini of WT-25R displayed correspond to SEQ ID NO: 23–32, respectively.

FIG. 8 shows a Coomassie blue stained electrophoresis gel separation of carboxy-modified rGAL-A variants and controls.

FIG. 9 shows a Coomassie blue stained electrophoresis gel separation of carboxy-modified rGAL-A variants and controls.

FIG. 10 shows a schematic representation of rGAL-A secretion from the endoplasmic reticulum to the apoplast.

FIG. 11 shows different glycosylation structures of *a* galactosidase.

FIGS. 12-1 thru 12-3 shows TTODA (rGAL-12R) TMV RNA begins at base 1; 126/183 reading frame begins at 69, 3417 is suppressible stop codon, and ends at 4919.30K ORF begins at 4903 and ends at 5709. Human α galactosidase A RNA begins at 5703, α amylase signal peptide is from 5762–5857; mature human α galactosidase A coding region is 5858–7036, ToMV virus coat protein and 3 UTR follows. (SEQ ID NO: 33).

FIGS. 13-1 thru 13-2 shows SBS5-rGAL-12R TMV RNA begins at base 1; 126/183 reading frame begins at 69, 3417 is suppressible stop codon, and ends at 4919.30K ORF begins at 4903 and ends at 5709. Human α galactosidase A RNA begins at 5703, complete (signal peptide and mature protein coding region) human α galactosidase A gene 5766–7037, TMV U5 virus coat protein and 3 UTR follows (SEQ ID NO: 34).

FIG. 14 shows the construct within pBSG638: a dual Cauliflower Mosiac Virus 35S promoter linked to a translational enhancer from Tobacco Etch Virus linked 5' to, and a polyadenylation region from the nopline synthase gene of *Agrobacterium tumefaciens* linked 3' to, the native human GCB cDNA.

FIG. 15 shows the construct within pBSG641: a dual Cauliflower Mosiac Virus 35S promoter linked 5' to, and a polyadenylation region from the nopline synthase gene of *Agrobacterium tumefaciens* linked 3' to, the entire genome of Tobacco Mosaic Virus except the coat protein region is replaced with the GCB gene.

DETAILED DESCRIPTION OF THE INVENTION

The present invention provides a polynucleotide comprising the nucleotide sequence depicted in SEQ ID NO:3, 5, 7, 9, 11, 13, 15, 17, 19, 31, or 32. The present invention also provides a polypeptide comprising the amino acid sequence depicted in SEQ ID NO: 4, 6, 8, 10, 12, 14, 16, 18, or 20.

The present invention further provides for a polypeptide comprising (a) the complete, or a fragment of, the amino acid sequence of α-galactosidase and (b) the amino acid SEKEL (SEQ ID NO:37), wherein SEKEL is at the carboxy end of the complete, or a fragment of, the amino acid sequence of α-galactosidase, wherein said fragment of the amino acid sequence of α-galactosidase comprises a deletion of at the carbozy end of α-galactosidase, wherein said deletion is one to twenty-five amino acids. Preferably, the deletion is one to twelve amino acids. More preferably, the deletion is four to twelve amino acids. The present invention further provides for a polynucleotide comprising a nucleotide sequence encoding the aforementioned polypeptide(s). The present invention further provides for a polypeptide comprising or consisting the amino acid sequence of rGAL-AR, rGAL-4, rGAL-4R, rGAL-8, rGAL-8R, rGAL-12, rGAL-12R, rGAL-25, or rGAL-25R.

The present invention further provides for a polynucleotide encoding the aforementioned polypeptide(s).

The present invention also provides for a viral vector or expression vector comprising the aforementioned polynucleotide(s) or encoding the aforementioned polypeptide(s). The viral vector or expression vector is capable of expression and systemic expression of the polypeptide(s) encoded by the polynucleotide in a plant cell or a plant. Preferably, the viral vector or expression vector is derived from or based on or obtained from an RNA virus or an RNA viral vector. More preferably, the RNA virus is an RNA plant virus. Even more preferably, the RNA plant virus is a single-stranded plus-sense RNA plant virus. The RNA plant virus is multi-partite, monopartite, bipartite, tripartite, or the like. Even much more preferably, the single-stranded plus-sense RNA plant virus is a tobamovrius, such as a tobacco mosaic virus.

The present invention further provides for a plant cell or a plant expressing the aforementioned polypeptide(s).

The present invention provides for a method for producing a protein of choice comprising a lysosomal enzyme which is enzymatically active, comprising: recovering the lysosomal enzyme from (i) a transgenic plant cell or (ii) a cell, tissue or organ of a transgenic plant, which transgenic plant cell or plant is transformed or transfected with a recombinant expression construct comprising a nucleotide sequence encoding the lysosomal enzyme and a promoter that regulates expression of the nucleotide sequence so that the lysosomal enzyme is expressed by the transgenic plant cell or plant.
Figure 6:
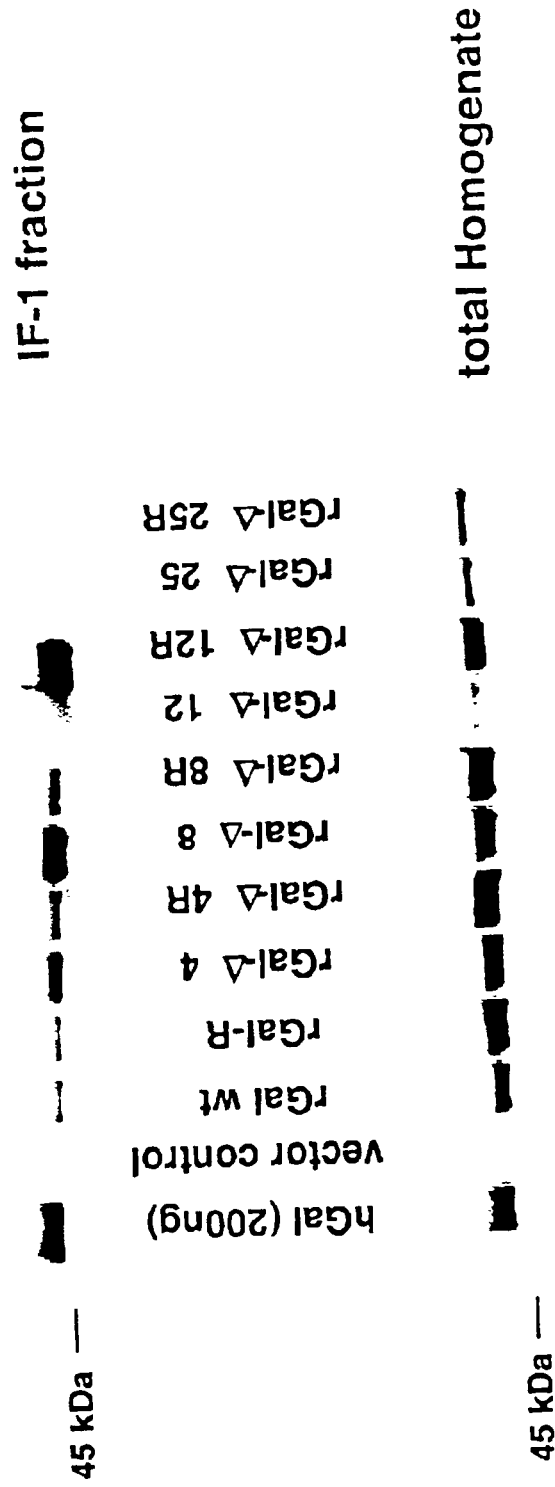
Figure 7:
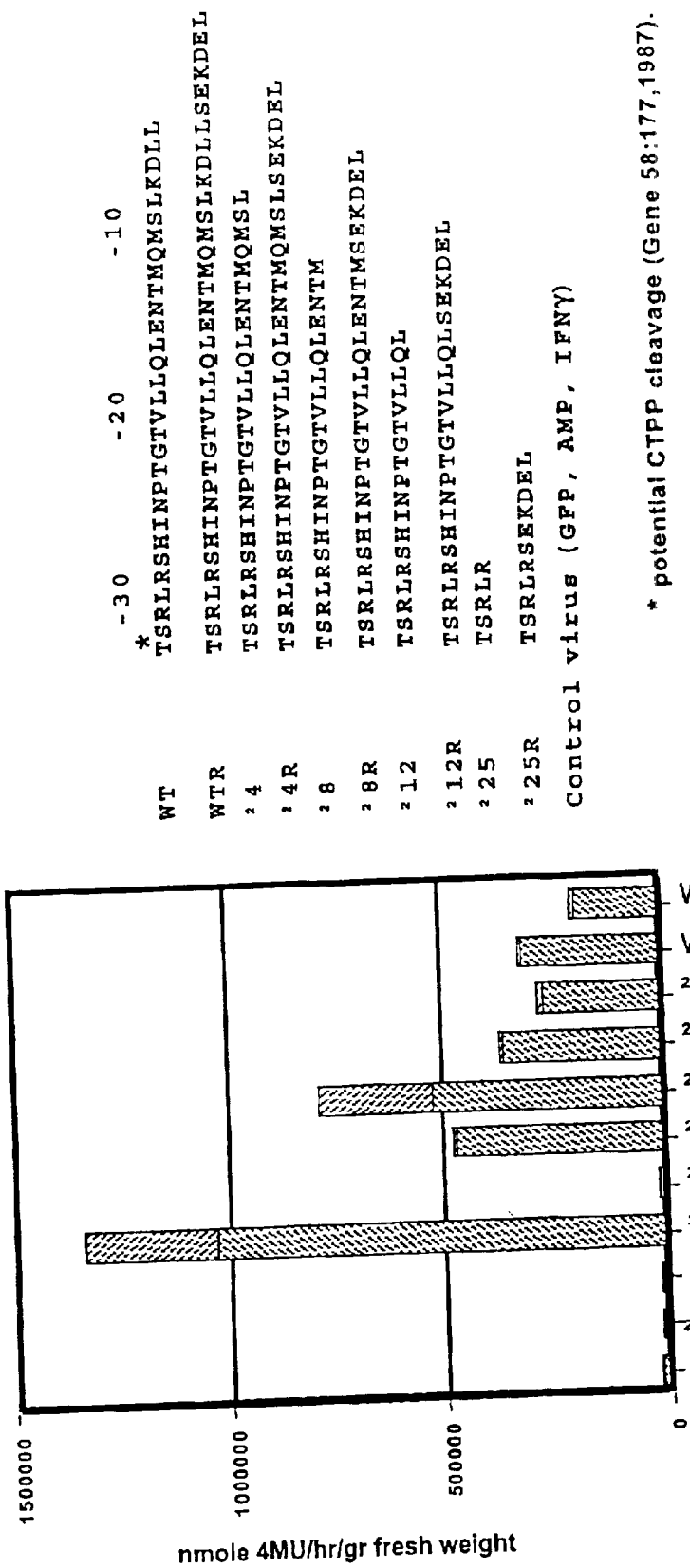
Figure 8:
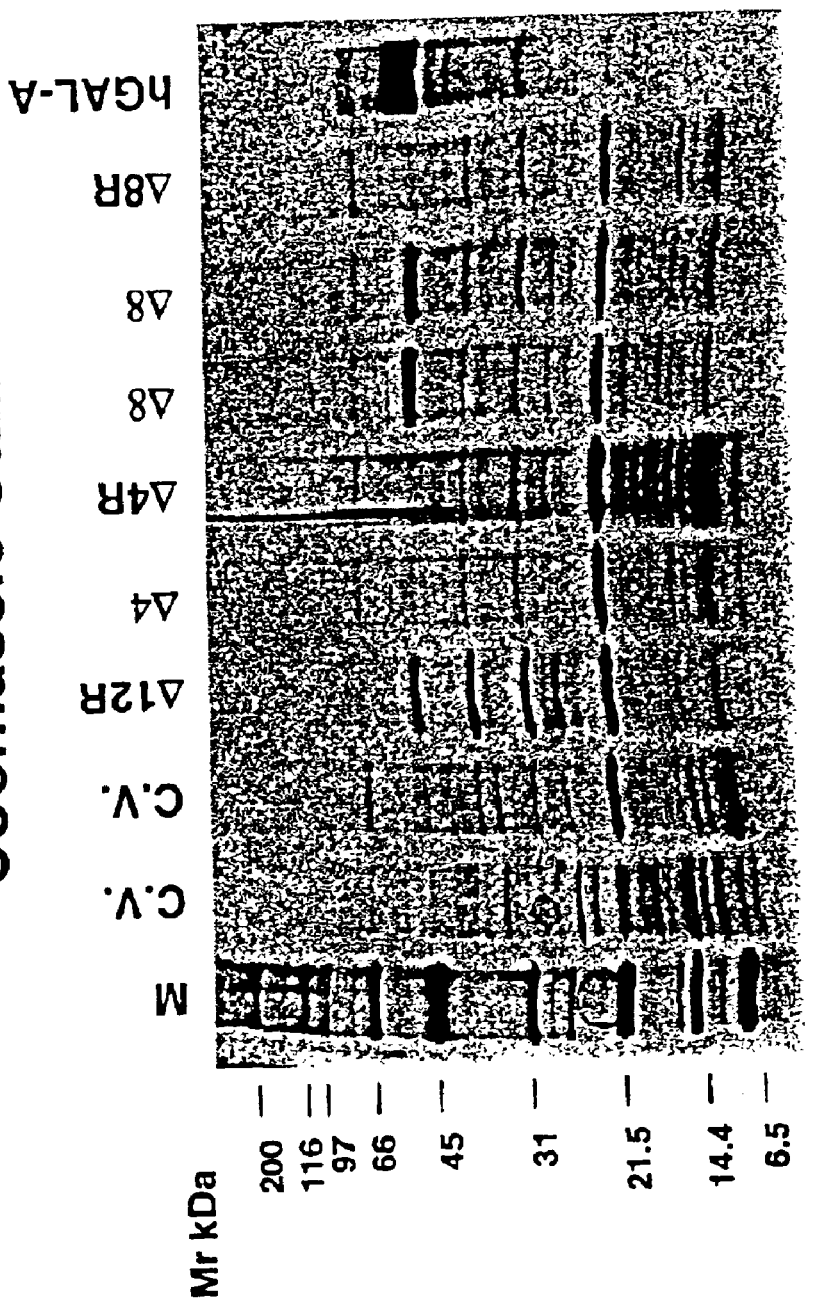
Figure 9:
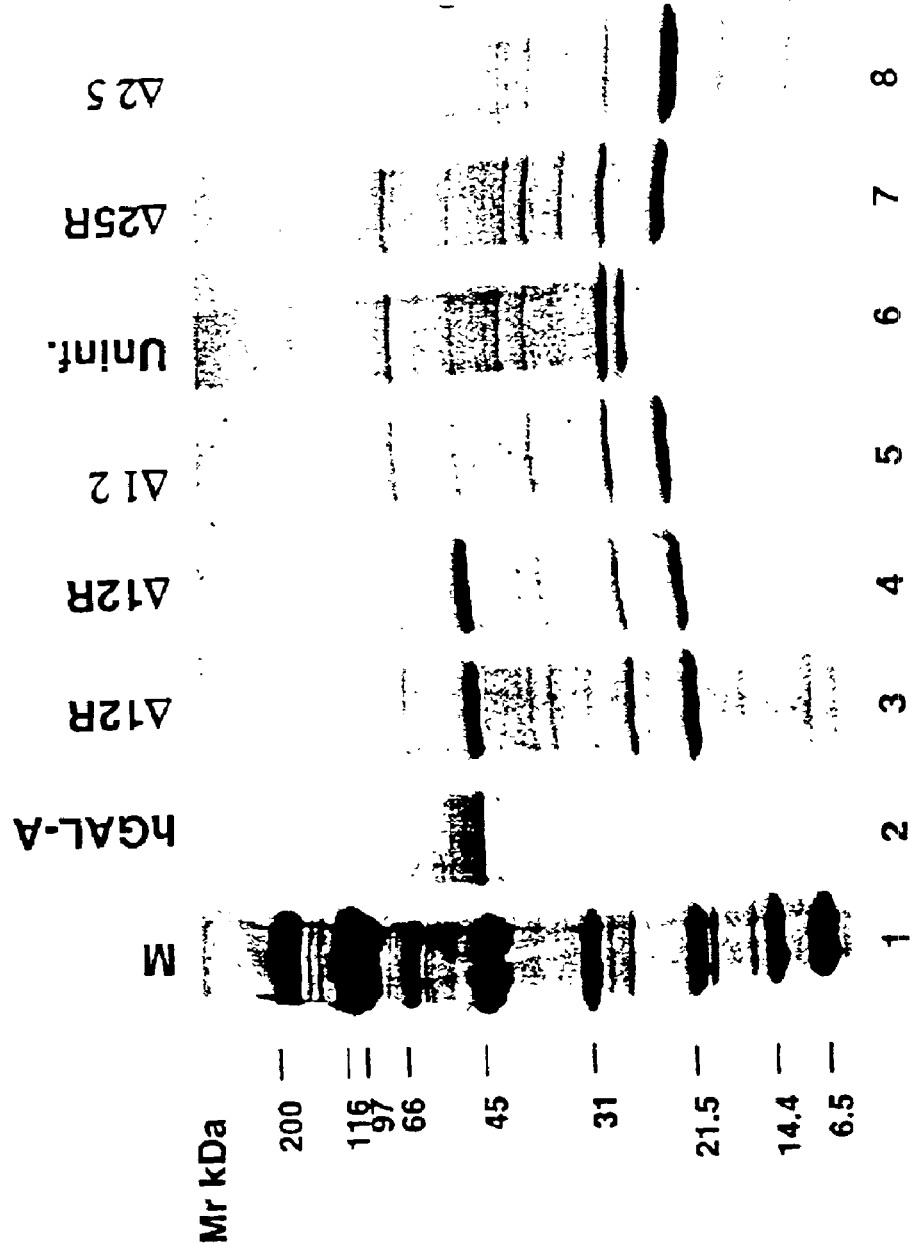
Figure 10:
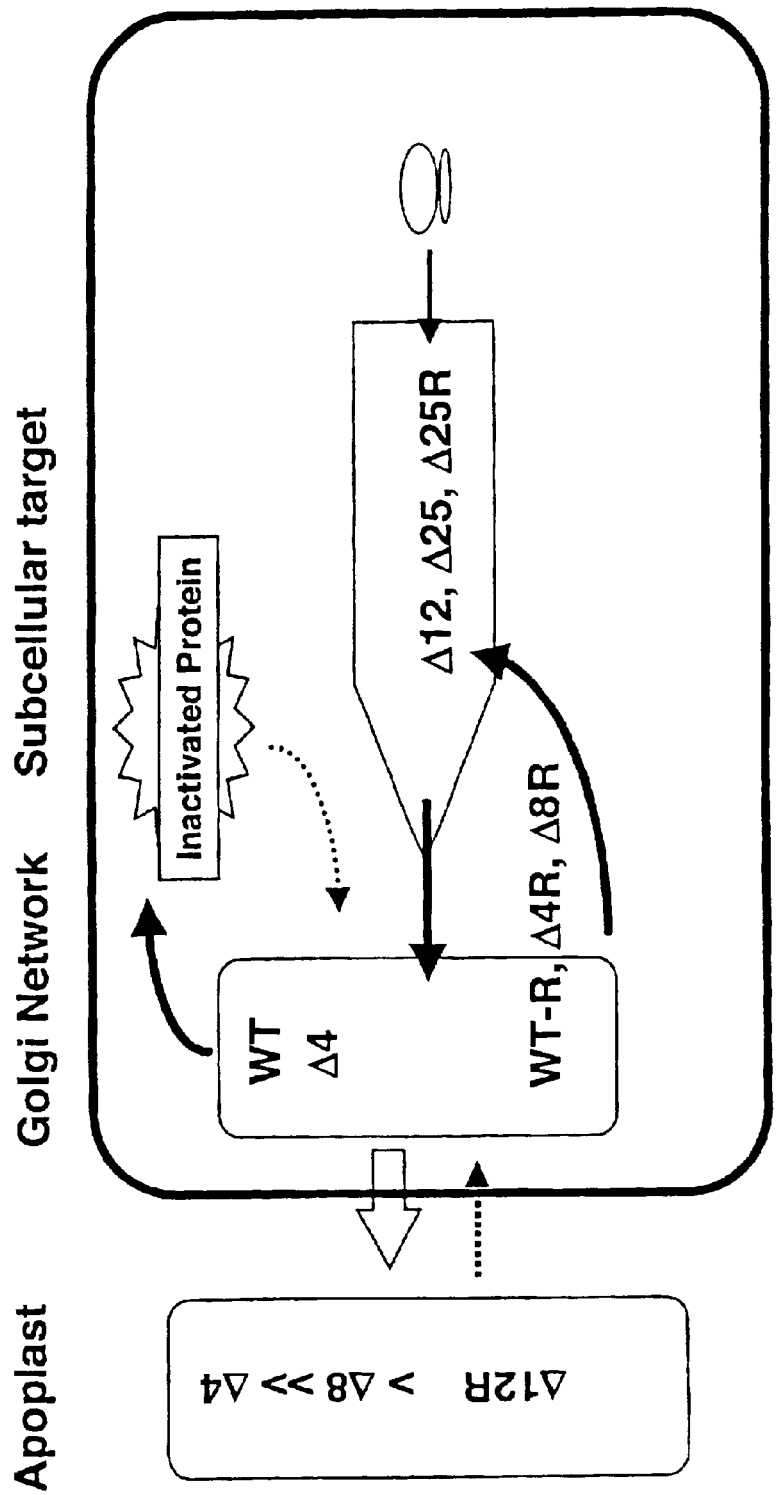
Figure 11:
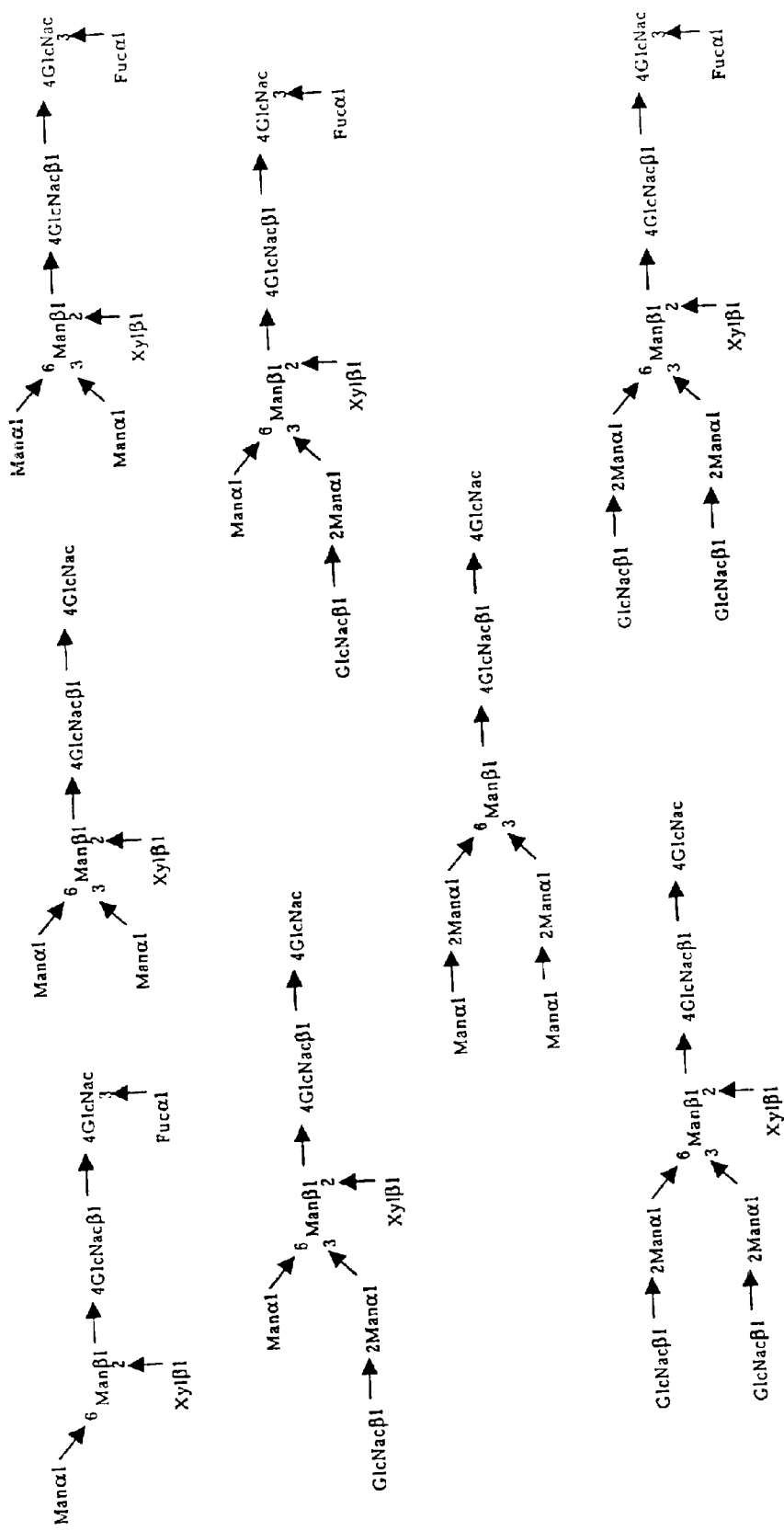

The promoter can be an inducible promoter. The inducible promoter can be induced by mechanical gene activation. The method can be carried out with the transgenic plant and additionally comprises a step of inducing the inducible promoter before or after the transgenic plant is harvested, which inducing step is carried out before recovering the lysosomal enzyme from the cell, tissue or organ of the transgenic plant.

The lysosomal enzyme can be a modified lysosomal enzyme which is enzymatically active and comprises: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions. The modified lysosomal enzyme can comprise a signal peptide or detectable marker peptide at the amino or carboxyl terminal of the modified lysosomal enzyme. The modified lysosomal enzyme can be recovered from (i) the transgenic plant cell or (ii) the cell, tissue or organ of the transgenic plant by reacting with an antibody that binds the detectable marker peptide. The antibody can be a monoclonal antibody.

The modified lysosomal enzyme can comprise: (a) an enzymatically-active fragment of an α-N-acetylgalactosaminidise, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions.

The modified lysosomal enzyme can comprise: (a) an enzymatically-active fragment of a human glucocerebrosidase or human α-L-iduronidase enzyme; (b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions.

The modified lysosomal enzyme can be a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I); and the method comprises: (a) recovering the fusion protein from the transgenic plant cell, or the cell, tissue or organ of the transgenic plant; (b) treating the fusion protein with a substance that cleaves the cleavable linker so that (1) is separated from the cleavable linker and any sequence attached thereto; and (c) recovering the separated (I).

The transgenic plant can be a transgenic tobacco plant. The lysosomal enzyme can be a human or animal lysosomal enzyme. The lysosomal enzyme can be an α-N-acetylgalactosaminidase, acid lipase, α-galactosidase, glucocerebrosidase, α-L-iduronidase, iduronate sulfatase, α-mannosidase or sialidese. The lysosomal enzyme can be a human glucocerebrosidase or human α-L-iduronidase. The organ can be a leaf, stem, root, flower, fruit or seed.

The present invention provides for a recombinant expression construct comprising a nucleotide sequence encoding a protein of choice comprising a lysosomal enzyme and a promoter that regulates the expression of the nucleotide sequence in a plant cell.

The promoter can be an inducible promoter. The inducible promoter can be induced by mechanical gene activation. The lysosomal enzyme can be a modified lysosomal enzyme which is enzymatically active and comprises: (a) an enzymatically active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions. The modified lysosomal enzyme can comprise a signal peptide or detectable marker peptide at the amino or carboxyl terminal of the modified lysosomal enzyme.

The modified lysosomal enzyme can comprise (a) an enzymatically-active fragment of an α-N-acetylgalactosaminidase, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions.

The modified lysosomal enzyme can comprise (a) an enzymatically-active fragment of a human glucocerebrosidase or human α-L-iduronidase enzyme; (b) the human glucocerebrosidase or human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions.

The modified lysosomal enzyme can be a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I). The lysosomal enzyme can be a human or animal lysosomal enzyme. The lysosomal enzyme can be an α-N-acetylgalactosaminidase, acid lipase, α-galactosidase, glucocerebrosidase, α-L-iduronidase, iduronate sulfatase, α-mannosidase or sialidase. The lysosomal enzyme can be a human glucocerebrosidase or human α-L-iduronidase.

The present invention provides for a plant transformation or transfection vector comprising any of the recombinant expression construct recited above.

The present invention provides for a plant which is transformed or transfected with any of the recombinant expression construct recited above.

The present invention provides for a plant cell, tissue or organ which is transformed or transfected with any of the recombinant expression construct recited above.

The present invention provides for a plasmid comprising any of the recombinant expression construct recited above.

The present invention provides for a transgenic plant or plant cell capable of producing a lysosomal enzyme which is enzymatically active, which transgenic plant or plant cell is transformed or transfected with a recombinant expression construct comprising a nucleotide sequence encoding a lysosomal enzyme and a promoter that regulates expression of the nucleotide sequence in the transgenic plant or plant cell. The promoter is an inducible promoter. The inducible promoter is induced by mechanical gene activation. The lysosomal enzyme which is a modified lysosomal enzyme which is enzymatically active and which comprises: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions. The modified lysosomal enzyme comprises a signal peptide or detectable marker peptide at the amino or carboxyl terminal of the modified lysosomal enzyme.

The modified lysosomal enzyme comprises: (a) an enzymatically-active fragment of an α-N-acetylgalactosaminidase, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, amannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions.

The modified lysosomal enzyme can comprise: (a) an enzymatically-active fragment of a human glucocerebrosidase or human α-L-iduronidase enzyme; (b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions.

The modified lysosomal enzyme is a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I). The transgenic plant or plant cell is a transgenic tobacco plant or tobacco cell. The lysosomal enzyme is a human or animal lysosomal enzyme. The lysosomal enzyme is an α-N-acetylgalactosaminidase, acid lipase, α-galactosidase, glucocerebrosidase, α-L-iduronidase, iduronate sulfatase, α-mannosidase or sialidase. The lysosomal enzyme is a human glucocerebrosidase or human α-L-iduronidase.

The present invention provides for a leaf, stem, root, flower or seed of any of the transgenic plant recited above.

The present invention provides for a seed of plant line *Nicotiana* sp., which seed has the ATCC Accession No. PTA-2258, deposited Jul. 25, 2000.

The present invention provides for a plant grown from the seed recited above.

The present invention provides for a lysosomal enzyme which is enzymatically active and is produced according to a process comprising: recovering the lysosomal enzyme from (i) a transgenic plant cell or (ii) a cell, tissue or organ of a transgenic plant which transgenic plant cell or plant is transformed or transfected with a recombinant expression construct comprising a nucleotide sequence encoding the lysosomal enzyme and a promoter that regulates expression of the nucleotide sequence so that the lysosomal enzyme is expressed by the transgenic plant cell or plant. The promoter can be an inducible promoter. The process is carried out with the transgenic plant and additionally can comprise a step of inducing the inducible promoter before or after the transgenic plant is harvested, which inducing step is carried out before recovering the lysosomal enzyme from the cell, tissue or organ of the transgenic plant.

The modified lysosomal enzyme which can be enzymatically active and can comprise: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid, additions, deletions or substitutions. The modified lysosomal enzyme can comprise a signal peptide or detectable marker peptide at the amino or carboxyl terminal of the modified lysosomal enzyme.

The modified lysosomal enzyme can comprise: (a) an enzymatically-active fragment of an α-N-acetylgalactosaminidase, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, amannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions.

The modified lysosomal enzyme comprises: (a) an enzymatically-active fragment of a human glucocerebrosidase or human α-L-iduronidase enzyme; (b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions. The modified lysosomal enzyme can be a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I).

The transgenic plant can be a transgenic tobacco plant. The lysosomal enzyme can be a human or animal lysosomal enzyme. The lysosomal enzyme can be an α-N-acetylgalactosaminidase, acid lipase, α-galactosidase, glucocerebrosidase, α-L-iduronidase, iduronate sulfatase, α-mannosidase or sialidase. The lysosomal enzyme can be a human glucocerebrosidase or human α-L-iduronidase. The organ can be a leaf, stem, root, flower, fruit or seed.

Gal-A is one of many proteins that require glycan site occupancy at N-linked sites to achieve proper folding and stability. The ability to successfully target the enzyme in Fabry patients is also likely to be glycosylation-dependent. This requirement presently limits the expression possibilities to eukaryotic cell types. Recombinant proteins synthesized in baculovirus and yeast expression systems are often hyperglycosylated and highly heterogeneous complicating the preparation of therapeutically effective glycoforms from these sources. The rGal-A synthesized in plants is a relatively homogeneous glycoform as analyzed by its SDS-PAGE electrophoretic mobility and comigrates with rGal-A produced purified from placenta (FIG. 3). The expression results (yield and purity) we have already presented are unprecedented in any eukaryote system for a glycosylated enzyme and are not likely to be achieved in the foreseeable future with transgenic plants or animals. "Crude" rGal-A from the leaf IF has a specific activity of over 1,000,000 U/mg of protein, whereas CHO, COS-1 and insect cell extracts and supernatants are maximally only 10–20,000 U/mg; (36,41,42).

Protein pharmaceuticals may vary over five orders of magnitude in unit value and be required in kg/year quantities. The example of Gaucher disease emphasizes the need progress in production phase research. Many additional heritable metabolic disorders, particularly those caused by dysfunctional lysosomal enzymes, might be treated by supplementation with exogenously produced enzymes. Enzyme replacement using macrophage-targeted human glucocerebrosidase has been shown to be extraordinarily beneficial for Gaucher patients. However, the cost of this treatment is very great. If the significant advances in clinical research are to be applied on a practical scale, new production technologies will be required to deliver bioproducts such as these to those in need at an affordable cost (43). No savings in Gaucher treatment costs were realized upon introduction of the recombinant CHO-cell product Cerezyme™ to replace the placental-derived Ceredase™. A significant reduction in cost requires fundamental changes in both the source of enzyme and process of purification.

While the existing treatment for Gaucher disease is safe and effective, there are potential contaminants derived from the source material that may pose serious risks. For the existing pharmaceutical products, these risks primarily include possibilities of contamination with human pathogenic viruses or peptides with potent hormonal activities such as human chorionic gonadotropin (44). These potential contaminants are not present in plant source material.

The main goal in selecting plants for expression of this protein is the potential for a radical reduction in costs. For the RNA-viral mediated synthesis of rGal-A and rGCB in plants, this is very likely to be achieved through the synergistic combination of three factors:

Complex crude extracts from various eukaryote cell production systems may be replaced with a plant leaf homogenate or IF fractions highly enriched in recombinant product.

Large-scale, sterile, cell fermentation systems and associated media, capitalization, and waste costs may be replaced with plant biomass. Production is then inexpensively scaled to the quantities desired.

The labor and time required to generate transgenic higher plants or animals may be replaced with a very rapid and simple plant transformation or plant viral transfection system.

Modem agriculture can supply a new generation of medicinal plants as a source of pharmaceuticals—a source that should be as inexpensive and readily available as our food, fiber, flavors and chemical feedstocks.

Experimental Design and Methods

Post-Translational Processing and Secretion. Protein secretion to the plant apoplast is through a default pathway. In our experience, addition of the rice α-amylase signal peptide (α-ASP) sequence at the N-terminus of several recombinant proteins is sufficient to direct the protein to the lumen of the ER in tobacco leaves. However, this is not likely to be a rate limiting step in protein accumulation and many native signal peptides may function equally well in plants. It would be most desirable to include few if any additional AA residues at the N terminus after processing. For this reason, we compared expression from the native signal peptide encoded in human Gal-A cDNA to that from the foreign α-ASP sequence.

Mutations in the carboxy-terminal domain of the Gal-A homodimer have profound effects on enzymatic activity. Several mutations occurring in individuals affected with Fabry disease map to this region. Some of these mutations have a dominant negative phenotype. When a peptide map was published on Gal-A purified from human lung, the authors noted the absence of the most carboxy-terminal predicted fragment and hypothesized the proteolytic removal of 26 or 28 AA from this region (39,40). Very recently Miyamura et al. published a study of the effects of carboxy-terminal truncations on enzymatic activity in transfected COS-1 cells (42). Between 2 and 17 AA residues were removed by introducing stop codons into a series of cDNA constructs. Relative enzyme activity, measured using 4-MUG as a substrate, first increased and then decreased as AA were removed. 12 and 17 AA constructs had no activity, while 11 was the same as wild type. A 4 AA construct yielded the highest activity at approximately 6.2× the full-length sequence. Because the precise AA sequence of the carboxy-terminus of the native human enzyme was never determined, there is insufficient information to interpret these results. The carboxy-terminal domain may affect the conformation of the active site either directly or indirectly through a proteolytic maturation step and/or assembly and subcellular localization of the active form. Furthermore, it is important to stress that it is the enzyme activity on galactose-terminal glycosphingolipids that is relevant to development of a therapeutic enzyme.

Plant proteins do not require N-linked oligosaccharides for correct sorting into vacuoles (35,37,38). Some vacuolar proteins (osmotin, thaumatin, chitinase-I, glucanase-I and a barley lectin), contain sorting information in a CTPP of 7 to 22 AA in length. For several of these proteins secreted isoforms are synthesized without a CTPP domain. In other cases, experimental deletion of the CTPP results in secretion of the recombinant protein to the IF (45–48). Sorting of Gal-A to the lysosome is likely to occur by the well-characterized mannose-6-phosphate receptor pathway in mammalian cells. We hypothesize that a redundant sorting signal may exist in this carboxy-domain that also serves to reduce enzymatic activity in the ER lumen, golgi and trans-golgi network. This signal appears to function in plant cells, presumably for vacuolar localization.

Scale-up Purification and Analysis. In order to evaluate the performance of larger scale process equipment, we designed and had built a custom basket centrifuge fixture for a laboratory low-speed centrifuge that has a capacity of approximately 1 kilogram leaf material. The sensitivity of the fluorescent 4-MUG enzyme assay allowed us to begin to evaluate enzyme purification from the leaf IF fraction using the construct rGal-A-SEKDEL. (This vector only yields approximately ⅕₀th the activity of rGal-A12-SEKDEL). Leaf tissue was transfected, harvested and infiltrated as described in Section B4 (Experimental Results). Galactosidase activity was stable in crude IF extracts and was bound to the hydrophobic interaction resin octyl sepharose, and eluted in a descending ammonium sulfate gradient. The lectin resin concanavalin-A sepharose was also effective, indicating the presence of at least one high mannose chain. The enzyme did not bind to a commercially available melibiose column (Sigma).

We have measured the enrichment provided by the affinity resin α-galactosylamine Sepharose with a C12 arm (49). Some or all of the three effective chromatography steps were combined as necessary with a size exclusion fractionation to yield highly purified enzyme(s). Because our current source of enzyme is so enriched (FIG. 3), and several of the published purification steps we have shown to be compatible with the plant IF extracts, we anticipate no problems in enzyme purification. Pure enzyme preparations were shipped to the laboratory of Drs. Roscoe Brady and Gary Murray for evaluation of enzyme activity with $^{14}C$-galactose-labeled ceramide trihexoside. These colleagues were responsible for the development of the therapeutically effective glycoform of glucocerebrosidase used to treat Gaucher disease.

We scaled up the purification of up to four candidate therapeutic enzymes as necessary in our indoor greenhouses. In our initial experiment (Table 1), 38 and 48 percent of the total rGal-A activity was recovered upon the first infiltration and centrifugation treatment (Construct rGal-A12-SEKDEL) for a yield of >50 mg of enzyme per kilogram of leaf material. Experience with the extraction of glucocerebrosidase from the IF indicates that additional enzyme is recovered in a second treatment. In these experiments one leaf was collected for each sample from each of two plants. There was consider able plant to plant variation in the level of enzyme activity (Table 1). We analyzed more carefully the accumulation of enzyme activity over time post-inoculation to optimize yields. Our facilities are more than sufficient to provide the 1 kilogram quantities of biomass necessary to purify nanomoles of enzyme for the following sequence and structural work. Sequence analysis and MALDI-TOF molecular weight determination was performed as a commercial service by Commonwealth Biotechnologies, Inc. N-terminal sequence is by the automated Edman degradation. C-terminal sequence is by carboxypeptidase digestion followed with amino acid analysis.

Full-Scale Bioprocess Pilot Plant

Macroextraction. Large-scale maceration of tissue was accomplished by a 65 hp Rietz disintegrator mill. The macerated tissue was then separated into a "green juice" fraction and a fiber fraction in a Rietz screw press. The fiber fraction was dried in a Cardwell drier. The "green juice" was then pH adjusted and heated in a dual plate-and-frame heat exchanger system with adjustable holding tube. The process of pH adjustment and heating causes the precipitation of the F1 protein complex. The protein was then clarified in a 40 hp. Westphalia SA-40 disk stack centrifuge capable of clarification of "green juice" at greater than 20 gallons per minute (GPM).

Downstream Processing. The concentrate was then pumped to Clean Room 1 that houses the primary ultrafiltration (UF) equipment. This equipment was fitted with over 1000 sq. ft. of spiral wound membranes. Typically, the UF was equipped with 100,000 kDa cut-off membranes. Virus particles are recovered in the retentate. Lower molecular weight proteins are recovered in the permeate. The permeate was fractionated by a second UF system fitted with appropriate molecular weight cut-off membranes. The retentate was processed in Clean Room 2. Virus was recovered by polyethylene glycol (PEG) precipitation and centrifugation in two Sharples vertical bowl centrifuges. Final purification of soluble proteins and peptides was accomplished on a series of chromatography systems.

Additional Facilities. The facility has other major unit processes available for the recovery and purification of plant fractions. There are two Alar diatomaceous earth, rotary vacuum filters. One of the filters was in an explosion proof area of the pilot plant that can be used for solvent extraction. The solvent extraction facility also has a biphasic solvent extractor and high efficiency distillation column. Extensive tankage was available both indoors and outdoors. Pumps, filters and other process equipment are available at the facility, allowing a large margin of flexibility while developing new processes.

Full-Scale Pilot Plant Implementation. The Bioprocess Facility has excellent supporting infrastructure. The 900 square foot laboratory was equipped with all the basic tools for biochemical and protein analyses including: electrophoresis, gel filtration, HPLC, spectrophotometry, basic chromatography, chemical analysis, and sample preparation and preservation. The full scale pilot plant has approximately 15,000 square feet of additional floor space for expansion including a high bay tower. External solvent tanks are placed in diked enclosures. Two rapid recovery, high pressure (up to 600 psi) steam generators and a large twin screw, oilless compressor are on site. A complete shop and maintenance facility was present along with walk-in cold room and walk-in freezer. Additional equipment includes a ceramic microfiltration system, a spray dryer and an array of tanks, pumps, filters, heat exchangers, and agitators.

Process equipment was fabricated and modified by a group of skilled vendors and craftsmen capable of fabricating specialized equipment designed by the company, and has excellent field experience working in large scale operations.

Infiltration System. Vacuum infiltration can be accomplished in the field or at the processing facility. Development experiments determine the necessity to infiltrate the material in the field. A vacuum tank was used as the receiver for the plant tissue after harvest by the tobacco cutter. The tissue was conveyed into a trailer-mounted tank capable of full vacuum and slurried into an infiltration buffer. The Owensboro facility has a trailer capable of carrying approximately 18,000 lb. This will translated into approximately 1,000 gallons per trip to the field. The trailer was fitted with a 2,000 gallon tank capable of full volume and evacuated by a gasoline driven vacuum pump. In harvests from 1991–1994, it was the goal of the team to have harvested biomass at the processing facility in less than 1 hour after cutting. If the tissue can be held for approximately one hour without significant loss of enzyme activity, the biomass can be brought from the field in the conventional wagon and infiltrated at the processing facility. Several large, full vacuum tanks can be employed at the facility to increase the total throughput of the plant. Two large-scale vacuum pump systems in the plant that are currently associated with the Alar rotary vacuum filters can be used for the vacuum infiltration process step.

Basket Centrifugation. The full-scale basket-type centrifuge was a discontinues batch-type system. Leaf tissue can be slurried in, dewatered as a batch, then a scraper system discharges the solids to a bottom dump. Large leaves and pieces of tissue can be handled in this manner. The potential of placing a vacuum system on the discharge side of the centrifuge was also be investigated. The centrifuge was a hydraulically driven conventional basket centrifuge with a bottom discharge and bowl dimension of 48 inches in diameter and a depth of 30 inches. Optimum loadings of the centrifuge in full-scale was determined the throughput and cycle times of this process step.

Vacuum Extraction. Vacuum extraction can be accomplished in large-scale by a web or belt-type vacuum filter system common in the food ingredient business. The "in-plant" vacuum systems could also be adapted to operate this type of filter. The plant tissue can be placed on this type of filter before or after the centrifugation step. Some damage of the biomass was anticipated during the scraper mediated discharge of the basket centrifuge. The discharged material was analyzed for the presence of intracellular components and their effect on enzyme activity, recovery and separation. These data determined the position of the vacuum filtration step in the process flow.

Downstream Processing. The initial UF separation was accomplished by an Alfa-Laval custom UF system consisting of six modular housings each containing either three 12 inch spiral wound membranes (Amicon type) or one standard 38 inch module. This yields a UF system with between 740 and 1140 square feet of membrane area of typical spiral wound configuration. The ability to interchange housings and replace housings by spool pieces gives the system great flexibility in large-scale process development. This system was housed in Clean Room #1. This room is 14×18 ft, and is under positive pressure, HEPA-filtered air. A second UF system was available in Clean Room #1. This smaller system, built by Separations Equipment Technology (SETEC), has the capacity for 320 square feet of spiral wound membrane. This system was employed for the second separation and diafiltration. It was designed for automatic diafiltration. Clean Room #2 is equipped with a Pharmacia Streamline fluid bed gel filtration system equipped with UV and refractive index monitoring equipment. This unit was available for chromatography steps.

An antiserum specific for these xylose- and fucose-containing complex glycans was especially useful in developing an ELISA assay to follow enzymatic deglycosylation. Large quantities of purified enzyme facilitate definitive determination of glycosylation structure and if necessary provide adequate rGal-A to use as substrate for enzymatic deglycosylation reactions. Using Gal-A knockout mice in the laboratory of Dr. Brady at NIH was an important genetic tool in developing a therapeutically effective glycoform. We use our transfected plants as a convenient source of recombinant enzyme for glycan analysis. Glycoforms are shown in FIG. 11.

Plants as a Source of Recombinant Pharmaceutical Proteins. A number of genetic tools have been developed during the last decade for the expression of foreign genes in plants. In addition to various antibody molecules (21–23), the accumulation of serum proteins (24) and candidate vaccine products (25–28) has been described in the leaves and other tissues of whole plants. We increased the attainable expression levels through the use of chimeric RNA viruses. For production of specific proteins, transient expression of foreign genes in plants using virus-based vectors has several advantages. These chimeric viruses move quickly from an initial infection site and deliver the recombinant gene to essentially all somatic cells of the plant. The gene vectors are premier analytical tools because they allow both high level expression and brief cycles of protein modification and testing. A permissive host provides high levels of expression and may be used for rapid, large-scale recombinant protein production in whole plants.

We validated the performance of plant-based expression systems for the production of recombinant proteins and peptides of pharmaceutical significance. In two weeks post-inoculation, the ribosome inactivating enzyme α-trichosanthin was over-produced in plants to 2% of the total soluble protein and had the same specific activity as the enzyme from the native source (29). Because these products can be obtained from a non-sterile, low input, renewable and easily scalable source, the costs of synthesis in plants are negligible. We confirmed the performance and containment of the vectors in four field trials (1991, 1994, 1995, 1996).

The vectors of the invention are based on chimeras between the 6.4 kb single-stranded RNA genome of tobacco mosaic virus (TMV) and other members of the tobamovirus group. Most of the TMV genome encodes overlapping reading frames required for replication and transcription (FIG. 1). These are located at the 5' end of the virus and translated from genomic RNA yielding proteins of 126 and 183 kDa. Expression of the internal genes was controlled by different promoters on the minus-sense RNA that direct synthesis of 3'-coterminal subgenomic mRNAs produced during replication. The 30 kDa protein, which was required for the virus to move from cell to cell, was produced early and in relatively low amounts, whereas the 17.5 kDa coat protein was produced late and usually as the most abundant protein in infected cells. Largely because of the strength of the coat protein subgenomic promoter, during peak protein synthesis the coat protein can be produced at up to 70% of the total rate of cellular protein synthesis without appreciably reducing host protein synthesis (30).

The entire cDNA of the TMV genome was cloned behind a bacterial phage promoter in an *E. coli* plasmid. Precise replicas of the virion RNA can be produced in vitro with RNA polymerase and dinucleotide cap, $m^7GpppG$. This not only allows manipulation of the viral genome for reverse genetics, but it also allows manipulation of the virus into a gene transfer vector. Subgenomic promoters from divergent viral strains can be added to the genome to direct the expression of foreign genes. Enormous quantities of mRNA are synthesized and delivered directly from the cytoplasm to the ribosome. TMV-based transient vectors offer significant advantages over integration of genes into plant chromosomes. By altering the molecular exclusion limits of the cellular junctions between adjacent plant cells, the vector invades virtually every cell of the plant during a period of 2 weeks post-inoculation. For many gene products, the recombinant protein accumulates to several percent of the total protein during this brief period of time. In contrast, it was very time consuming and labor intensive to generate, select, and breed transgenic plants for recombinant protein production. Many of these selections were culled because of poor expression due to position effects or gene silencing phenomena. In many more lines, the levels of product accumulation was too low for development of a viable commercial process.

EXAMPLE 1

We have established that a recombinant human lysosomal enzyme (rGCB) synthesized in transgenic tobacco has comparable activity to the same enzyme isolated from other native and recombinant sources. We also investigated the feasibility and economic advantages of purifying large quantities of active rGCB from plants. We designed and fabricated laboratory equipment that enabled us to optimize the key initial steps of a purification process in the laboratory using kilogram quantities of biomass from our greenhouses. We standardized a series of assays for secretory and intracellular marker enzymes in addition to rGCB assays that allowed us to monitor both lab and field expression as well as the purification process. Leaf tissue was infiltrated with a suitable extraction buffer while submerged in a large vacuum chamber, allowing the solution to reach the leaf intercellular fluid containing rGCB. The IF fraction was recovered by centrifugation in a custom collection chamber and "basket" centrifuge rotor compatible with a conventional Beckman J2-21 spindle. rGCB was trapped from the dilute IF solution by expanded bed adsorption chromatography using a hydrophobic resin and eluted with polyethylene glycol. A second ion exchange chromatography step was implemented for an overall yield of 1.7 mg/kg at 41% purity to this stage. These procedures were then scaled-up to 100 kg during several pilot-process experiments in a field trial using analogous industrial bioprocess equipment. These results are summarized in the table below. Three lots of rGCB were further purified by RP-HPLC and used for carbohydrate profiling and composition analysis. In NMR experiments we confirmed that the GCB from the plant IF contains an N-linked glycan previously reported to occur in glycoproteins isolated from plant seeds and tissue cultures. This type of chain contains the plant-specific carbohydrate linkages of α 1–2 xylose and β 1–3 fucose on the trimannosyl core.

Making Transgenic Tobacco Plants to Produce Glucocerebrosidase

Several founder plant lines for genetically stable expression of rGCB were generated and characterized. Under greenhouse conditions individual plants accumulate rGCB to at least 1.3% of the total protein in the leaf intercellular fluid as estimated from enzymatic assays. This represents a 50-fold enrichment relative to the crude lysosomal fraction of placental extracts used as the starting material for the product Ceredase™.

Figure 14:
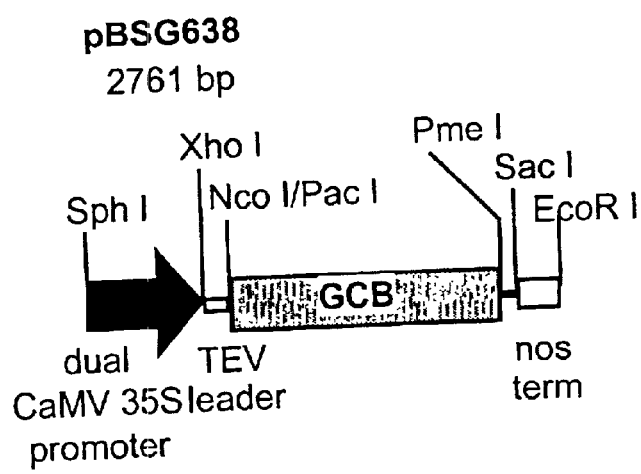
Figure 15:
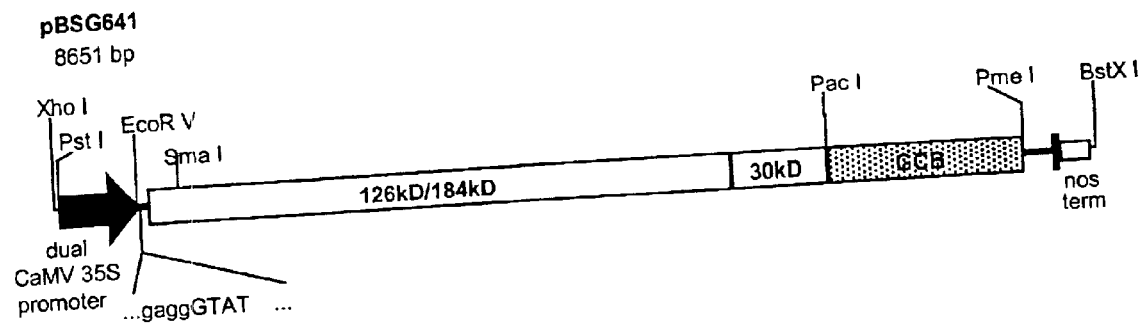

Transgenic Tobacco Leaves Express Moderate Levels of rGCB. We combined a dual promoter from Cauliflower Mosaic Virus (35S), a translational enhancer from Tobacco Etch Virus and a polyadenylation region from the nopaline synthetase gene of Agrobacterium tumefaciens with the native human GCB cDNA to create plasmid pBSG638 (33; FIG. 14). These expression elements are widely used to provide the highest possible constitutive expression of nuclear encoded genes. Depending on the nature of individual proteins, these vectors can be used to accumulate moderate levels of recombinant proteins in most tissues of many plant species.

Using a standard Agrobacterium-mediated transformation method, we regenerated 93 independent kanamycin-resistant transformants from leaf discs of four different tobacco cultivars (the T0 generation). In Western blots of total protein extracts, cross-reacting antigen was detected in 46 of these T0 individuals with antibody raised against human glucocerebrosidase. Specificity of the plant-expressed recombinant enzyme was confirmed by hydrolysis of $^{14}$C-radiolabeled glucosylceramide.

Leaf Disc Transformation with Agrobacterium tumefaciens (59, 60, 61)

Method:

1) Transform the T-DNA plasmid into A.t. LBA4404 selecting for the bacterial Ab$^R$ gene (generally Km at 100 ug/ml).

2) Pick a single colony into YEB medium plus antibiotic and grow at 28° C. overnight (to saturation; often takes a little longer than overnight).

3) Take aseptic or surface-sterilized Nicotiana tabacum (MD609, Xanthi, SR1, Samsun) leaves, remove midrib and cut into leaf "chunks" ~1 cm$^2$.

4) With sterile forceps, dip (submerge) the leaf disc into the Agrobacterium suspension.

→Placing the bacterial culture into a small petri dish is convenient.

5) Remove the leaf disc from the Agrobacterium and place the disc on regeneration medium. Place the discs so that the underside of the leaf is up. (They seem to do better this way, perhaps because of better gas transfer.)

→Use needle-nose forceps to handle the discs, thus introducing small puncture wounds into which Agrobacterium can infect; small wounds are good, major damage (e.g., crushing) to the disc is bad.

6) Seal plate containing discs with Parafilm® and incubate at 25–28° C., preferably in light with a yellow filter to inhibit UV degradation of the medium.

7) After 2 days co-incubation, transfer the leaf discs to selective plates (regeneration medium plus 500 ug/ml Cefotaxime).

8) After 2 more days, transfer discs to regeneration medium plus 500 ug/ml cefotaxime and 100 ug/ml kanamycin 9) When normal-looking shoots appear, excise them, taking care not to excise any callus, and place in rooting medium.

→Callus on the end of the stem generally prevents rooting, and could lead to a chimeric set of shoots.

→The lower % agar makes it easier to wash the agar off the roots when transferring to soil.

→If there is time, it is a good practice (when the plants are rooted and growing) to cut the shoots off and re-root them. Escapes will generally not root on Km medium.

10) When roots first appear, remove plantlets, wash agar from the roots and plant in soil medium in small pots. Cover pots with a plastic bag for the first 5 days or so to retain humidity and reduce transplantation shock.

1 Liter of Regeneration Medium contains:
MS Salts
30 g sucrose
1 ml of 0.5 mg/ml nicotinic acid
1 ml of 0.5 mg/ml pyridoxine HCl
2 ml of 0.5 mg/ml thiamine HCl
2 ml of 50 mg/ml inositol
1.5 ml of 0.1 mg/ml IAA
5.0 ml of 1.0 mg/ml 2-IP-2-iminopurine 8 g of agar, pH 6.0

1 Liter of Rooting Medium contains:

½×MS Salts 10 g sucrose 2 ml of 0.1 mg/ml IAA 8 g agar, pH 5.7

A deposit at ATCC under the Budapest Treaty was made on Jul. 25, 2000 of seed from *Nicotiana benthamiana* MD609, Accession No. PTA-2258.

According to these expression results the rGCB positive transformants were ranked into moderate (A), low (B) and negligible (C) activity groups (Table 1).

TABLE 1

EXPRESSION OF rGCB IN THE T0 GENERATION.

| Group | Number of Individuals | Specific Activity Units/mg |
|---|---|---|
| A | 13 | 130–390 |
| B | 20 | 70–130 |
| C | 13 | 24–68 |
| Controls | 8 | 0–10 |

Specific Activity is based on hydrolysis of [14 C]- glucosylceramide (Units = nmol/hr).

Plant rGCB is Similar to Macrophage-Targeted Glucocerebrosidase. We found reaction conditions to preferentially inhibit rGCB enzyme activity in the presence of plant glucosidases using the suicide substrate conduritol B-epoxide (CBE). Total glucosidase activity, and rGCB activity were measured by hydrolysis of the fluorescent substrate 4-methylumbelliferylglucopyranoside (4-MUG) with and without CBE. Total protein was determined by the method of Bradford. Detergents are necessary to solubilize and stabilize activity of this membrane-associated enzyme. Using a small scale (~100 mg fresh weight) extraction procedure, several detergents were compared for yield of enzyme activity and purity (including; IGEPAL CA-630, Tween-20, Tween-80, Triton X-100, Triton X-114, CHAPS, taurocholic acid, cholic acid, deoxycholate and taurodeoxycholate). Buffer without detergent, deoxycholate, taurocholate and cholate below their critical micelle concentrations (CMC) (0.1%) yielded low units of rGCB. All of the other detergents gave comparable specific activity and yields of total activity with Tween-80 yielding slightly higher activity. The dialyzable bile salt, sodium taurocholate and the lower CMC detergent Tween-80 were compared at a range of concentrations (0.1–1% and 0.001–1%, respectively). Tween-80 at 0.15% and taurocholate at 0.5% gave the best yield and purity.

A number of chromatography steps were evaluated for purification of rGCB from total homogenates (Table 2). As is the case for the native placental enzyme, hydrophobic resins provide the most significant purification gains. Gel filtration, Con A Sepharose and affinity chromatography also worked very well, but some of these approaches may be impractical on a large scale. Both anion and cation chromatography may prove useful, but the ideal buffer conditions for stabilization of enzyme activity remain to be determined.

TABLE 2

SUMMARY OF CHROMOTOGRAPHY RESULTS

| Column Matrix | Type | Results |
|---|---|---|
| Octyl Sepharose 4 FF | Hydrophobic | + |
| Phenyl Sepharose HP | Hydrophobic | + |
| Phenyl Sepharose 6 FF | Hydrophobic | + |
| Butyl Sepharose 4 FF | Hydrophobic | – |
| Alkyl Superose | Hydrophobic | – |
| SP Sepharose FF | Strong Cation | +/–– |
| Q Sepharose FF | Strong Anion | +/–– |
| Con A Sepharose | Lectin Affinity | +/– |
| NHS-Activated Sepharose HP | Antibody Affinity | + |
| Sephacryl S-100 HR | Gel Filtration | + |

(+) Effective increase in Specific Activity; (+/–) Needs enzyme activity stabilized; (+/––) Variable results; (–) Poor binding.

The post-translational processing of native glucocerebrosidase (GCR) in human cells is complex. Two primary translation products are derived from two in-phase start codons. These precursors, a 2:1 mixture of 60 kDa and 57 kDa proteins, are proteolytically processed to 55 kDa as they pass into the lumen of the ER. High mannose and complex glycans are subsequently added in the ER and Golgi compartments to yield 62 and 66 kDa glycoforms. Finally, exoglycosidases generate a mature 59 kDa lysosomal enzyme. Recall that glycosylation is required for both enzymatic activity and lysosomal targeting of transfused enzyme. Sialic acid, galactose, and N-acetylglucosamine residues are enzymatically removed in vitro by the sequential action of glycosidases to prepare glucocerebrosidase for therapy. The core pathway for biosynthesis and processing of N-linked complex glycans in plants appears identical to that found in animals. There are three known differences which occur later in the pathway. Sialic acid is not reported in complex glycans from plants, and the $\alpha 1–3$ fucose and $\beta 1–2$ xylose linkages are unique (34). As analyzed by SDS/PAGE, rGCB has an apparent molecular weight of 59 kDa, and comigrates with the mannose-terminal therapeutic glycoform. We have not yet detected a significant shift in mobility upon treatment with glycosidases (PNGase F, Endo H, $\alpha$ 1–3 fucosidase) in our preliminary glycosylation analysis. However, the enzyme has an apparent molecular weight increase of 4 kDa over the proteolytically processed and unglycosylated form (55 kDa) and must be glycosylated for activity. Additional digestions are in progress with a more extensive set of endo- and exoglycosidases and known plant glycoprotein controls. N-Glycosidase A is reported to hydrolyze all types of N-glycan chains from glycopeptides and glycoproteins.

The signal peptide of rGCB is processed at the correct site. A very small quantity of protein was prepared for sequence analysis by purification through Phenyl-Sepharose, ConA-Sepharose and RP-HPLC to produce a single band on SDS-PAGE comigrating with authentic glucocerebrosidase. The sequence obtained was consistent with the known sequence of processed GCR (Table 3). In this particular analysis, the first two positions were not resolved because some degradation occurred during sample preparation. Correct proteolytic cleavage of a signal peptide is also confirmed for a mouse antibody light chain molecule expressed in tobacco leaves (35).

TABLE 3

| STRUCTURE OF THE N-TERMINUS OF rGCB | |
|---|---|
| N-terminal Amino Acid Sequence | |
| X X P X I P K S F G Y | (SEQ ID NO:35) |
| rGCB from tobacco | |
| A R P C I P K S F G Y | (SEQ ID NO:36) |
| GCR human | |

Plant rGCB Accumulates in the Leaf Intercellular Fluid. We localized rGCB to the intercellular fluid of the leaf using the following simple experimental design. Leaves were removed from the plant at the petiole and slit down the midrib into two equal halves. To obtain a total cellular homogenate, one group of half-leaves was ground in the presence of 4 volumes of detergent extraction buffer (100 mM potassium phosphate pH 6, 5 mM EDTA, 10 mM β-mercaptoethanol and 0.5% w/v sodium taurocholate) with a mortar and pestle. To recover the IF, the same enzyme extraction buffer was infiltrated into the opposing group of half-leaves by submerging the tissue and applying moderate vacuum pressure. After draining off excess buffer, the undisrupted half-leaves were rolled gently in Parafilm, placed in disposable tubes and the IF collected by low-speed centrifugation. The IF fraction is quite clear and non pigmented and can be applied directly to Phenyl Sepharose hydrophobic resin.

The results of a typical experiment are shown in Table 4. The increase in specific activity corresponds to a similar increase in the amount of cross-reacting material observed in a Western blot and is therefore not an artifact of the enzyme assay in the different fractions. Furthermore, rGCB activity was very stable in crude extracts using this particular detergent buffer. The increase in specific activity can therefore be attributed to an enrichment of rGCB in the IF relative to the whole cell homogenate. The actual concentration of rGCB in the IF is likely to be much higher, because PAGE analysis of the IF fraction shows some contamination with known cytoplasmic markers. The highest specific activity we have measured in an IF sample is 20,000 U/mg. If we assume rGCB has the same specific activity as the human enzyme ($1.5\times10^6$ U/mg), this corresponds to 1.3% of the IF protein obtained by this method.

High Levels of rGCB Expression in Leaf Tissue Induce Gene Silencing. The T0 individuals described in Table 4 are by definition hemizygous. They contain various loci generated from independent insertion events, having no corresponding insert on the homologous chromosome. The thirteen T0 individuals from Group A were self-pollinated and assayed for levels of enzyme expression in the T1 generation in order to analyze the effects of gene dosage (homozygotes versus hemizygotes) and to identify candidate T1 families for future seed increase. Kanamycin-resistant transgenic plants were randomly selected from segregating families and analyzed for rGCB expression. The number of probable loci was estimated by chi-square analysis of the linked kanamycin-resistant phenotype at >95% confidence level. There are several T1 families with a heritable mean rGCB activity in the range of 200–300 U/mg (nmol 4-MUG hydrolyzed per hour) in the total homogenates that we have selected for further production of the enzyme (Table 5).

TABLE 5

EXPRESSION OF rGCB IN THE T1 GENERATION

| Tobacco Cultivar | T1 Family | Number of Loci | Mean Specific Activity Units/mg | Standard Error | Number of Individuals |
|---|---|---|---|---|---|
| Samsun | 963 | 2 | 294 | 25 | 23 |
| Samsun | 881 | 1 | 242 | 22 | 16 |
| MD609 | 920 | 1 | 205 | 15 | 38 |
| Xanthi | 902 | 1 | 202 | 17 | 5 |
| Samsun | 883 | 1 | 201 | 18 | 13 |
| Xanthi | 832 | 1 | 195 | 18 | 9 |
| SR1 | 826 | 1 | 184 | 16 | 40 |
| SR1 | 834 | 1 | 145 | 9 | 32 |
| Xanthi | 851 | 1 | 140 | 15 | 5 |
| Samsun | 837 | 1 | 129 | 16 | 8 |
| Xanthi | 831 | 1 | 114 | 21 | 10 |
| Xanthi | 833 | 1 | 107 | 12 | 5 |
| Xanthi | 807 | 1 to 2 | 87 | 12 | 9 |
| | Controls | | 40 | 8 | 20 |

However, of 235 T1 plants analyzed, the single individual having the highest activity and the single observation of completely null expression were siblings of the T1 family 826. Moreover, extracts from 826 were also quantitatively the second highest sample of the original 46 analyzed for enzyme activity in the T0 generation. By Western blot, we

TABLE 4

LOCALIZATION OF rGCB TO THE INTERCELLULAR FLUID

| Sample | Fresh Weight (gr) | Total Volume (ml) | Protein Conc. (mg/ml) | Total Protein (mg) | Protein Yield (mg/gr) | rGCB Conc. (U/ml) | Total rGCE (U) | rGCB Yield (U/gr) | Specific Activity (U/mg) | % Recovery rGCB in IF | X-Fold Purification |
|---|---|---|---|---|---|---|---|---|---|---|---|
| Intercellular Fluid | 2.48 | 1.9 | 0.24 | 0.45 | 0.18 | 720 | 1368 | 552 | 3007 | 22 | 18 |
| Homogenate | 2.08 | 8.1 | 3.89 | 31.48 | 15.13 | 653 | 5289 | 2543 | 168 | | |

Specific activity is based on the hydrolysis of 4-MUG inhibited by 0.5 mM CBE.
Units (U) = nmol/hr.

Because the amount (in nanograms) of cross reacting material observed in a quantitative Western blot corresponds within experimental error to the amount (in nanograms) of enzyme calculated on the basis of activity, we believe the plant rGCB was synthesized with high specific activity. This was a very important and favorable indirect estimate of specific activity. The enzyme was purified to homogeneity to measure more precisely the actual specific activity.

analyzed protein extracts from several T1 siblings of this family, including the highest (612 U/mg) and the lowest (0 U/mg) and found a clear linear correlation between the amount of cross-reacting protein at 59 kDa and the activity loaded in each lane. In addition to the 59 kDa band, there were also variable amounts of cross-reacting protein at 52 kDa. In the null individual there was only the 52 kDa protein. We never observed this molecular weight species in the T0 extracts or in any other T1 family. There was no evidence of proteolytic activity in this sample as judged by mixing the null sample with high activity extracts and analyzing by enzyme assays and Western blots after incubation at 37° C. If the apparently truncated rGCB was derived from proteolytic cleavage, the protease activity must be both physiologically induced and inactive under these isolation conditions. When the null individual was self-pollinated and the T2 generation analyzed, enzyme expression reappeared as in the T1 and T0. Our working hypothesis was that the tobacco plant is able to limit the expression of the foreign enzyme as constitutively expressed from this cDNA construct, and that the threshold for the stochastic induction of this response during development occurs at an expression level corresponding to approximately 600 U/mg specific activity in the crude homogenate. Of the lines we created, 826 were able to produce enough mRNA to exceed this threshold in the homozygous state.

The silencing of genes in plants is a recently described phenomenon. Work has been done detailing a cellular surveillance mechanism that has apparently evolved to specifically degrade excess RNA (36). In one case, specific RNA cleavages near the 3'-end of the transcript initiate the removal of the transcript. Our description of the silencing of rGCB above 600 U/mg is the first association of silencing with a truncated protein, and may well be caused by a specific mRNA (and not protein) cleavage event. Gene silencing may determine an upper limit of expression attainable using constitutive transgene expression.

We subcloned the cDNA for glucocerebrosidase into a TMV-transient vector and cDNA combinations. Transcripts were synthesized in vitro and inoculated directly onto lower leaves of whole plants. In each case, there was an additional lag time of about 2 weeks post-inoculation before appearance of virus in the upper leaves of the plant and in each case the viral population no longer carried a significant portion of the gene. We detected no significant enzyme activity in either inoculated or systemically infected leaves. Very recently, we detected the gene in root tissue and in transfected protoplasts. There appears to be an incompatibility with leaf expression under conditions of viral amplification of the rGCB mRNA. This incompatibility selects for loss of the sequence from the viral population.

To further investigate the nature of the leaf incompatibility with rGCB expression, we built the construct pBSG641. This plasmid contains the rGCB gene substituted into the coat protein region. The remaining portion of the entire genome was then placed under control of the 35S promoter. The promoter was designed to initiate RNA synthesis such that the correct 5'-end of TMV would be synthesized. A custom-designed, self-cleaving ribozyme sequence positioned at the end of the genome yields a native 3'-end upon cleavage. The vector was designed for synthesis of infectious transcripts in vivo from a chromosomally integrated locus and production of rGCB through viral amplification of subgenomic mRNA in the cytoplasm. The vector alone without the gene for rGCB produces a systemic but capsid-free, "naked-RNA" infection (38). This RNA co-suppression is the subject of issued U.S. Pat. No. 5,922,602 issued Jul. 13, 1999, the disclosure of which is incorporated herein by reference.

We introduced the construct depicted in FIG. 15 into *Agrobacterium* and transformed tobacco plants as described above. In this case many of the plant leaves displayed necrotic lesions as transfection events randomly occurred during growth and development and expansion of leaves. These lesions never formed on control transformed plant lines containing vector only sequences capable of replication. These lesions were identical in appearance to the types of lesions induced by plant pathogens during a type of disease resistance reaction, termed the hypersensitive response (HR). Therefore, under conditions where we expect to accumulate large quantities of active enzyme, a HR is signaled by some component of the vector infection specific to rGCB. There are very few of these so-called HR "elicitors" characterized in the literature. Possibly the rGCB enzyme itself, or a secondary metabolite resulting from enzymatic activity, or even rGCB RNA, may induce the HR. In any case, we hypothesize that the HR selects for loss of the gene from the viral RNA population. It is important to remember that this is not a simple genetic instability phenomenon. Under conditions where a HR is not induced, we have synthesized many proteins using TMV-based RNA viral vectors to levels of several percent of the total soluble cell protein without loss of the inserted gene even after virion passage.

Expression of rGCB in Transgenic Tobacco is Robust. In several experiments, we inoculated wild type TMV onto rGCB containing transgenic tobacco and found a ~1.5–2 fold increase in the specific activity of total homogenates. It appears that the viral infection causes an increase in promoter activity, and/or the secretion and accumulation of active enzyme. This was an important result, because it demonstrates that the expression was compatible with a TMV infection, a physiologically severe stress condition. Furthermore, in separate work, we have used chimeric TMV particles as recombinant carriers for the production of small peptides (31).

Conclusions.

We used a wide range of gene expression tools to investigate the accumulation of rGCB in mature tobacco plants. Our results suggest attractive yield, quality and cost objectives can be met with further development. We observed two independent phenomena currently limiting the accumulation of enzyme activity in whole plants; gene silencing in one transgenic line, and a plant leaf hypersensitive response to transient vector mediated synthesis.

These current limitations in gene expression only serve to underscore the advantages and utility of agriculture for recombinant protein production. We have generated several transgenic tobacco lines as a reliable source of biomass for the production of high specific activity enzyme. Because the biomass is accumulated under no sterile growth conditions and production is inexpensively scaled to the quantities desired, it becomes feasible to exploit a dilute but enriched source such as the intercellular fluid fraction for industrial process development. This contrast is most clearly summarized in Table 6.

TABLE 6

INITIAL STEPS IN THE PURIFICATION OF GLUCOCEREBROSIDASE

| Purification Procedure | PLACENTA HOMOGENATE | | | TOBACCO HOMOGENATE | | | TOBACCO LEAF IF | | |
|---|---|---|---|---|---|---|---|---|---|
| | Activity Units/kg | Specific Activity Units/mg | Recovery % | Activity Units/kg | Specific Activity Units/mg | Recovery % | Activity Units/kg | Specific Activity Units/mg | Recovery % |
| Detergent Extraction | 1,510,000 | 375 | 100 | 1,870,000 | 230 | 100 | 877,000 | 9,967 | 100 |
| Concentration/ Delipidation | 707,000 | 9,330 | 47 | 1,540,000 | 14,400 | 82 | ↓ | ↓ | ↓ |
| Hydrophobic Chromatography | 554,000 | 147,000 | 36 | 1,242,000 | 82,000 | 74 | 535,000 | 34,547 | 61 |

The placental homogenate procedure is adapted from Furbish et al., (10) starting with a 14,000×g sedimented material. In a typical preparation 15–30 kg of fresh placentas were processed. The tobacco homogenate is based on the average of 2 typical 1 kg extractions of the leaf biomass. The IF data is from an average of 5 small scale extraction experiments (2–200 grams fresh weight), and a single chromatography run of an IF concentrate. For comparative purposes all yields are normalized to 1 kg.

TABLE 7

GCB IF PILOT PROCESS

| Purification Step | Greenhouse Scale (1 kg) | | | | Field Scale (100 kg) | | | |
|---|---|---|---|---|---|---|---|---|
| | Specific Activity Units/kg | Total Activity Units/mg | Recovery % | Purification Fold | Specific Activity Units/kg | Total Activity Units/mg | Recovery % | Purification Fold |
| IF | 4,153,533 | 20,388 | 100 | 1.0 | 434,927 | 2,745 | 100 | 1.0 |
| Phenyl SL | 3,738,180 | 147,813 | 91.4 | 7.25 | 194,722 | 12,960 | 44.4 | 5.0 |
| SP Big Beads | 2,740,086 | 650,377 | 67.0 | 31.9 | 145,060 | 99,220 | 33.1 | 38.2 |

For comparative purposes all yields are normalized to 1 kg.

The greenhouse/laboratory scale process is based on an average of 2 infiltration/chromatography runs starting with 1 kilogram of fresh weight leaf tissue.

The GenBank accession No. for glucocerebrosidase is M11080. The field scale process is an average of 7 large scale infiltrations consisting of 100 kilograms of fresh weight tissue. Enzyme activity is based on the cleavage of 4-methylumbelliferylglucoside (1 Unit=1 nmol/hr). One factor contributing to a lower apparent yield in the field on a fresh weight basis is that rGCB is concentrated in the leaf lamina and in the lab scale procedure the midrib was removed.

Preparation of Solutions for GCB Assay with 4-Methylumbelliferyl β-D-glucopyranoside 1. GCB Assay Buffer 0.1 M Potassium Phosphate, 0.15% Triton X-100, 0.125% sodium taurocholate (Sigma T-4009), 0.1% bovine serum albumin, 0.02% sodium azide, pH 5.9

Dissolve 13.6 grams of potassium phosphate monobasic ($KH_2PO_4$) in 950 ml of distilled water. Add 1.25 g of sodium taurocholate and 1.5 g of Triton X-100. Triton X-100 is a very viscous liquid and should be weighed rather than pipetted in order to achieve a reproducible buffer. Add 2 ml of 10% sodium azide and 1 gram of bovine serum albumin (BSA). Stir until all material has dissolved. Adjust the pH to 5.9 by the addition of a small amount of 1 N NaOH, then bring up to 1000 ml with water. Filter sterilize and store at 4° C. This buffer is stable for many months.

2. Stopping Buffer 0.1 M Glycine in 0.1 M NaOH. Dissolve 4 grams of NaOH and 7.51 grams of glycine in 1 liter of distilled water. Filter sterilize and store at 4° C. (Stable for years at 4° C).

3. Substrate (Sigma M-3633) FW 338.3

15 mM 4-methylumbelliferyl β-D-glucopyranoside (4-MUG) in assay buffer. Weigh out 1 gram of 4-MUG into a 500 ml Erlenmeyer flask. Add exactly 197 ml of Assay Buffer (Substrate dilution Buffer) and heat in a hot water bath to dissolve. Caution: Heating too aggressively results in unacceptably high background fluorescence. After cooling, dispense into 5–7 ml aliquots in 15 ml polypropylene tubes, let tubes cool to room temperature and freeze at −20° C. for later use.

4. 125 mM Conduritol-epoxide (CBE) (Toronto Research C-66600)

MW=162.18

Dissolve 100 mg of CBE in 4.92 ml of 0.1 M $KPO_4$ Buffer, pH 6.0. Dispense into 200–500 μl aliquots and store at −20° C.

5. 0.1 M $KPO_4$ Buffer, pH 6.0

| | |
|---|---|
| 1.75 ml of 0.5 M $KH_2PO_4$ (Solution A) | 87.5 mM |
| 0.246 ml of 0.5 M $K_2HPO_4$ (Solution B) | 12.3 mM |

Add distilled water to 10 ml.
Reagents:

| | |
|---|---|
| Potassium Phosphate Monobasic ($KH_2PO_4$) | Fisher Scientific P285 |
| Potassium Phosphate Dibasic ($K_2HPO_4$) | Fisher Scientific P288 |

-continued

| | |
|---|---|
| Triton X-100 | Sigma X-100 |
| Sodium Taurocholic Acid | Sigma T-4009 |
| Bovine Serum Albumin, Fraction V | Sigma A-2153 |
| Sodium Azide | Sigma S-2002 |
| Glycine | Sigma G-4392 |
| Sodium Hydroxide Pellets | Fisher Scientific S318 |
| Conduritol β-epoxide (CBE) | Toronto Research C-66600 MW = 162.18 |
| 4-Methylumbelliferyl β-D-glucopyranoside (β-D-glucoside) | Sigma M-3633 |

GCB Assay with 4-Methylumbelliferyl β-D-glucopyranoside (MUG)

1.0 Purpose

To measure the amount of glucocerebrosidase activity from transgenic tobacco plants following infiltration and/or homogenization of the tissue. Measurement of fluorometric activity requires an accurate determination and relationship between fluorescence of the released methylumbelliferone and its concentration under the assay conditions.

Scope

This is an inhibition assay. CBE inhibits human GCB. The fluorescent value used to calculate activity is based on the difference in values with and without inhibitor present. The fluorescent value with CBE (plant glucosidase) is subtracted from the fluorescent value without inhibitor which is both plant and human GCB activity. The difference being the value for human GCB expressed in the transgenic plants. The assay is carried out using 5 µl of sample with 45 µl assay buffer +/−CBE at 37° C. This means that 2 tubes are needed per sample. This procedure is applicable to the Glucocerebrosidase assay procedure requiring a methylumbelliferone standard curve.

Equipment

Fluorometer (St. John Associates Fluoro-Tec 2001A with KV-418 filter and 365 nm interference filter)
10×75 mm cuvettes (St. John Associates)
Water Bath
Test Tubes 13×100 mm glass (VWR or equivalent)
4-Methylumbelliferone (Sigma M-1381)
Pipettes and pipette tips, 5 µl–1 ml (Rainin or equivalent)
1.5 ml microfuge tubes Precautions The fluorometer should be warmed up for at least 20 minutes prior to reading samples. The power switch should be left on at all times. If the power switch was turned off it may take longer (up to 1 hour) for the instrument to stabilize.

Be certain to put away all reagents under proper storage conditions after reading assays. Any left over fluorescent substrates and CBE stock should be returned to −20° C. The fluorescent substrate and CBE stock can be frozen and thawed numerous times without any breakdown of the reagents. Do not save any substrate or assay buffer to which you added CBE. These should be discarded. You should only make up enough reagent with the inhibitor (CBE) that you currently need.

Procedure

1. Turn on the water bath and check to be certain the temperature is set to 37° C.

2. Turn on fluorometer to warm up by flipping up the PMT switch. It should be turned on at least 15–20 minutes before taking readings. If the power switch was turned off it may take longer (up to 1 hour) for the instrument to stabilize.

3. Remove assay buffer from refrigerator and CBE from −20° C. freezer. Thaw CBE on ice.

4. Defrost the appropriate amount of methylumbelliferyl β-D-glucopyranoside (MUG) substrate. You need 400 µl of MUG for each sample (+/−CBE). Place tubes in 37° C. $H_2O$ bath for approximately 10 minutes to get MUG into solution. Note: There may be a small amount of insoluble material (MUG) in each tube even after the 10 minutes at 37° C. Vortex before use. Keep at room temperature until ready to use.

5. Remove enough GCB Assay Buffer from the stock bottle that will be needed for your samples and transfer to a 15 ml tube. Add appropriate amount of 125 mM stock solution of CBE to assay buffer so the final concentration is 0.55 mM CBE. CBE stock is stored at −20° C. Thaw some CBE on ice now if you have not already done so. The assay buffer+CBE may be kept at room temperature if assays will be completed within 1 hour otherwise store solutions with CBE on ice. Note: you want the final conc. of CBE in the assay to be 0.5 mM, you are adding 45 µl of buffer to 5 µl of sample so the starting conc. of CBE should be 0.55 mM. Example: Add 8.8 µl of 125 mM CBE stock solution to 1.991 ml of assay buffer to equal 0.55 mM CBE in assay buffer. This is enough buffer to carry out at least 40 assays.

6. Label two 13×100 mM glass tubes for each sample to be assayed with a number and the same number and a "+" sign. (1, 1+, 2, 2+, etc). Tubes with "+" contain CBE, tubes with just a number will not have CBE added to the assay buffer or MUG.

Carry out the following steps on ice.

7. Place numbered tubes in white racks and place in Styrofoam ice chest filled with enough ice and $H_2O$ (Ice Bath) to cover the volume of fluid in these tubes.

8. Add 45 µl assay buffer to all the tubes with numbers only. Add 45 µl of assay buffer+CBE to all the "+" tubes. Place pipette tip in bottom of tube to deliver assay buffer to bottom of tube.

9. Remove metal tip ejector from P-10 pipetman (so pipetman will reach bottom of tube) and pipette 5 µl of sample into each set of appropriate tubes of assay buffer (one "+" and one tube with a number only (−CBE) for each sample or twice this number if done in duplicate). Place pipette tip in bottom of tube to deliver sample directly into assay buffer. This is very important since you will be pipetting small volumes into these tubes. Be sure to include a Buffer sample to blank the fluorometer. This will contain 5 µl of the same buffer that the samples are in. Note: See Dilution of Enzymes if your sample is too concentrated to read in the fluorometer. Basically, dilute your sample 1:5, 1:10, etc. in assay buffer, mix well, pulse in microfuge and add 5 µl of diluted sample to assay buffer above. You should only need 5–10 µl of your sample for the dilutions.

10. Incubate tubes at 37° C. for 10 minutes then place tubes immediately on ice.

11. Aliquot the volume of MUG needed for "+" tube assays (200 µl per assay+CBE) into a 15 ml polypropylene tube and add CBE stock to a final concentration of 0.5 mM.
    4 µl of 125 mM CBE per 1 ml MUG in assay buffer=0.5 mM CBE 12. Add MUG +/−CBE to appropriate tubes. Add 200 µl of MUG without CBE to all the tubes with a number only (−CBE). Add 200 µl of MUG+CBE to all the "+" tubes. Place a plastic cap over each tube. Vortex sample and place back on ice.

13. Transfer all tubes to 37° C. $H_2O$ bath. Incubate at 37° C. for 15 minutes with shaking. Set the shaker between the #4–6 settings.

14. Transfer tubes to ice bath. Quickly add 1 ml of stopping solution to each sample. Remove rack of samples from ice.

15. You are now ready to read samples in fluorometer.

16. Be certain to put away all reagents under proper storage conditions after reading assays. Any left over fluorescent substrates should be returned to −20° C. The fluorescent substrate and CBE stock can be frozen and thawed numerous times without any breakdown of the reagents. Do not save any substrate or assay buffer to which you added CBE. These should be discarded. You should only make up enough reagent with the inhibitor (CBE) that you currently need.

Dilution of Samples for Assays

Routine dilutions of samples should be carried out on ice using the GCB Assay Buffer described above to maintain enzyme activity. Generally a 1:5 or 1:10 dilution of the sample is sufficient. Dilutions should be carried out in a microfuge tube. (Example: 1:10 dilution: 5 μl of sample in 45 μl of assay buffer, mix well and pulse sample in microfuge to bring all of the sample to the bottom of the tube). You should only need 5–10 μl of your sample for the dilutions.

EXAMPLE 2

Extraction of Glucocerebrosidase Protein

Glucocerebrosidase (GCB), either derived from human placental tissue or a recombinant form from Chinese hamster ovary cells (CHO), is presently used in an effective but costly treatment of the heritable metabolic storage disorder known as Gaucher disease. We combined a dual promoter from Cauliflower Mosaic Virus (35S), a translational enhancer from Tobacco Etch Virus and a polyadenylation region from the nopaline synthetase gene of *Agrobacterium tumefaciens* with the native human GCB cDNA to create plasmid pBSG638. These expression elements are widely used to provide the highest possible constitutive expression of nuclear encoded genes in plants. The CaMV promoter is further inducible by stress or wound treatment.

Using a standard *Agrobacterium*-mediated transformation method, we regenerated 93 independent kanamycin-resistant transformants from leaf discs of four different tobacco cultivars (the TO generation). In Western blots of total protein extracts, cross-reacting antigen was detected in 46 of these TO individuals with antibody raised against human glucocerebrosidase. Specificity of the plant-expressed recombinant enzyme was confirmed by hydrolysis of 14C-radiolabeled glucosylceramide. According to these expression results the rGCB positive transformants were ranked into moderate (A), low (B) and negligible (C) activity groups.

We also found reaction conditions to preferentially inhibit rGCB enzyme activity in the presence of plant glucosidases using the suicide substrate conduritol B-epoxide (CBE). Total glucosidase activity, and rGCB activity were measured by hydrolysis of the fluorescent substrate 4-methylumbelliferylglucopyranoside (4-MUG) with and without CBE. Leaves from plants transfected with the vector TT01A 103L were removed at the petiole and slit down the midrib into two equal halves. To obtain a total cellular homogenate, one group of half-leaves was ground in the presence of 4 volumes of detergent extraction buffer (100 mM potassium phosphate p(I 6, 5 mM EDTA, 10 mM, B-mercaptoethanol and 0.5% w/v sodium taurocholate) with a mortar and pestle after freezing the tissue in liquid nitrogen. To recover the intercellular fluid (IF), the same enzyme extraction buffer was infiltrated into the opposing group of half-leaves by submerging the tissue and applying moderate vacuum pressure (500 mm Hg). After draining off excess buffer, the undisrupted half-leaves were rolled gently in Parafilm, placed in disposable tubes and the intercellular fluid (IF) was collected by low-speed centrifugation (1,000 g). The weight of buffer recovered from the infiltrated leaf tissue is recorded and varies from approximately one-half to equal the original weight of the leaf. GCB expression in IF extracts was quantified using a commercially available enzyme assay reagents and protocol. Total protein was determined by the method described by Bradford (Bradford, M. Anal. Biochem 72:248, 1976).

We have demonstrated that active recombinant GCB may be successfully extracted from the intercellular fluid of plant leaves using the present method. The GCB assay is based on MUG hydrolysis in the presence of CBE. The IF method results in a recovery of 22% of the total GCB activity of the leaf at a 18-fold enrichment relative to an extract obtained by homogenization (H). The GCB production results may be improved by optimizing the time post-inoculation with the viral vector and minimizing the contaminating viral coat protein from the intercellular fraction.

EXAMPLE 3

Laboratory Pilot Scale Purification of Glucocerebrosidase from the Intercellular Fluid of Tobacco MD609 leaf tissue (1–2 kilograms) of transgenic tobacco expressing the lysosomal enzyme glucocerebrosidase was harvested, the mid vein removed and the tissue weighed. Tissue was submerged with 2–4 volumes of buffer (0.1 M $KPO_4$ buffer, pH 6.0, 5 mM EDTA, 0.5% taurocholic acid, 10 mM β-mercaptoethanol) in an infiltration vessel that accommodates several kilograms of leaf tissue at one time. A perforated metal plate was placed on top of tissue to weigh down the tissue. A vacuum of 25–27 in. Hg was applied for 1–2 minutes×3. The vacuum was released between subsequent applications. Tissue was rotated and the vacuum reapplied to achieve complete infiltration. Multiple applications of the vacuum without isolating the intercellular fluid constitutes a single infiltration procedure. An indication of complete infiltration is a distinct darkening in color of the underside of the leaf tissue. Excess buffer on the tissue was drained. The intercellular fluid was released from the tissue by centrifuging the tissue in a basket rotor at 4200 RPM (2500×g) for 10 minutes. The intercellular fluid was collected using an aspirator hooked up to a vacuum pump (IF-1). Alternatively, the leaf tissue can be re-infiltrated by placing the leaves back in the infiltration vessel in the same buffer used above and the process repeated (IF-2). The second infiltration does not require as many applications of the vacuum. Additionally, the buffer may be drained from the infiltration vessel (spent buffer) and pooled with the 1st and 2nd IF fractions. Collectively, IF-1, IF-2 and Spent Buffer constitutes the IF pool. The volume of intercellular fluid collected from the infiltrated leaf tissue was between 50–100% of the leaf tissue by weight depending on the number of infiltrations carried out.

Recombinant GCB was purified by loading the dilute intercellular (feed stream) directly on a Pharmacia Streamline 25 column containing Phenyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM citrate, 20% ethylene glycol, pH 5.0 and then eluted with 25 mM citrate, 70% ethylene glycol. The eluted material was further purified on a cation exchange resin, SP Big Beads (Pharmacia), equilibrated in 25 mM citrate, 75 mM NaCl, pH 5.0. GCB was eluted with either a step gradient of 25 mM citrate, 0.5 M NaCl, 10% ethylene glycol, pH 5.0 or a linear gradient of 75 mM–0,4 M NaCl in 25 mM citrate, pH 5.0. All chromatography steps were carried out at room temperature.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay based on the method of Bradford (1976).

Typically from 1 kilogram of leaves where IF-1 alone was collected we obtained 4 million unites of GCB at a specific activity of 20,000. The Units/kg increased to 6 million with a lower specific activity of 10,000 when IF Pool was collected (IF-1, IF-2 and spent buffer). For more information on these experiments, see International Patent Application No. PCT/US99/18161 and U.S. Pat. No. 6,284,875. The disclosures of which are incorporated herein by reference.

EXAMPLE 4

Ultrafiltration/Concentration of Intercellular Fluid from Tobacco Expressing Glucocerebrosidase 2.3 kilograms of MD609 leaf tissue from transgenic tobacco expressing the lysosomal enzyme glucocerebrosidase was harvested, the mid vein removed and the tissue weighed. Tissue was submerged with 2–4 volumes of buffer (0.1 M $KPO_4$ buffer, pH 6.0, 5 mM EDTA, 0.5% taurocholic acid, 10 mM β-mercaptoethanol) in an infiltration vessel that accommodates several kilograms of leaf tissue at one time. A perforated metal plate was placed on top of tissue to weigh down the tissue. A vacuum of 25–27 in. Hg was applied for 1–2 minutes×3. The vacuum was released between subsequent applications. Tissue was rotated and the vacuum reapplied to achieve complete infiltration. Excess buffer on the tissue was drained. The intercellular fluid was released from the tissue by centrifuging the tissue in a basket rotor at 4200 RPM (2500×g) for 10 minutes. The intercellular fluid was collected using an aspirator hooked up to a vacuum pump (IF-1). The leaf tissue was re-infiltrated by placing the leaves back in the infiltration vessel in the same buffer used above and the process repeated (IF-2). The buffer was drained from the infiltration vessel (spent buffer) and pooled with the 1st and 2nd IF fractions. Collectively, IF-1, IF-2 and Spent Buffer constitutes the IF pool. The IF pool was filtered through Miracloth and then concentrated 6 fold by passing the IF pool through a 1 sq. ft. spiral membrane (30K molecular weight cutoff) using an Amicon RA 2000 concentrator equipped with an LP-1 pump.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay based on the method of Bradford (1976).

EXAMPLE 5

Pilot Scale Purification of Glucocerebrosidase from the Intercellular Fluid of Field Grown Tobacco 100 kilograms of MD609 leaf tissue from transgenic tobacco expressing the lysosomal enzyme glucocerebrosidase was harvested from the field each day for a period of two weeks. The tissue was stripped off the stalks by hand and weighed. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Multiple applications of the vacuum without isolating the intercellular fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue. Alternatively, the leaf tissue can be re-infiltrated by placing the leaves back in the infiltration vessel in the same buffer used above and the process repeated (IF-2). Additionally, the buffer may be drained from the infiltration vessel (spent buffer) and may be pooled with the 1st and 2nd IF fractions. Collectively, IF-1, IF-2 and Spent Buffer constitutes the IF pool. The volume of intercellular fluid collected from the infiltrated leaf tissue was between 42–170% of the leaf tissue by weight depending on the number of infiltrations carried out.

Recombinant GCB was purified by loading the dilute intercellular (feed stream) directly on a Pharmacia Streamline 200 column containing Phenyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM citrate, 20% ethylene glycol, pH 5.0 and then eluted with 25 mM citrate, 70% ethylene glycol. The eluted material was sterile filtered by passing the eluted material through a 1 sq. ft. 0.8 um Sartoclean GF capsule followed by a 1 sq. ft. 0.2 um Sartobran P sterile filter (Sartorius, Corp.) and stored at 4° C. until the next chromatography step. The eluted material from 4–5 days of Phenyl Streamline chromatography runs was pooled together and further purified on a cation exchange resin, SP Big Beads (Pharmacia), equilibrated in 25 mM citrate, 75 mM NaCl, pH 5.0. GCB was eluted with a step gradient of 25 mM citrate, 0.4 M NaCl, 10% ethylene glycol, pH 5.0. All chromatography steps were carried out at room temperature. The eluted material was sterile filtered by passing the eluted material through a 1 sq. ft. 0.8 um Sartoclean GF capsule followed by a 1 sq. ft. 0.2 um Sartobran P sterile filter (Sartorius, Corp.) and stored at 4° C.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. Total protein was determined using the Bio-Rad Protein Assay based on the method of Bradford (1976).

Typically from 1 kilogram of field grown tobacco, expressing GCB, where IF-1 alone was collected we obtained 435,000 units of GCB at a specific activity of 2,745. The Units/kg increased to 755,000 with a specific activity of 3,400 when IF Pool was collected (IF-1, IF-2 and spent buffer).

EXAMPLE 6

Total GCB (IF vs. Homogenate) in "GCB Field Test Virus"

100 kilograms of MD609 leaf tissue from transgenic tobacco expressing the lysosomal enzyme glucocerebrosidase was harvested from the field each day for a period of two weeks. The tissue was stripped off the stalks by hand and weighed. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue. In order to evaluate how much enzyme was recovered in the intercellular fluid, the tissue from which the intercellular fluid was isolated was then homogenized in a Waring blender with 4 volumes of the same infiltration buffer as above, centrifuged and the supernatant assayed for enzyme activity.

EXAMPLE 7

Chops Experiment

An experiment was carried out where 100 kilograms of MD609 leaf tissue of transgenic tobacco expressing the lysosomal enzyme glucocerebrosidase was harvested off the stalks by hand, weighed and chopped into small pieces to increase the surface area for buffer infiltration. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue. In order to evaluate how much enzyme was recovered in the intercellular fluid, the tissue from which the intercellular fluid was isolated was then homogenized in a Waring blender with 4 volumes of the same infiltration buffer as above, centrifuged and the supernatant assayed for enzyme activity.

Recombinant GCB was purified by loading the dilute intercellular (feed stream) directly on a Pharmacia Streamline 200 column containing Phenyl Streamline resin. The column was equilibrated and washed until UV-signal on recorder returned to baseline with 25 mM citrate, 20% ethylene glycol, pH 5.0 and then eluted with 25 mM citrate, 70% ethylene glycol. All chromatography steps were carried out at room temperature Table 10 below contains data from the chops experiment.

EXAMPLE 8

Pilot Scale of Purification of Alpha Galactosidase from the Intercellular Fluid of *Nicotiana benthamiana*

Young actively growing *Nicotiana benthamiana* plants were inoculated with infectious transcripts of a recombinant plant viral construct containing the lysosomal enzyme α galactosidase gene. Systemically infected leaf tissue (1–2 kilograms) was harvested from *Nicotiana benthamiana* expressing α galactosidase 14 days post inoculation. The tissue was weighed and submerged with 2–4 volumes of buffer (25 mM Bis Tris Propane Buffer, pH 6.0, 5 mM EDTA, 0.1 M NaCl, 10 mM β-mercaptoethanol) in an infiltration vessel that can accommodate several kilograms of leaf tissue at one time. A perforated metal plate was placed on top of tissue to weigh down the tissue. A vacuum of 25–27 in. Hg was applied for 30 seconds and then quickly released. The tissue was rotated and the vacuum reapplied to achieve complete infiltration which was confirmed by a distinct darkening in color of the underside of the leaf tissue. Excess buffer on the tissue was drained. The intercellular fluid was released from the tissue by centrifuging the tissue in a basket rotor at 3800 RPM (2100×g) for 10–15 minutes. The intercellular fluid was collected using an aspirator hooked up to a vacuum pump. In some instances only infected leaf tissue was harvested. Alternatively, petioles and stems have been harvested along with the leaf tissue for infiltration. The mid vein was not removed from the tissue prior to infiltration.

Alpha galactosidase was purified by loading the dilute intercellular (fed stream) directly onto a Pharmacia Streamline 25 column containing Butyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM Bis Tris Propane, pH 6.0 20% (NH$_4$)$_2$S04 and then eluted with 25 mM Bis Tris Propane, pH 6.0. The eluted material was further purified on Hydroxyapatite equilibrated with 1 mM NaPO$_4$ Buffer, 5% glycerol, pH 6.0 and eluted with either a 1–250 mM NaPO$_4$ buffer, 5% glycerol, pH 6.0 linear gradient or a step gradient. All chromatography steps were carried out at room temperature.

Alpha galactosidase activity was measured by hydrolysis of the fluorescent substrate 4-methylumbelliferyl a-D galactopyranoside. Enzyme activity was measured at 37° C. in a reaction mixture containing 5 mM methylumbelliferyl a-D galactopyranoside, 0.1 M Potassium Phosphate, 0.15% Triton-X100, 0.125% sodium taurocholate, 0.1% bovine serum albumin, pH 5.9. Total protein was determined using the Bio-Rad Protein Assay based on the method of Bradford (Bradford, M. Anal. Biochem. 72: 248; 1976).

From 1 kilogram of leaves, we typically obtain between 140–160 million units of α galactosidase at a specific activity of 800,000 following a single infiltration procedure (IF-1).

EXAMPLE 9

Pilot Scale Purification of Glucocerebrosidase from the Intercellular Fluid of Field Grown Tobacco Transgenic tobacco (MD609) expressing the lysosomal enzyme glucocerebrosidase was mechanically inoculated with a tobacco mosaic virus derivative containing a coat protein loop fusion, TMV291, (Turpen, et.al., 1995, Bio/Technology 13: 23–57). A total of 100 Kg of transgenic, transfected leaf tissue was harvested from the field, five weeks post inoculation. The tissue was stripped off the stalks by hand and weighed. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 KPO$_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Multiple applications of the vacuum without isolating the intercellular fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue.

Recombinant GCB was purified by loading the dilute intercellular (feed stream) directly on a Pharmacia Streamline 200 column containing Phenyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM citrate, 20% ethylene glycol, pH 5.0 and then eluted with 25 mM citrate, 70% ethylene glycol. The eluted material was sterile filtered by passing the eluted material through a 1 sq. ft. 0.8 um Sartoclean GF capsule followed by a 1 sq. ft. 0.2 um Sartobran P sterile filter (Sartorius, Corp.) and stored at 4° C. until the next chromatography step. The eluted material from 4–5 days of Phenyl Streamline chromatography runs was pooled together and further purified on a cation exchange resin, SP Big Beads (Pharmacia), equilibrated in 25 mM citrate, 75 mM NaCl, pH 5.0. GCB was eluted with a step gradient of 25 mM citrate, 0.4 M NaCl, 10% ethylene glycol, pH 5.0. All chromatography steps were carried out at room temperature. The eluted material was sterile filtered by passing the eluted material through a 1 sq. ft. 0.8 um Sartoclean GF capsule followed by a 1 sq. ft. 0.2 um Sartobran P sterile filter (Sartorius, Corp.) and stored at 4° C.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. Total protein was determined using the Bio-Rad Protein Assay based on the method of Bradford (1976). Table 7 contains the GCB recovery data from TMV transfected plant tissue.

The quantity of virus present in IF extracted leaf tissue was determined using homogenization and polyethylene glycol precipitation methods. In addition, the amount of virus present in the pooled, intercellular fluid was determined by direct polyethylene glycol precipitation. Final virus yields from precipitated samples was determined spectrophotometrically by absorbance at 260 nm.

TABLE 8

| Sample | Virus Titer |
| --- | --- |
| IF extracted leaf tissue | 0.206 mg virus/g fresh weight |
| Pooled IF | 0.004 mg virus/g fresh weight, 0.010 mg virus/ml IF |

EXAMPLE 10

Making rGAL-A Enzyme

Experimental Results. Achieving high steady-state mRNA levels is a prerequisite for vector development. However, there are many complex biochemical and host compatibility interactions that ultimately determine the overall performance of a heterologous expression system for a given protein. For this reason, we initiated some preliminary experiments to test the potential for RNA-viral mediated synthesis of active rGal-A in whole plants.

In order to ensure efficient delivery of rGal-A into the lumen of the plant endoplasmic reticulum, we fused the Gal-A cDNA (31) to a plant signal peptide sequence derived from rice α-amylase gene (32,33). We also hypothesized that addition of an ER-retention signal (SEKDEL) (SEQ ID NO:37) might prolong the resident time of the recombinant protein in the ER to increase the fraction of correctly assembled and catalytically active enzyme under extreme conditions of protein synthesis. These constructs were subcloned into the viral vector TTODA, a chimera between tobacco and tomato mosaic viruses (FIG. 1). Transcripts were prepared in vitro and inoculated onto the lower leaves of whole plants (*Nicotiana benthamiana*). 1–3 weeks after inoculation, leaves were weighed, rolled in a strip of Parafilm and placed in a disposable chromatography column and submerged in enzyme extraction buffer (0.1 M K/P04, 0.1 M NaCl, 5 mM EDTA, 10 mM β-ME and 0.5% sodium taurocholate, pH 6.0). In order to infiltrate the buffer into the tissue, a vacuum of 730–750 mmHg was twice applied. After draining the excess buffer, the intercellular fluid fraction was recovered by low-speed centrifugation (~1,500×g, 15 min). To measure enzyme remaining in the tissue after this treatment, the leaf was unrolled after centrifugation and two discs removed with a #14 cork borer. This tissue sample was transferred to an eppendorf tube, frozen in liquid nitrogen and ground in four volumes of enzyme extraction buffer. In rGal-A enzyme assays, we measured cleavage of the fluorogenic substrate 4-methyl umbeliferyl α-D-galactopyranoside (4-MUG) against known standards using established protocols (34). Units are nmoles of 4-MUG hydrolyzed per hour at 37° C.

In several initial experiments, plant leaves transfected with all constructs accumulated 1–2% of the total soluble plant protein as cross reacting immunologic material (CRIM) using antisera specific for Gal-A in quantitative Western analyses (data not shown). However, enzyme activity was much lower than expected for this amount of CRIM and furthermore was only 2–4 fold higher than activity due to endogenous plant α-galactosidase isozymes. It also appeared that addition of the ER retention signal allowed highest accumulation of steady state activity and that the IF contained little if any additional activity or CRIM. There are three cellular fates for any glycoprotein synthesized in a plant leaf: secretion to the IF, retention in the ER or sorting to the vacuole (35). We reasoned that because the ER retention signal slightly increased expression, the majority of the enzyme was inactivated later in the secretory pathway. This could most likely occur by aggregation in the trans-golgi network as is reported during over-production of this enzyme in CHO-cells (36), and/or in the plant leaf vacuole. The IF fraction is quite clear and non-pigmented and is suitable for direct chromatography. Using the initial construct (rGal-SEKDEL) (SEQ ID NO: 24) we partially purified small amounts of rGal-A from the IF on hydrophobic, lectin and size exclusion resins.

For several plant proteins vacuolar sorting information is located in a carboxy-terminal propeptide (CTPP; 37,38). During the original cloning and characterization of human Gal-A, Quinn et al., postulated a cathepsin-like potential CTPP cleavage for this enzyme at or near two arginine residues, 26 and 28 AA from the termination codon (39,40). The precise AA sequence at the carboxy terminus has, to our knowledge, never been reported. Because secretion in the plant leaf is through a default pathway we reasoned that deletion of specific sorting information from a postulated CTPP might yield more active enzyme in the IF. Analysis of a second set of constructs containing either 12 or 25 AA truncations, with and without the ER retention signal provided dramatic evidence for the significance of this region (See Table 9). In one construct, rGal 12-SEKDEL, virtually all of the CRIM is now assembled and stored as fully active enzyme and is secreted to the IF in significant quantities. As demonstrated in FIG. 3, rGal-A (~52 kDa) is now the most abundant plant protein in a crude leaf IF sample. The other predominant band at 17.5 kDa is the viral structural protein which likely contaminates this fraction from broken trichomes of the leaf surface.

TABLE 9

| rGal-A Expression (U/Gram Leaf Tissue) | | | |
|---|---|---|---|
| Contract/Sample | Intercellular Fluid | Residual Homogenate | Total |
| Experiment | | | |
| Uninfected Plant | 2,800 | 7,500 | 10,300 |
| rGal-A | 5,100 | 10,900 | 25,000 |
| rGal-A | 5,400 | 15,000 | 20,400 |
| rGal-A-SEKDEL | 6,800 | 30,300 | 37,100 |
| rGal-A-SEKDEL | 5,200 | 34,500 | 39,700 |
| Experiment | | | |
| Uninfected Plant | 2,300 | 4,800 | 7,100 |
| rGal-A 25 | 4,000 | 8,900 | 12,900 |
| rGal-A 25 | 2,300 | 9,000 | 11,300 |
| rGal-A 25-SEKDEL | 3,200 | 10,000 | 13,200 |
| rGal-A 25-SEKDEL | 2,800 | 8,600 | 11,400 |
| rGal-A 12 | 5,500 | 11,700 | 17,200 |
| rGal-A 12-SEKDEL | 109,800 | 117,700 | 227,500 |
| rGal-A 12-SEKDEL | 199,000 | 329,500 | 528,500 |

EXAMPLE 11

α-Galactosidase Expression Vector Development, Construction and Testing

The following example describes the series of α-galactosidase vectors that were constructed and tested for enzyme production. Initially, the human α-galactosidase A cDNA (Sugimoto, Y., Aksentijevich, I., Murray, G. J., Brady, R. O., Pastan, I., and Gottesman, M. M. Retroviral coexpression of a multidrug resistance gene (MDRI) and human α-galactosidase A for gene therapy of Fabry disease. Human Gene Therapy 6:905, 1995) was fused to a plant signal peptide sequence derived from a rice α-amylase gene (Kumagai, M. H., Shah, M., Terashima, M., Vrkljan, Z., Whitaker, J. R., and Rodriguez, R. L. Expression and secretion of rice α-amylase by *Saccharomyces cerevisiae*. Gene 94:209, 1990.). This chimeric gene was subcloned into the TMV based expression vector TTODA resulting in a construct designated rGAL-A, see Table 10. Vector rGAL-A was modified by the addition of the putative ER retention signal SEKDEL, resulting in the vector designated rGAL-AR, see Table 10.

A series of C-terminal amino acid deletions were introduced into the α-galactosidase gene. Deletions of 4, 8, 12 or 25 codons from the C-terminus of rGAL-A were generated as well as the addition of the putative ER retention sequence (SEKDEL), see Table 10 and FIG. 12 (sequence of TTODA (rGAL-12R). The deletion vectors were designated as described in Table 10:

TABLE 10

| Vector Designation | Carboxy-Terminal Modifications (Amino Acid Sequence) |
|---|---|
| rGAL-A | TSRLRSHINPTGTVLLQLENTMQMSLKDLL (SEQ ID NO:23) |
| rGAL-AR | TSRLRSHINPTGTVLLQLENTMQMSLKDLLSEKDEL (SEQ ID NO:24) |
| rGAL-4 | TSRLRSHINPTGTVLLQLENTMQMSL (SEQ ID NO:25) |

TABLE 10-continued

| Vector Designation | Carboxy-Terminal Modifications (Amino Acid Sequence) |
|---|---|
| rGAL-4R | TSRLRSHINPTGTVLLQLENTMQMSLSEKDEL (SEQ ID NO:26) |
| rGAL-8 | TSRLRSHINPTGTVLLQLENTM (SEQ ID NO:27) |
| rGAL-8R | TSRLRSHINPTGTVLLQLENTMSEKDEL (SEQ ID NO:28) |
| rGAL-12 | TSRLRSHINPTGTVLLQL (SEQ ID NO:29) |
| rGAL-12R | TSRLRSHINPTGTVLLQLSEKDEL (SEQ ID NO:30) |
| rGAL-25 | TSRLR (SEQ ID NO:31) |
| rGAL-25R | TSRLRSEKDEL (SEQ ID NO:32) |

The α-galactosidase gene fragment present in vector rGAL-12R was placed into TMV vector SBS5. In addition, the rice α-amylase signal peptide present in rGAL-12R was replaced by the native human α-galactosidase signal peptide. The resultant vector designated SBS5-rGAL-12R, see FIG. 13, exhibited genetic stability upon serial passage on N. benthamiana plants.

α-galactosidase was extracted from inoculated plants using interstitial fluid and homogenization methods. Fluids were analyzed for α-galactosidase yield, enzyme activity and cellular partitioning and targeting, see Table 11. In all cases, infectious transcripts were prepared in vitro and inoculated onto the lower leaves of actively growing Nicotiana benthamiana plants. Characteristic viral symptoms, vein clearing and leaf curling, were noted ~6–8 dpi (days post inoculation). Tissue samples were obtained from infected plants 1–3 weeks after inoculation. Leaves were weighed, rolled in a strip of Parafilm and placed in a disposable chromatography column and submerged in extraction buffer (0.1 M K/P04, 0.1 M NaCl, 5 mM EDTA, 10 mM β-ME and 0.5% sodium taurocholate, pH 6.0). Extraction buffer was infiltrated into the tissue by pumping a vacuum of 730–750 mmHg. The vacuum was applied and released two times. After draining the excess buffer, the interstitial fluid (IF) fraction was recovered by low-speed centrifugation (~1,500×g, 15 min). To measure enzyme remaining in the tissue after this treatment, the leaf was unrolled after centrifugation and two discs (~1 mg each) removed with a #14 cork borer. This tissue sample was transferred to an Eppendorf tube, frozen in liquid nitrogen and ground in four volumes of extraction buffer. The total homogenate was then subjected to centrifugation at ~5,000×g and the supernatant fraction was saved for further analysis.

Extracts from IF and homogenates from post-IF leaf tissue were analyzed for enzymatic activity by the hydrolysis of the fluorescent substrate 4-methyl umbeliferyl α-D-galactopyranoside (4-MUG). Known standards and established protocols (Suzuki, K. Enzymatic diagnosis of sphingolipidoses. Meth. Enzy. 138:727, 1987.) were used to obtain the number of enzymatic units (nmoles of 4-MUG hydrolyzed per hour at 37° C.) per gram fresh weight of tissue harvested.

TABLE 11

| Vector Designation | Interstitial Fluid Units/ gram leaf | Homogenate Units/ gram leaf | Total Enzyme Activity Units/ gram leaf | Ratio of Activity IF/ Homogenate |
|---|---|---|---|---|
| Uninfected | 3,837 | 9,404 | 13,241 | 0.41 |
| rGAL-A | 6,833 | 189,971 | 196,804 | 0.04 |
| rGAL-AR | 6,829 | 312,068 | 318,897 | 0.02 |
| rGAL-4 | 16,088 | 262,806 | 278,894 | 0.06 |
| rGAL-4R | 8,245 | 357,414 | 365,659 | 0.02 |
| rGAL-8 | 261,814 | 524,857 | 789,671 | 0.50 |
| rGAL-8R | 10,628 | 469,956 | 480,584 | 0.02 |
| rGAL-12 | 2,564 | 8,743 | 11,307 | 0.29 |
| rGAL-12R | 305,803 | 1,033,921 | 1,339,724 | 0.30 |
| rGAL-25 | 1,265 | 6,629 | 7,894 | 0.19 |
| rGAL-25R | 2,489 | 6,394 | 8,883 | 0.39 |

Enzyme activity data from IF and homogenates derived from plants expressing α-galactosidase from the vectors in Table 11. indicate that carboxy-terminal deletions (4–12 codons) results in increased α-galactosidase expression. Vector rGAL-12R expressed the highest level of total α-galactosidase and also secreted the highest quantity of active enzyme.

EXAMPLE 12

Pilot Scale Purification of α-Galactosidase

Actively growing Nicotiana benthamiana plants, propagated in an uncontrolled horticultural greenhouse, were inoculated with encapsidated transcripts derived from the expression vector, SBS5-rGAL-12R. Tissue was harvested 14–17 days post inoculation. Five kilograms of leaves were placed into polyester bags (Filtra-Spec®, 12-2-1053) and four×5 kg bags of leaves were placed into a metal basket. The metal basket containing the leaf material was placed in a 200 liter Mueller® vacuum tank containing ~100 liters of buffered solution (50 mM acetate, 5 mM EDTA, 10 mM 2-mercaptoethanol, pH 5.0). A 70 lb. stainless steel plate was placed over the leaves/bags to assure complete immersion. A vacuum was pumped to 695 mm Hg, held for 1 minute and then rapidly released. This vacuum infiltration was repeated for a total of two cycles. Multiple applications of the vacuum without isolating the interstitial fluid constitute a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The interstitial fluid (IF) was recovered from the vacuum infiltrated leaves by centrifugation (1,800×G, 30 minutes) using a Heine® basket centrifuge (bowl dimensions, 28.0 inches diameter×16.5 inches). The IF was filtered through a 50 μm cartridge filter to remove plant debris prior to purification.

Ammonium sulfate was added to the IF to 15% saturation, mixed for 10 minutes and loaded onto a Pharmacia Streamline 200 column containing 4 liters of Butyl Streamline resin equilibrated with 25 mM Imidizole, 15% $(NH_4)_2SO_4$, pH 6.0 at 1.2 L/min. The column was washed to UV baseline with 25 mM Imidizole, pH 6.0, 15% $(NH_4)_2SO_4$ and a Gal was eluted with a step gradient of 25 mM Imidizole, pH 6.0. The eluent was filtered through a Sartorius glass fiber—>0.8 um cartridge filter and loaded directly onto 3 liters of Blue Sepharose in a Pharmacia BPG 200 column equilibrated with 25 mM Imidizole, pH 6.0. The column was washed to UV baseline with 25 mM Imidizole, pH 6.0 and α gal was eluted with a step gradient of 25 mM Imidizole, 650 mM NaCl, pH 6.0. The eluent was concentrated using a 10 kD MWCO, cellulose acetate, 3 ft² spiral membrane in an Amicon CH-2 concentrator and then sterile filtered.

Further purification was carried out either on Octyl Sepharose FF or Hydroxyapatite. For Octyl Sepharose the column was equilibrated with 25 mM Imidizole, 25% ammonium sulfate, pH 6.0 and eluted using a linear gradient of 25–0% $(NH_4)_2SO_4$ in 25 mM Imidizole, pH 6.0. For Hydroxyapatite purification, the sample was dialyzed overnight against 10 mM $KPO_4$Buffer, pH 7.0 and then loaded on a column was equilibrated with 10 mM $KPO_4$Buffer, pH 7.0. The column was washed with equilibration buffer until the UV reached baseline, followed by a linear gradient of 10–200 mM $KPO_4$Buffer, pH 7.0. The α gal flowed through the column free of the contaminating proteins.

Alpha gal activity was measured throughout the process with a fluorescent assay using the synthetic substrate, 4-methylumbelliferyl-α-D-galactopyranoside (MU-α gal). Enzyme activity was measured at 37° C. in a reaction mixture containing 5 mM methylumbelliferyl α-D-galactopyranoside, 0.1 M Potassium Phosphate, 0.15% Triton-X100, 0.125% sodium taurocholate, and 0.1% bovine serum albumin, pH 5.9. One unit of enzymatic activity hydrolyzes 1 nmol of MU-α-gal per hour at 37° C. Total protein was determined using the Bio-Rad Protein Assay based on the method of Bradford (Bradford, M. Anal. Biochem. 72: 248; 1976). Results of α-galactosidase activity (Total units and specific activity) from different enzyme production lots are shown in Table 12.

TABLE 12

| Lot Number | Kg Biomass Extracted | Total Units (IF) | Specific Activity Units/mg protein (Purified) |
|---|---|---|---|
| 981215 | 44.4 | $2.9 \times 10^9$ | $5.0 \times 10^6$ |
| 991115 | 100 | $5.5 \times 10^9$ | $3.6 \times 10^6$ |
| 991116 | 120 | $6.9 \times 10^9$ | $4.0 \times 10^6$ |
| 991117 | 120 | $5.9 \times 10^9$ | $3.5 \times 10^{6*}$ |
| 991118 | 95.6 | $7.0 \times 10^9$ | $3.5 \times 10^{6*}$ |

*Butyl eluents from lots 991117 and 991118 were pooled before final chromatography and purification. The data presented in Table 12 demonstrates the consistency of pilot-scale extraction with respect to secreted enzyme yield and specific activity.

EXAMPLE 13
Analysis of Purified α-Galactosidase
N-terminal Sequence Analysis

N-terminal sequence analysis of α-galactosidase, purified from plants inoculated with transcripts derived from the vector rGAL-12R, MLDNGLARTPT (see SEQ ID NO: 1), had a 100% sequence homology to 11 amino acids of human placental α-galactosidase with the addition of an N-terminal methionine. In contrast, N-terminal sequence of α-galactosidase, purified from plants inoculated with transcripts derived from the vector SBS5-rGAL-12R, LDNGLARTPT (see SEQ ID NO:2), was as expected from native human enzyme. These data indicates the high degree of fidelity that post-translational modifications are carried out within plant leaf cells and that human signal peptides are processed with equal specificity in plants as in the native mammalian source.

C-Terminal Sequence Analysis

C-Terminal sequence of the rGAL-12R and SBS5-rGAL-12R plant produced enzyme was obtained by Edman degradation using the commercial service of the Mayo Foundation. Three cycles were achieved before the signal was too low to read additional sequence. Expected C-Terminus: LLQLSEKDEL (see SEQ ID NO:30).

| Cycle | Major amino acids |
|---|---|
| 1st | L, E |
| 2nd | D, V, A |
| 3rd | Q, G, T |

It is important to note that the C-terminal amino acid was found to be heterogeneous, either L or E. The presence of glutamic acid in the first cycle greatly reduced the signal because glutamic acid can form a cyclic structure during the activation step that disables cleavage from the chain and therefore blocks a portion of the sample to further sequencing. This reduced that ability of the software to interpret cycle 3 and beyond. However, the presence of L, E and D in the first two cycles and the absence of other amino acids present in the analysis in an order resembling the α-galactosidase sequence strongly suggests that a population of the enzyme terminates with a DEL sequence as expected from the sequence of the DNA clone.

Molecular Weight Determination

The apparent molecular weight of SBS5-rGAL-12R derived α-galactosidase (~50 kDa) was quite similar to human α-galactosidase A, purified from human placenta, as judged by both coomassie and silver stained SDS-PAGE. However, the protein purified from plant sources showed less molecular weight variation than the native human protein, indicating less heterogeneity in plant glycosylation or a higher purity plant enzyme preparation.

The molecular mass of several lots of plant derived α-galactosidase were determined by MALDI-TOF mass spectroscopy to be 48,963, 48,913, 49,100 daltons. These weights are consistent with the predicted mass of α-galactosidase, based upon amino acid sequence, allowing for broader peaks due to glycosylation. The calculated molecular weight of SBS5-rGAL-12R derived α-galactosidase is 44,619. The difference in predicted and observed mass would equate to approximately 10.0% carbohydrate.

Glycan Analysis

There are four potential N-glycosylation consensus sequences (N-X-T/S) reported for human α gal A (Matsuura, et. al. Glycobiology 8:329–339, 1998). We have identified four potential sites (108, 161, 184, 377) in our plant expressed α gal. One potential glycosylation site, in our α gal, is not glycosylated (377), as is the case for human α gal A expressed in CHO-cells.

Plants have both high mannose and complex glycans that differ from mammalian complex glycans by the presence of an α1,3 fucose on the proximal GlcNac and a β1,2 xylose on the β-linked mannose of the core. Four potential N-glycosylation sites have been identified for the plant derived α-galactosidase. The predicted amino acid sequence has four possible glycosylation sites (Asn-Xaa-Ser/Thr) at Asn residues (108, 161, 184, 377). The glycosylation site at amino acid 377 was not glycosylated, similar to CHO cell derived α-galactosidase glycosylation. The four possible N-glycosylation sites are all located in β turns within hydrophilic regions of the enzyme. It was estimated the mature human α-galactosidase consists of about 370 amino acids and approx. 15% carbohydrate (Calhoun et al. PNAS 82: 7364–7368, 1985). Matsuura et al (Glycobiology 8:329–339,1998) reports that in CHO-cell produced α gal there are four N-glycosylation sites (139, 193, 215, 407) and 3 of the 4 sites are occupied (407 is not glycosylated).

We have determined that our plant expressed protein is indeed glycosylated because the enzyme will bind to ConA which has a specificity for high mannose structures. Also, the plant derived enzyme was chemically deglycosylated with TFMS (trifluoromethanesulfonic acid). The α-galactosidase appeared to be cleaved as observed by a shift in molecular weight on both a silver stained gel and a Western blot with α gal antibody. Early attempts to cleave rGal-A with PNGaseF to release N-linked carbohydrate have been unsuccessful suggesting the presence of α1,3 fucose on the terminal GlcNac of the carbohydrate side chain. This was verified by glycan analysis work carried out by the Glycobiology Core Group at University of California San Diego Cancer Center. Carbohydrate profiling and compositional analysis was done. NMR experiments confirmed that rGal-A from the plant IF contains an N-linked glycan containing plant-specific carbohydrate linkages of a β1,2 xylose and α1,3 fucose on the trimannosyl core. This N-linked structure has been previously reported to occur in glycoproteins isolated from plant seeds and tissue cultures. 5 μg was hydrolyzed with 2M TFA for 4 hours and analyzed by HPAEC-PAD. The total amount of sugar and sugar content was 560 ug and 12%. NMR analysis of the major peak showed a trimannosyl-chitobiose core, with α1,3 linked fucose and a β1,2 linked xylose.

α-galactosidase glycan structures were determined by MALDI-TOF and/or MALDI-MS in collaboration with the Universitaet fuer Bodenkultur, see Table 13. For MALDI, 5 μg of plant derived α-galactosidase was digested with pepsin in a mass ratio of 1:40 in 5% formic acid. After evaporation the peptides were dissolved in ammonium acetate buffer, pH 5.0, boiled and subsequently digested with PNGase A overnight. Since the sample has a mass of 49.000 g/mol, there are 100 pmol of glycoprotein. After evaporation, the peptides were removed by cation exchange chromatography and the glycans are analyzed by MALDI (or pyridylaminated).

The molecular mass of the glycan was determined by MALDI-MS using a ThermoBio Analysis DYNAMO (linear MALDI-TOF MS with delayed extraction) instrument. A small portion of the sample was dried on the sample target and subsequently overlaid with "matrix" (gentisic acid). The samples contained complex type sugar chains with fucose, xylose and varying amounts of terminal GlcNAc. Small fractions were devoid of fucose and therefore amenable to hydrolysis by PNGase F.

TABLE 13

| Glycan Structure | Molecular Weight Daltons | Lot #980805 % Glycan Structure | Lot #981215 % Glycan Structure |
|---|---|---|---|
| MOXF | 1050.5 | 3 | — |
| MMX | 1066.5 | 2 | 2 |
| MMXF | 1212.7 | 22 | 8 |
| Man 5 | 1237.5 | — | 1.8 |
| GnMX/MGnX | 1269.8 | 6 | 0.5 |
| GnMXF/MGnXF | 1416.4 | 53 | 16 |
| GnGnX | 1473.3 | 5 | 7 |
| GnGnXF | 1619.9 | 9 | 55 |

TABLE 14

| Characteristic | Plant Derived | CHO Cell Secreted |
|---|---|---|
| Number of Core Structures | 8 | 23 |
| Sialic Acid | Absent | Present |

TABLE 14-continued

| Characteristic | Plant Derived | CHO Cell Secreted |
|---|---|---|
| Xylose | β (1,2) Linkage | Absent |
| Fucose | α (1,3) Linkage | α (1,6) Linkage |
| % Complex Structures | | |
| % Weight Glycosylated | 10–12% | 15% |
| Specific Activity | | |

TABLE 15

| α-Galactosidase Source | Specific Activity 4-MU Substrate | Reference |
|---|---|---|
| Nicotiana benthamiana Human, Recombinant | $5.0 \times 10^6$ | This Patent Application |
| Human Spleen | $1.88 \times 10^6$ | Bishop and Desnick, 1981, J. Biol. Chem. 256 (3): 1307–1316 |
| Human Placenta | $0.99 \times 10^6$ | Bishop and Desnick, 1981, J. Biol. Chem. 256 (3): 1307–1316 |
| Human Plasma | $7.4 \times 10^5$ | Bishop and Sweeley, 1978, Biochim. Bioph. Acta, 525:399–409 |

This example demonstrates the ability to extract two different products from the same leaf tissue based upon extraction procedures that specifically target products localized in the apoplast and cytosol.

Although the invention has been described with reference to the presently preferred embodiments, it should be understood that various modifications can be made without departing from the spirit of the invention.

All publications, patents, patent applications, and web sites are herein incorporated by reference in their entirety to the same extent as if each individual patent, patent application, or web site was specifically and individually indicated to be incorporated by reference in its entirety.

Literature Cited

1. Brady, R. O. Fabry Disease, In: Peripheral Neropathym 3rd ed., J. W. Griffin, P. A. Low, and J. F. Poduslo (eds.) W. B. Saunders. pp. 1169, 1993.
2. Desnick, R. J., Ioannou, Y. A., and Eng, C. M. Alpha-Galactosidase A Deficiency: Fabry Disease, In: The Metabolic Bases of Inherited Diseases, C. R. Scriver, A. L. Beaudet, W. S. Sly, D. Valle (eds.) McGraw-Hill, pp. 2741, 1995.
3. Brady, R. O. Sphingolipidoses, a Medical Progress Report. N. Engl. J. Med. 275: 312, 1966.
4. Brady R. O., Pentchev P. G., Gal A. E., Hibbert S. R., and Dekaban A. S. Replacement therapy for inherited enzyme deficiency: Use of purified glucocerebrosidase in Gaucher's disease. N. Engl. J. Med. 291:989, 1974.
5. Furbish F. S., Blair H. E., Shiloach J., Pentchev P. G., and Brady R. O. Enzyme replacement therapy in Gaucher's disease: Large-scale purification of glucocerebrosidase suitable for human administration. Proc. Natl. Acad. Sci. USA 74: 560, 1977.
6. Furbish F. S., Steer C. J., Krett N. L., and Barranger, J. A. Uptake and distribution of placental glucocerebrosidase in rat hepatic cells and effects of sequential deglycosylation. Biochim. Biophys. Acta 673: 425, 1981.
7. Barton, N. W., Furbish, F. S., Murray, G. J., Garfield, M., and Brady, R. O. Therapeutic response to intravenous infusions of glucocerebrosidase in a patient with Gaucher disease. Proc. Natl. Acad. Sci. USA 87: 1913, 1990.

8. Barton, N. W., Brady, R. O., Dambrosia, J. M., DiBisceglie, A. M., Doppelt, S. H., Hill, S. C., Mankin, H. J., Murray, G. J., Parker, R. I., Argoff, C. E., Grewal, R. P., and Yu, K. -T. Replacement therapy for inherited enzyme deficiency—macrophage-targeted glucocerebrosidase for Gaucher's disease. N. Engl. J. Med. 324: 1464, 1991.
9. Parker, R. I., Barton, N. W., Read, E. J., and Brady, R. O. Hematologic improvement in a patient with Gaucher's disease on long-term replacement therapy: Evidence for decreased splenic sequestration and improved red blood cell survival. Am. J. Hematol. 38: 130, 1991.
10. Hill, S. C., Parker, C. C., Brady, R. O., and Barton, N. W. MRI of multiple platyspondyly in Gaucher disease: Response to enzyme replacement therapy. J. Comput. Assist. Tomog. 17: 806, 1993.
11. Beutler, E., Kay, A., Saven, A., Garver, P., Thurston, D., Dawson, A., and Rosenbloom, B. Enzyme replacement therapy for Gaucher disease. Blood 78:1183, 1991.
12. Fallet, S., Grace, M. E., Sibille, A., Mendelson, D. S., Shapiro, R. S., Hermann, G., and Grabowski, G. A. Enzyme augmentation in moderate to life-threatening Gaucher disease. Pediatr. Res. 31: 496, 1992.
13. Mistry, P. K., Davies, S., Corfield, A., Dixon, A. K., and Cox, T. M. Successful treatment of bone marrow failure in Gaucher's disease with low-dose modified glucocerebrosidase. Quart. J. Med. New Series 84: 541, 1992.
14. Grabowski, G. A., Barton, N. W., Pastores, G., Dambrosia, J. M., Banerjee, T. K., McKee, M. A., Parker, C., Schiffmann, R., Hill, S. C., Brady, R. O. Enzyme therapy in Type 1 Gaucher disease: Comparative efficacy of mannose-terminated glucocerebrosidase from natural and recombinant sources. Ann. Inter. Med. 122:33, 1995.
15. Hasholt L., Sorensen, S. A. A microtechnique for quantitative mesurements of acid hydrolases in fibroblasts. Its application in diagnosis of Fabry disease and enzyme replacement studies. Clin. Chim. Acta 142:257, 1984.
16. Mapes, C. A., Anderson, R. L., Sweeley, C. C., Desnick, R. J., Krivit, W. Enzyme replacement in Fabry's disease, an inborn error of metabolism. Science 169:987, 1970.
17. Brady, R. O., Tallman, J. F., Johnson, W. G., Gal, A. E., Leahy, W. R., Quirk, J. M., Dekaban, A. S. Replacement therapy for inherited enzyme deficiency: Use of purified ceramidetrihexosidease in Fabry's disease. N. Eng. J. Med. 289:9, 1973.
18. Desnick, R. J., Dean, K. J., Grabowski, G. A., Bishop, D. F., Sweeley, C. C. Enzyme therapy XII: Enzyme therapy in Fabry's disease: Differential enzyme and substrate clearance kinetics of plasma and splenic Alpha-galactosidase isozymes. Proc. Natl. Acad. Sci USA 76:5326, 1979.
19. Beutler, E. The cost of treating Gaucher disease. Nature Medicine 2:523, 1996.
20. NIH Technology Assessment Panel on Gaucher Disease. Gaucher Disease: Current issues in diagnosis and treatment. JAMA 275:548, 1995.
21. Hiatt, A., Cafferkey, R., and Bowdish, K. Production of antibodies in transgenic plants. Nature 342:76, 1989.
22. Assembly of multimeric proteins in plant cells: Characteristics and uses of plant-derived antibodies, In: Transgenic Plants, Fundamentals and Applications, A. Hiatt, (ed.) Marcel Dekker, Inc. New York, N.Y. pp. 221, 1992.
23. Ma, J. K.-C., and Hein, M. B. Plant antibodies for immunotherapy. Plant Physiol. 109:341, 1995.
25. Sijmons, P. C., Dekker, B. M. M., Schrammeijer, B., Verwoerd, T. C., van den Elzen, P. J. M., and Hoekema, A. Production of correctly processed human serum albumin in transgenic plants. Bio/Technology 8:217, 1990.
26. Mason, H. S., Lam D. M.-K., and Arntzen, C. J. Expression of hepatitis B surface antigen in transgenic plants. Proc. Natl. Acad. Sci. USA 89:11745, 1992.
27. Haq, T. A., Mason, H. S., Clements, J. D., and Arntzen, C. J. Oral immunization with a recombinant bacterial antigen produced in transgenic plants. Science 268:714, 1995.
28. Turpen, T. H., Reinl, S. J., Charoenvit, Y., Hoffman, S. L., Fallarme, V., and Grill, L. K. Malarial epitopes expressed on the surface of recombinant tobacco mosaic virus. Bio/Technology 13:53, 1995.
29. Kumagai, M. H., Turpen, T. H., Weinzettl, N., della-Cioppa, G., Turpen, A. M., Donson, J., Hilf, M. E., Grantham, G. L., Dawson, W. O., Chow, T. P., Piatak Jr., M., and Grill, L. K. Rapid, high level expression of biologically active □-trichosanthin in transfected plants by a novel RNA viral vector. Proc. Natl. Acad. Sci. USA 90:427, 1993.
30. Turpen, T. H., and Dawson, W. O Amplification, movement and expression of genes in plants by viral-based vectors, In: Transgenic Plants, Fundamentals and Applications, A. Hiatt, (ed.) Marcel Dekker, Inc. New York, N.Y. pp. 195, 1992.
31. Sugimoto, Y., Aksentijevich, I., Murray, G. J., Brady, R. O., Pastan, I., and Gottesman, M. M. Retroviral coexpression of a multidrug resistance gene (MDRI) and human Alpha-galactosidase A for gene therapy of Fabry disease. Human Gene Therapy 6:905, 1995.
32. O'Neill, S. D., Kumagai, M. H., Majumdar, A., Huang, N., Sutliff, T. D. and Rodriguez, R. L. The α-amylase genes in $Oryza\ sativa$: Characterization of cDNA clones and MRNA expression during seed germination. Mol. Gen. Genet. 221:235, 1990.
33. Kumagai, M. H., Shah, M., Terashima, M., Vrkljan, Z., Whitaker, J. R., and Rodriguez, R. L. Expression and secretion of rice α-amylase by $Saccharomyces\ cerevisiae$. Gene 94:209, 1990.
34. Suzuki, K. Enzymatic diagnosis of sphingolipidoses. Meth. Enzy. 138:727, 1987.
35. Chrispeels, M. J. Sorting of proteins in the secretory system. Annu. Rev. Plant Physiol. Plant Mol. Biol. 42:21, 1991.
36. Ioannou, Y. A., Bishop, D. F., and Desnick, R. J. Overexpression of human Alpha-galactosidase A results in its intracellular aggregation, crystallization in lysosomes, and selective secretion. J. Cell Biol. 119:1137, 1992.
37. Dombrowski, J. E., and Raikhel, N. V. Protein targeting to the plant vacuole—a historical perspective. Brazilian Journal of Medical and Biological Research 29:413, 1996.
38. Kermode, A. R. Mechanisms of intracellular protein transport and targeting in plant cells. Crit. Rev. Plant Sci. 15:285, 1996.
39. Bishop, D. F., Calhoun, D. H., Bernstein, H. S., Hantzopoulos, P., Quinn, M., and Desnick, R. J. Human Alpha-galactosidase A: Nucleotide sequence of a cDNA clone encoding the mature enzyme. Proc. Natl. Acad. Sci. USA 83:4859, 1986.
40. Quinn, M., Hantzopoulos, P., Fidanza, V. and Calhoun, D. H. A genomic clone containing the promoter for the gene encoding the human lysosomal enzyme, Alpha-galactosidase A. Gene 58:177, 1987.
41. Coppola, G., Yan, Y., Hantzopoulos, P., Segura, E., Stroh, J. G., and Calhoun, D. H. Characterization of glycosylated and catalytically active recombinant human Alpha-galactosidase A using a baculovirus vector. Gene 144:197.

42. Miyamura, N., Araki, E., Matsuda, K., Yoshimura, R., Furukawa, N., Tsuruzoe, K., Shirotani, T., Kishikawa, H., Yamaguchi, K., and Shichiri, M. A carboxy-terminal truncation of human Alpha-galactosidase A in a heterozygous female with Fabry disease and modification of the enzymatic activity by the carboxy-terminal domain. J. Clin. Invest. 18009, 1996.

43. National Research Council. Putting biotechnology to work. Bioprocess engineering. National Academy Press, Washington, D.C. 1992.

44. Prescribing Information, Ceredase™, (alglucerase injection). Genzyme Corporation, 1/1995.

45. Wilkins, T., Bednarek, S. Y., Raikhel, N. V. Role of propetide glycan in post-translational processing and transport of barley lectin to vacuoles in transgenic tobacco. Plant Cell 2:301, 1990.

46. Melchers, L. S., Sela-Buurlage, M. B., Vloemans, S. A., Woloshuk, C. P., Van Roekel, J. S. C., Pen, J., Van den Elzen, P. J. M., Cornelissen, B. J. C. Extracellular targeting of the vacuolar tobacco proteins AP24, chitinase and □-1,3-glucanase in transgenic plants. Plant Mol. Biol. 21:583, 1993.

47. Sato, F., Koiwa, H., Sakai, Y., Kato, N., Yamada, Y. Synthesis and secretion of tobacco neutral PR-5 protein by transgenic tobacco and yeast. Biochem. Biophys. Res. Comm. 211:909, 1995.

48. Maggio, A., D'Urzo, M. P., Abad, L. R., Takeda, S., Hasegawa, P. M., and Bressan, R. Large quantities of recombinant PR-5 proteins from the extracellular matrix of tobacco: Rapid production of microbial-recalcitrant proteins. Plant Mol. Biol. Rep. 14:249, 1996.

49. Calhoun, D. H., Bishop, D. F., Bernstein, H. S., Quinn, M., Hantzopoulos, P., Desnick, R. J. Fabry disease: Isolation of a cDNA clone encoding human Alpha-galactosidase A. Proc. Natl. Acad. Sci. USA 82:7364, 1985.

50. Jenkins, N., Parekh, R. B., James, D. C. Getting the glycosylation right: Implications for the biotechnology industry. Nature Biotech. 14:975, 1996.

51. Fitchette-Lainé, A-C., Gomord, V., Chekkafi, A., and Faye, L. Distribution of xylosylation and fucosylation in the plant Golgi apparatus. Plant J. 5:673, 1994.

52. Hein, M. B., Tang, Y., McLeod, D. A., Janda, K. D., Hiatt, A. C. Evaluation of immunoglobulins from plant cells. Biotechnol. Prog. 7:455, 1991.

53. Garcia-Casado, G. Sanchez-Monge, R., Chrispeels, M. J., Armentia, A., Salcedo, G., and Gomez, L. Role of complex asparagine-linked glycans in the allergenicity of plant glycoproteins. Glycobiol. 6:471, 1996.

54. Chrispeels, M. J., and Faye, L. The production of recombinant glycoproteins with defined non-immunogenic glycans, In: Transgenic Plants, A production system for industrial and pharmaceutical proteins. M. R. L. Owen and J. Pen, (eds.) John Wiley & Sons Ltd. pp. 99, 1996.

55. von Schaewen, A., Strum, A., O'Neill, J., Chrispeels, M. J. Isolation of a mutant Arabidopsis plant that lacks N-acetyl glucosaminyl transferase I and is unable to synthesize golgi-modified complex N-linked glycans. Plant Physiol. 102:1109, 1993.

56. Takasaki, S., Murray, G. J., Furbish, F. S., Brady, R. O., Barranger, J. A., and Kobata, A. Structure of the N-asparagine-linked oligosaccharide units of human placental α-glucocerebrosidase. J. Biol. Chem. 259:10112, 1984.

57. Murray, G. J., Lectin-specific targeting of lysosomal enzymes to reticuloendothelial cells. Meth. Enzy. 149:25, 1987.

58. Ohshima, T., Murray, G. J., Nagle, J. W., Quirk, J. M., Kraus, M. H., Barton, N. W., Brady, R. O., and Kulkarni, A. B. Structural organization and expression of the mouse gene encoding Alpha-galactosidase A. Gene 166:277, 1995.

59. Horsch et al., Science 227 (1985) 1229–1231.

60. An, G., Watson, B D, Chiang, C C Plant Physiol 81 (1986) 301–305.

61. Gelvin, S B, Schilperoort, R A (eds.) Plant Molec Biol Manual (1988).

62. Kint, 1971, Arch. Int. Physiol. Biochem. 79:633–644.

63. Beutler & Kuhl, 1972, Amer. J. Hum. Genet. 24:237–249.

64. Romeo, et al., 1972, FEBS Lett. 27:161–166.

65. Wood & Nadler, 1972, Am. J. Hum. Genet. 24:250–255.

66. Ho, et al., 1972, Am. J. Hum. Genet. 24:256–266.

67. Desnick, et al., 1973, J. Lab. Clin. Med. 81:157–171.

68. Desnick, et al., 1989, in The Metabolic Basis of Inherited Disease, Scriver, C. R., Beaudet, A. L. Sly, W. S. and Valle, D., eds, pp. 1751–1796, McGraw Hill, New York.

69. Kint, 1971, Arch. Int. Physiol. Biochem. 79:633–644.

70. Beutler & Kuhl, 1972, J. Biol. Chem. 247: 7195–7200.

71. Callahan, et al., 1973, Biochem. Med. 7: 424–431.

72. Dean, et al., 1977, Biochem. Biophys. Res. Comm. 77:1411–1417.

73. Schram, et al., 1977, Biochim. Biophys. Acta. 482:138–144.

74. Kusiak, et al., 1978, J. Biol. Chem. 253:184–190.

75. Dean, et al., 1979, J. Biol. Chem. 254:10001–10005.

76. Bishop, et al., 1980, in Enzyme Therapy in Genetic Disease:2, Desnick, R. J., ed., pp. 17–32, Alan R. Liss, Inc., New York.

77. Beutler & Kuhl, 1972, J. Biol. Chem. 247:7195–7200.

78. Schram, et al., 1977, Biochim. Biophys. Acta. 482:138–144).

79. Kint, 1971; Arch. Int. Physiol. Biochem. 79: 633–644.

We claim:

1. An isolated polypeptide consisting of the amino acid sequence of the α-galactosidase as depicted in SEQ ID NO: 12.

2. The isolated polypeptide according to claim 1, wherein said polypeptide is glycosylated at least at one amino acid position.

3. The isolated polypeptide according to claim 1, wherein said polypeptide has a plant glycosylation pattern.

\* \* \* \* \*

UNITED STATES PATENT AND TRADEMARK OFFICE
CERTIFICATE OF CORRECTION

PATENT NO. : 6,890,748 B2  Page 1 of 1
APPLICATION NO. : 10/103327
DATED : May 10, 2005
INVENTOR(S) : Garger et al.

It is certified that error appears in the above-identified patent and that said Letters Patent is hereby corrected as shown below:

In Section (75), Inventors:
Stephen J. Garger, Vacaville, CA (US); Thomas H. Turpen, Vacaville, CA (US); Monto H. Kumagai, Kailua, HI (US); insert -- Gregory P. Pogue, Vacaville, CA (US) --

Column 12,
Line 6, delete "Mosiac" and insert -- Mosaic -- ;
Line 12, delete "Mosiac" and insert -- Mosaic -- ;
Line 33, delete "carbozy" and insert -- carboxy -- ;
Line 59, delete "tobamovrius" and insert -- tobamovirus -- ;

Column 13,
Line 33, delete "acetylgalactosaminidise" and insert -- acetylgalactosaminidase --

Column 14,
Line 9, delete "sialidese" and insert -- sialidase --

Column 26,
Table 2, Line 4, delete "CHROMOTOGRAPHY" and insert
-- CHROMATOGRAPHY --

Column 31,
Table 6, first line, delete "INITAL" and insert -- INITIAL --

Column 51,
Line 34, delete "mesurements" and insert -- measurements --

Signed and Sealed this

Twenty-sixth Day of September, 2006

JON W. DUDAS
*Director of the United States Patent and Trademark Office*